(12) United States Patent
Alabugin et al.

(10) Patent No.: US 9,708,351 B2
(45) Date of Patent: Jul. 18, 2017

(54) ALKENES AS ALKYNE EQUIVALENTS IN RADICAL CASCADES TERMINATED BY FRAGMENTATIONS

(71) Applicant: The Florida State University Research Foundation, Inc., Tallahassee, FL (US)

(72) Inventors: Igor V. Alabugin, Tallahassee, FL (US); Sayantan Mondal, Tallahassee, FL (US); Rana K. Mohamed, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/143,669

(22) Filed: May 2, 2016

(65) Prior Publication Data
US 2016/0347778 A1 Dec. 1, 2016

Related U.S. Application Data

(60) Provisional application No. 62/167,405, filed on May 28, 2015.

(51) Int. Cl.
| | | |
|---|---|---|
| C07C 17/093 | (2006.01) | |
| C07C 29/42 | (2006.01) | |
| C07F 7/22 | (2006.01) | |
| C07C 1/32 | (2006.01) | |
| C07C 45/00 | (2006.01) | |
| C07D 333/08 | (2006.01) | |
| C07D 213/16 | (2006.01) | |
| C07D 239/26 | (2006.01) | |
| C07C 253/30 | (2006.01) | |
| C07C 41/01 | (2006.01) | |
| C07C 41/16 | (2006.01) | |
| C07C 41/30 | (2006.01) | |
| C07C 67/333 | (2006.01) | |

(52) U.S. Cl.
CPC ............ *C07F 7/2212* (2013.01); *C07C 1/325* (2013.01); *C07C 17/093* (2013.01); *C07C 29/42* (2013.01); *C07C 41/01* (2013.01); *C07C 41/16* (2013.01); *C07C 41/30* (2013.01); *C07C 45/00* (2013.01); *C07C 67/333* (2013.01); *C07C 253/30* (2013.01); *C07D 213/16* (2013.01); *C07D 239/26* (2013.01); *C07D 333/08* (2013.01); *C07C 2103/10* (2013.01)

(58) Field of Classification Search
CPC ..... C07C 1/325; C07C 17/093; C07C 253/30; C07C 29/42; C07C 41/30; C07C 67/333; C07D 213/16; C07D 239/26; C07D 333/08; C07F 7/2212

See application file for complete search history.

(56) References Cited

U.S. PATENT DOCUMENTS

| | | | |
|---|---|---|---|
| 8,410,303 B2 | 4/2013 | Alabugin et al. | |
| 8,927,728 B2 | 1/2015 | Alabugin et al. | |
| 8,927,778 B2 | 1/2015 | Alabugin et al. | |
| 9,206,100 B2 | 12/2015 | Alabugin et al. | |
| 9,273,023 B2 | 3/2016 | Alabugin et al. | |
| 2013/0196985 A1 | 8/2013 | Ding et al. | |

FOREIGN PATENT DOCUMENTS

WO 2012037062 A3 3/2012

OTHER PUBLICATIONS

Mohamed et al., Alkenes as Alkyne equivalents in Radical Cascades Terminated by Fragmentations: Overcoming Stereoelectronic Restrictions on Ring Expanstions for the Preparation of Expanded Polyaromatics, JACS, 2015, 137, pp. 6335-6349 (published Apr. 23, 2015).*
Pati et al., Synthesis of Functionalized Phenanthrenes via Regioselective Oxidative Radical Cyclization, JOC, 2015, 80, pp. 11706-11717 (published Aug. 6, 2015).*
Mallory, Frank B. et al., Phenacenes: a family of graphite ribbons. Part 3: Iterative strategies for the synthesis of large phenacenes, Tetrahedron, 57, © 2001 Elsevier Science Ltd., (2001) pp. 3715-3724.
Wu , Jishan et al., Graphenes as Potential Material for Electronics, Chemical Reviews, vol. 107, No. 3, © 2007 American Chemical Society, (2007), pp. 718-747.
Berresheim, Alexander J. et al., Polyphenylene Nanostructures, Chemical Reviews, vol. 99, No. 7, © 1999 American Chemical Society, (1999), pp. 1747-1785.
Geim , A.K. et al., The Rise of Graphene, Nature Materials, vol. 6, © 2007 Nature Publishing Group, (March 2007), pp. 183-191.
Kuninobu, Yoichiro et al., Synthesis of Functionalized Pentacenes from Isobenzofurans Derived from C—H Bond Activation, Organic Letters, vol. 12, No. 22, © 2010 American Chemical Society, (Oct. 20, 2010), pp. 5287-5289.

(Continued)

*Primary Examiner* — Deepak Rao
(74) *Attorney, Agent, or Firm* — Armstrong Teasdale LLP

(57) ABSTRACT

Disclosed are methods for rerouting radical cascade cyclizations by using alkenes as alkyne equivalents. The reaction sequence is initiated by a novel 1,2 stannyl shift which achieves chemo- and regioselectivity in the process. The radical "hopping" leads to the formation of the radical center necessary for the sequence of selective cyclizations and fragmentations to follow. In the last step of the cascade, the elimination of a rationally designed radical leaving group via β-C—C bond scission aromatizes the product without the need for external oxidant. The Bu₃Sn moiety, which is installed during the reaction sequence, allows further functionalization of the product via facile reactions with electrophiles as well as Stille and Suzuki cross-coupling reactions. This selective radical transformation opens a new approach for the controlled transformation of enynes into extended polycyclic structures of tunable dimensions.

7 Claims, 14 Drawing Sheets

(56) References Cited

OTHER PUBLICATIONS

Scherf, Ullrich, Ladder-type materials, J. Mater. Chem., vol. 9, 1999, pp. 1853-1864.
Allen, Matthew J. et al., Honeycomb Carbon: A Review of Graphene, Chemical Reviews, vol. 110, No. 1, © 2010 American Chemical Society, (Jul. 17, 2009), pp. 132-145.
Goldfinger, Marc B. et al., Fused Polycyclic Aromatics via Electrophile-Induced Cyclization Reactions: Application to the Synthesis of Graphite Ribbons, J. Am. Chem. Soc., vol. 116, No. 17, ©1994 American Chemical Society, (1994), pp. 7895-7896.
Swartz, Christopher R. et al., Synthesis and Characterization of Electron-Deficient Pentacenes, Organic Letters, vol. 7, No. 15, © 2005 American Chemical Society, (Jun. 30, 2005), pp. 3163-3166.
Li, Xiaolin et al., Chemically Derived, Ultrasmooth Graphene Nanoribbon Semiconductors, Science, vol. 319, © 2008 by the American Association for the Advancement of Science, (Feb. 29, 2008), pp. 1229-1232.
Paquette, Lee et al., The Square Ester—Polyquinane Connection. An Analysis of the Capacity of Achiral Divinyl Adducts to Rearrange Spontaneously to Polycyclic Networks Housing Multiple Sterogenic Centers, J. American Chemical Society, 1997, vol. 119, pp. 1230-1241.
Pollart, Daniel J. et al., Generation of (Trimethylsiloxy)(phenylethynyl)ketene and (Trimethylsiloxy)cyanoketene and Their Reactions with Some Alkynes, Journal of Org. Chemical, 1989, vol. 54, pp. 5444-5448.
Arns, Steve et al., Cascading pericyclic reactions: building complex carbon frameworks for natural product synthesis, Chem. Commun., 2007, pp. 2211-2221, The Royal Society of Chemistry.
Baldwin, Jack E. et al., Rules for Ring Closure: Application to Intramolecular Aldol Condensations in Polyketonic Substrates, Tetrahedron, 1982, pp. 2939-2947, vol. 38, No. 19, Great Britain.
Butenschon, Holger, Arene chromium complexes with functionalized anellated rings. Selective formation of nighly substituted polycycles, Pure Appl. Chem., 2002, pp. 57-62; vol. 74, No. 1, IUPAC.
Carpenter, Barry K., A Simple Model for Predicting the Effect of Substituents on the Rates of Thermal Pericyclic Reactions, Tetrahedron, 1978, pp. 1877-1884, vol. 34, Pergamon Press Ltd.
Dahnke, Karl R. et al., Exploratory Synthetic Studies Involving the Tricyclo[9.3.0.02,8]tetradecane Ring System Peculiar to the Cyathins, J. Org. Chem., 1994, pp. 885-899, vol. 59, American Chemical Society.
Gentric, Lionel et al., Rate Acceleration of Anionic Oxy-Cope Rearrangements Induced by an Additional Unsaturation, Organic Letters, 2003, pp. 3631-3634, vol. 5, No. 20, American Chemical Society.
Graulich, Nicole et al., Heuristic thinking makes a chemist smart, Chemical Society Reviews, 2010, pp. 1503-1512, vol. 39, The Royal Society of Chemistry.
Huntsman, William D. et al., The Thermal Rearrangement of 1,5-Hexadiyne and Related Compounds, J. Org. Chem., Jan. 18, 1967, pp. 342-347, vol. 89, No. 2, Journal of the American Chemical Society.
Evans, D.A. et al., [3,3] Sigmatropic Rearrangements of 1,5-Diene Alkoxides. The Powerful Accelerating Effects of the Alkoxide Substituent, Journal of the American Chemical Society, Aug. 6, 1975, pp. 4765-4766, vol. 97, No. 16, American Chemical Society.
Evans, D.A. et al., A General Approach to the Synthesis of 1,6 Dicarbonyl Substrates. New Applications of Base-Accelerated Oxy-Cope Rearrangements, Journal of the American Chemical Society, Mar. 29, 1978, pp. 2242-2244, vol. 100, No. 7, American Chemical Society.
Jacobi, Peter A. et al., Bis Heteroannulation. 7. Total Syntheses of (+)-Chididione and (+)-Isognididione, J. Am. Chem. Soc., 1987, pp. 3041-3043, vol. 106, Amerian Chemical Society.
Paquette, Leo A., Recent Applications of Anionic Oxy-Cope Rearrangements, Tetrahedron Report No. 429, 1997, pp. 13971-14020, vol. 52, No. 41, Elsevier Science Ltd, Great Britian.
Roth, Wolfgang R. et al., A "Frustrated" Cope Rearrangement: Thermal Interconversion of 2,6-Diphenylhepta-1,6-diene and 1,5-Diphenylbicyclo[3.2.0]heptain, Journal of the American Chemical Society, 1990, pp. 1722-1732, vol. 112, American Chemical Society.
Pal, Runa et al., Fast Oxy-Cope Rearrangements of Bis-alkynes: Competition with Central C—C Bond Fragmentation and Incorporation in Tunable Cascades Diverging from a Common Bis-allenic Intermediate, JOC Note, 2010, pp. 8689-8692, vol. 75, J. Org. Chem.
Zimmerman, Howard E., Kinetic Protonation of Enols, Enolates, and Analogues. The Stereochemistry of Ketonization, Acc. Chem Res., 1987, pp. 263-268, vol. 20, American Chemical Society.
Zimmerman, Howard E. et al, The Stereochemistry of Allenic Enol Tautomerism—Independent Generation and Reactivity of he Enolates, Eur. J. Org. Chem., 2006, pp. 3491-3497, Wiley-VCH Verlag GmbH & Co.
Pati, Kamalkishore, et al., Exo-Dig Radical Cascades of Skipped Enediynes: Building a Naphthalene Moiety within a Polycyclic Framework, Chemistry, A European Journal, 2014, vol. 20, pp. 390-393.
Mondal, Sayantan et al., "Design of Leaving Groups in Radical C—C Fragmentations: Through-Bond 2c-3e Interactions in Self-Terminating Radical Cascades," Chemistry, A European Journal, 2014, pp. 8664-8669, vol. 20, Wiley Online Library.

* cited by examiner

FIG. 13B

ALKENES AS ALKYNE EQUIVALENTS IN RADICAL CASCADES TERMINATED BY FRAGMENTATIONS

CROSS REFERENCE TO RELATED APPLICATION(S)

This application claims the benefit of priority to U.S. provisional application Ser. No. 62/167,405, filed May 28, 2015. The disclosure of the priority document is hereby incorporated by reference as if set forth in its entirety.

STATEMENT REGARDING FEDERALLY SPONSORED RESEARCH OR DEVELOPMENT

This invention was made with Government support under Grant CHE-1213587 and Grant CHE-1152491 awarded by the National Science Foundation. The Government has certain rights in the invention.

FIELD OF THE INVENTION

The present invention generally relates to synthetic routes toward polyaromatic compounds.

BACKGROUND OF THE INVENTION

The alkyne group is a high-energy carbon-rich functionality that can serve as a perfect starting point for the preparation of conjugated molecules and materials. See Reference 1. For example, controlled cascade transformations featuring alkyne cyclizations provide practical means for the preparation of graphene nanoribbons. See References 1 through 4. On the other hand, alkenes, the reduced chemical cousins of alkynes, cannot serve as direct precursors for conjugated systems as alkenes cyclize to products that require an extra oxidizing step for aromatization.

Recently, we amplified the subtle chemical differences between alkenes and alkynes by utilizing dynamic covalent chemistry for the development of a regio- and chemoselective radical transformation of aromatic enynes into indenes. See References 5 and 6. Although both alkyne and alkene π-bonds are indiscriminately attacked by $Bu_3Sn$ radicals, the pool of four equilibrating isomeric radical intermediates is selectively depleted ("kinetically self-sorted") through the "matched" 5-exo trig cyclization of the most reactive of the four radicals at the more reactive alkene π-bond.

The following references, the disclosures of which are hereby incorporated as if set forth in their entirety, are cited herein:

[1] E. T. Chernick, R. R. Tykwinski, *J. Phys. Org. Chem.* 2013, 26, 742.
[2] I. V. Alabugin, B. Gold, *J. Org. Chem.* 2013, 78, 7777.
[3] a) K. Gilmore, I. V. Alabugin, *Chem. Rev.* 2011, 111, 6513. b) I. V. Alabugin, K. Gilmore, M. Manoharan, *J. Am. Chem. Soc.* 2011, 133, 12608. c) I. V. Alabugin; K. Gilmore, *Chem. Commun.* 2013, 49, 11246.
[4] a) L. T. Scott, *Angew. Chem. Int. Ed. Engl.* 2004, 43, 4994. b) M. B. Goldfinger, T. M. Swager, *J. Am. Chem. Soc.* 1994, 116, 7895. c) U. H. F. Bunz, *Chem. Rev.* 2000, 100, 1605. Selected examples from our group: d) I. V. Alabugin, K. Gilmore, S. Patil, M. Manoharan, S. V. Kovalenko, R. J. Clark, I. Ghiviriga, *J. Am. Chem. Soc.* 2008, 130, 11535. e) P. Byers; I. V. Alabugin, *J. Am. Chem. Soc.* 2012, 134, 9609. f) Byers, P. M.; Rashid, J. I.; Mohamed, R. K.; Alabugin, I. V. *Org. Lett.*, 2012, 14, 6032. g) K. Pati, A. M. Hughes, H. Phan, I. V. Alabugin, *Chem.-Eur. J.* 2014, 20, 390.
[5] S. J. Rowan, S. J. Cantrill, G. R. L. Cousins, J. K. M. Sanders, J. F. Stoddart, *Angew. Chem. Int. Ed.* 2002, 41, 898.
[6] S. Mondal, R. K. Mohamed, M. Manoharan, H. Phan, I. V. Alabugin, *Org. Lett.* 2013, 15, 5650.
[7] For a recent review on C—C fragmentations: M. A. Drahl, M. Manpadi, L. J. Williams, *Angew. Chem. Int. Ed.* 2013, 52, 11222.
[8] For the recent use of TS stabilization for control of alkyne reactivity, see a) B. Gold, G. B. Dudley, I. V. Alabugin, *J. Am. Chem. Soc.,* 2013, 135, 1558. b) B. Gold, N. Shevchenko, N. Bonus, G. B. Dudley, I. V. Alabugin, *J. Org. Chem.* 2012, 77, 75. c) K. Gilmore, M. Manoharan, J. Wu, P. v. R. Schleyer, I. V. Alabugin, *J. Am. Chem. Soc.* 2012, 134, 10584.
[9] a) D. Crich, A. Bowers, *Org. Lett.* 2006, 8, 4327. b) A. Baroudi, J. Alicea, P. Flack, J. Kirincich, I. V. Alabugin, *J. Org. Chem.* 2011, 76, 1521. c) A. Baroudi, P. Flack, I. V. Alabugin, *Chem.-Eur.* 12010, 16, 12316. d) A. Baroudi, J. Alicea, I. V. Alabugin, *Chem.-Eur. J.* 2010, 16, 7683. e) U. Wille, *Chem. Rev.* 2013, 113, 813. f) L. Debien, S. Zard, *J. Am. Chem. Soc.* 2013, 135, 3808. g) R. Heng, S. Z. Zard, *Chem. Commun.* 2011, 47, 3296. h) F. M. Kessabi, T. Winkler, J. A. R. Luft, K. N. Houk, *Org. Lett.* 2008, 10, 2255. i) J. A. R. Luft, T. Winkler, F. Murphy, F. M. Kessabi, K. N. Houk, *J. Org. Chem.* 2008, 73, 8175. j) B. Quiclet-Sire, S. Z. Zard, *Beilstein J. Org. Chem.* 2013, 9, 557. Similar transformation catalyzed by a radical S-Adenosyl methionine (SAM) enzyme: k) N. Mahanta; D. Fedoseyenko, T. Dairi, T. P. Begley, *J. Am. Chem. Soc.* 2013, 135, 15318.
[10] For further information about polarity reversal catalysis, see: a) S. J. Cole, J. N. Kirwan, B. P. Roberts, C. R. J. Willis, Chem. Soc., Perkin Trans. 1 1991, 103. b) B. P. Roberts, *Chem. Soc. Rev.* 1999, 28, 25. c) Y. Cai, B. P. J. Roberts, Chem. Soc., Perkin Trans. 2 2002, 1858. d) C. Chatgilialoglu, Organosilanes in Radical Chemistry; Wiley: New York, 2004. (e) C. H. Schiesser, M. A. Skidmore, *J. Chem. Soc., Perkin Trans.* 2, 1998, 2329. (f) J. Guin, C. Mueck-Lichtenfeld, S. Grimme, A. Studer, *J. Am. Chem. Soc.* 2007, 129, 4498. (g) D. Crich, D. Grant, V. Krishnamurthy, M. Patel, *Acc. Chem. Res.* 2007, 40, 453.
[11] S. J. Blanksby, G. B. Ellison, *Acc. Chem. Res.* 2003, 36, 255.
[12] D. Crich, D. Grant, V. Krishnamurthy, M. Patel, *Acc. Chem. Res.* 2007, 40, 453.
[13] L. F. Loucks, K. J. Laidler, *Can. J. Chem.* 1967, 45, 2785.
[14] I. V. Alabugin, M. Manoharan, T. A. Zeidan, *J. Am. Chem. Soc.* 2003, 125, 14014.
[15] I. V. Alabugin, K. Gilmore, P. Peterson, *WIREs Comput Mol Sci.* 2011, 1, 109.
[16] a) R. Hoffmann, *Acc. Chem. Res.* 1971, 4, 1. b) R. Gleiter, *Angew. Chem. Int. Ed.* 1974, 13, 696. c) M. N. Paddon-Row, *Acc. Chem. Res.* 1982, 15, 245. d) M. Abe, *Chem. Rev.* 2013, 113, 7011. d) R. Gleiter, G. Haberhauer, in *Aromaticity and Other Conjugation Effects*, Wiley-VCH, Weinheim, 2012.
[17] a) R. K. Mohamed, P. W. Peterson, I. V. Alabugin, *Chem. Rev.* 2013, 7089. b) I. V. Alabugin, M. Manoharan, *J. Phys. Chem. A* 2003, 107, 3363.
[18] a) C. F. Logan, P. Chen, *J. Am. Chem. Soc.* 1996, 118, 2113. (b) M. J. Schottelius, P. Chen, *J. Am. Chem. Soc.* 1996, 118, 4896. (c) R. R. Squires; C. J. Cramer, *J. Phys.*

Chem. A 1998, 102, 9072. (d) E. Kraka, D. Cremer, *J. Am. Chem. Soc.* 2000, 122, 8245. (e) F. C. Pickard IV, R. L. Shepherd, A. E. Gillis, M. E. Dunn, S. Feldgus, K. N. Kirschner, G. C. Shields, M. Manoharan, I. V. Alabugin, *J. Phys. Chem. A.* 2006, 110, 2517.

[19] While there are a few isolated examples of decreased ionization potentials in N,N-dimethylpiperazine and its derivatives, control of reactivity via such interactions is, to the best of our knowledge, absent from the literature. This is likely due to the decreased driving force for the fragmentation, where an extra electron is in an antibonding orbitals and one of the formed bonds is the 2c-3e "half-bond". a) A. M. Brouwer, J. M. Zwier, C. Svendsen, O. S. Mortensen, F. W. Langkilde, R. Wilbrandt, *J. Am. Chem. Soc.* 1998, 120, 3748. b) G. Balakrishnan, T. Keszthelyi, R. Wilbrandt, J. M. Zwier, A. M. Brouwer, W. J. Buma. *J. Phys. Chem. A,* 2000, 104, 1834. c) S. Deb, X. Cheng, P. M. Weber, *J. Phys. Chem. Lett.* 2013, 4, 2780.

[20] a) R. A. Marcus, *J. Chem. Phys.* 1956, 24, 966. (b) R. A. Marcus, *Annu. Rev. Phys. Chem.* 1964, 15, 155. (c) Marcus, R. A. *J. Phys. Chem.* 1968, 72, 891. For alternative models, see also: (d) Evans, M. G.; Polanyi, M. *Trans. Faraday Soc.* 1938, 34, 11. (e) G. W. Koeppl, A. J. Kresge, *J. Chem. Soc. Chem. Commun.* 1973, 371.

[21] For the application of Marcus theory toward radical reactions, see: a) ref 5b. b) I. V. Alabugin; M. Manoharan, *J. Am. Chem. Soc.* 2005, 127, 12583. c) I. V. Alabugin, M. Manoharan, *J. Am. Chem. Soc.* 2005, 127, 9534. For potential caveats, see: S. Osuna; K. N. Houk, *Chem. Eur. J.* 2009, 15, 13219.

[22] (a) Wille, U.; Plath, C. *Liebigs Ann./Recl.* 1997, 111. (b) Jargstorff, C.; Wille, U. *Eur. J. Org. Chem.* 2003, 3173. (c) Wille, U. *Org. Lett.* 2000, 2, 3485.

[23] (a) Wille, U. *J. Am. Chem. Soc.* 2002, 124, 14. (b) Tan, K. J.; White, J. M.; Wille, U. *Eur. J. Org. Chem.* 2010, 4902.

[24] Alabugin, I. V.; Gilmore, K.; Peterson, P. *WIREs Comput. Mol. Sci.* 2011, 1, 109.

[25] Alabugin, I. V.; Manoharan, M.; Zeidan, T. A. *J. Am. Chem. Soc.* 2003, 125, 14014.

SUMMARY OF THE INVENTION

Chemoselective interaction of aromatic enynes with radicals derived from stannanes, e.g., radicals derived from tin hydrides, such as $Bu_3Sn$ radicals, can be harnessed for selective cascade transformations yielding Sn-substituted naphthalene derivatives or Sn-substituted indene derivatives. Depending on the substitution at the alkene terminus, the initial regioselective 5-exo-trig cyclizations can be intercepted at the 5-exo stage either via hydrogen atom abstraction (HAA) or C—S bond scission, or allowed to proceed further to the formal 6-endo products via homoallylic ring expansion. Aromatization of the latter occurs via β-C—C bond scission which is facilitated by 2c,3e-Through-Bond (TB) interactions, a new stereoelectronic effect in radical chemistry. The combination of formal 6-endo-trig cyclization with stereoelectronically optimized fragmentation allows the use of alkenes as synthetic equivalents of alkynes and opens a convenient route to α-Sn-substituted naphthalene derivatives, a unique launching platform for the preparation of extended polyaromatics.

The present invention is directed to a method of synthesizing a Sn-functionalized aromatic compound comprising a fused aromatic ring system, the method comprising contacting a stannane compound and a reactant compound having the following structure (I):

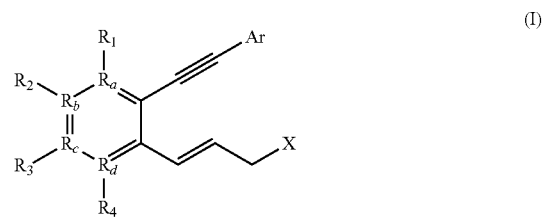

wherein:
each of $R_a$, $R_b$, $R_c$, and $R_d$ are independently carbon or nitrogen;
each $R_1$ $R_2$, $R_3$, and $R_4$ independently comprises hydrogen, halogen, cyano, amino, alkyl, alkoxy, alkenyl, alkynyl, aryl, or any two adjacent $R_1$ $R_2$, $R_3$, and $R_4$ together form a fused aromatic ring system;
X is selected from the group consisting of hydroxyl, alkyl, alkoxy, cycloalkyl, heterocyclic, amino, aryl, heteroaryl, and benzyl; and
Ar comprises aryl or heteroaryl, which may be unsubstituted or substituted.

In some embodiments, each of $R_a$, $R_b$, $R_c$, and $R_d$ are carbon; each $R_1$ $R_2$, $R_3$, and $R_4$ independently comprises hydrogen, alkenyl, alkynyl, aryl, or any two adjacent $R_1$ $R_2$, $R_3$, and $R_4$ together form a fused aromatic ring system; X is selected from the group consisting of hydroxyl, alkoxy, amino, phenyl, and benzyl; and Ar comprises aryl or heteroaryl, which may be unsubstituted or substituted.

The reactant compound above may be referred to as an enyne unit. In some embodiments, the Ar may be substituted with a substituted phenyl, additionally comprising an alkene and alkyne. Stated another way, the Ar moiety may comprise another enyne unit.

Other objects and features will be in part apparent and in part pointed out hereinafter.

BRIEF DESCRIPTION OF THE SEVERAL VIEWS OF THE DRAWINGS

FIG. 3A (Left) illustrates that efficiency of fragmentation can be increased by proper substitution at the alkene terminus. FIG. 3B (Middle) illustrates that 2-Center, 3-electron interactions are stabilizing "half-bonds" that account for radical stabilization energies in heteroatom-substituted radicals (at UM062X/LanL2DZ level).

FIGS. 13A and 13B depict the wide variety of naphthalene derivatives (FIG. 13B) that may be synthesized from the enyne reactants (FIG. 13A) according to the method of the present invention.

DETAILED DESCRIPTION OF THE EMBODIMENT(S) OF THE INVENTION

Figure 1:
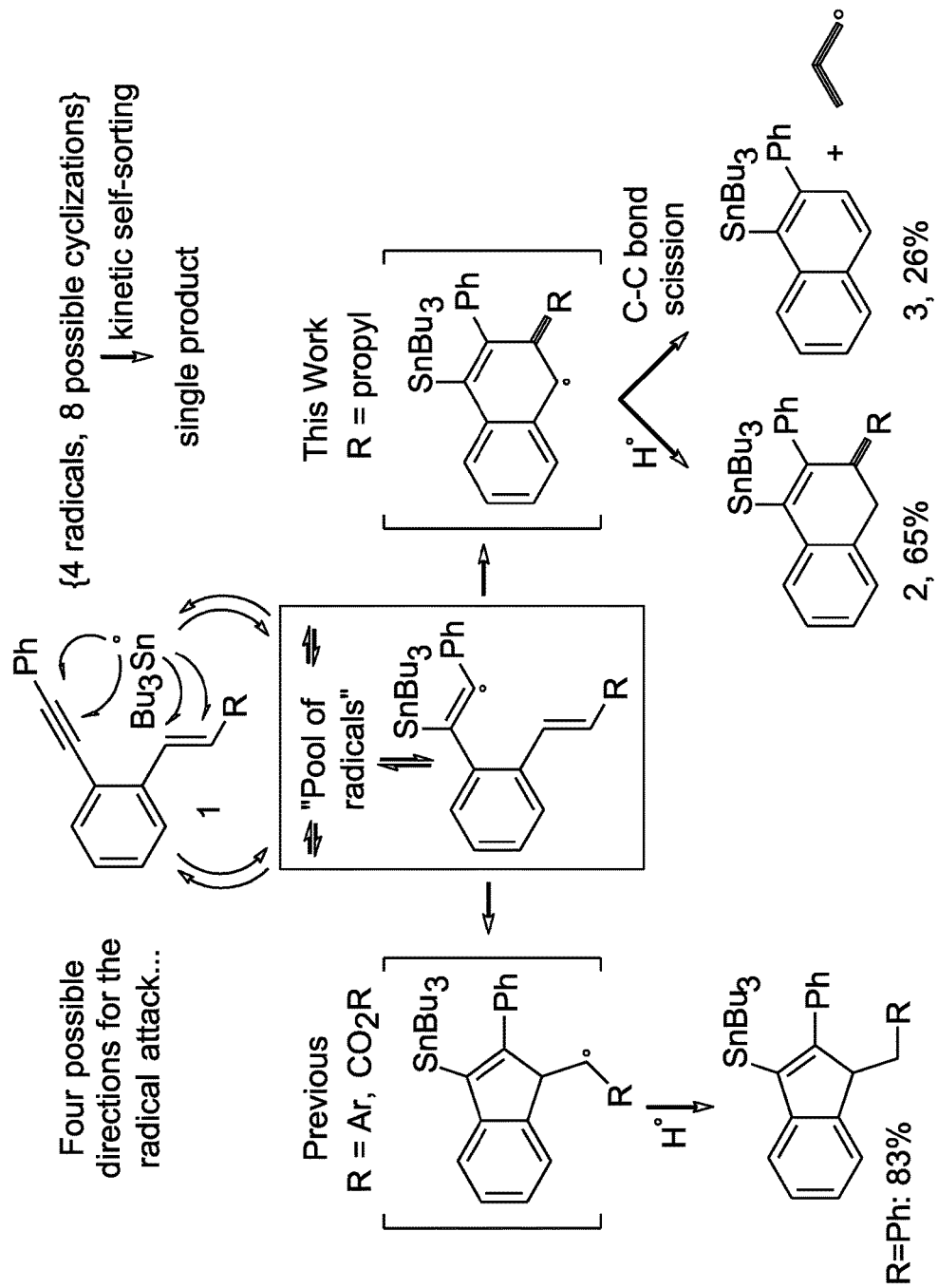
FIG. 1 is a depiction of kinetic self-sorting of the pool of equilibrating radicals and change in reaction path upon alkene substitution.

While investigating the scope of enyne cyclizations, we observed that alkyl substitution at the alkene changes the regioselectivity of the cyclization, directing the formation of a 6-endo product 2 in 65% yield. See FIG. 1, which is a depiction of kinetic self-sorting of the pool of equilibrating radicals and change in reaction path upon alkene substitution. This process does not provide a conjugated product because it is terminated by hydrogen atom abstraction.

Figure 2:
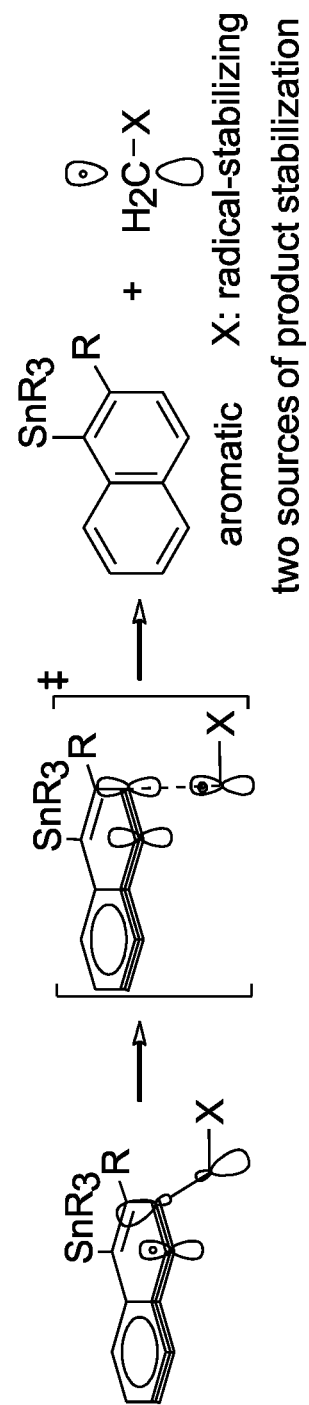
FIG. 2 is a depiction of C—C bond homolysis facilitated by product stabilization.

However, we also observed a small amount of naphthalene byproduct 3, aromatized by the loss of an alkyl group. See FIG. 1. Inspired by the observation that such β-scission of a C—C bond presents a viable alternative to H-atom abstraction as the final step, we envisaged a route to aromatic products in which the alkene moiety potentially serves as a synthetic alkyne equivalent. See FIG. 2. If this cyclization cascade can be efficiently extended by incorporating the fragmentation step, this route leads to aromatization without an external oxidizing agent or radical. We tested the possibility of promoting this minor reaction path via the rational design of radical leaving groups.

The feasibility of the fragmentation pathway is largely rationalized by the aromatic stabilization gained in the conversion of the initial 6-endo-trig products into naphthalene derivatives. The fragmentation is further enhanced by stabilizing the departing radical fragment via the rational design of radical leaving groups (LG). A balance between stability and reactivity is crucial because the reactivity of radicals formed in fragmentations dictates the outcome of the competition between propagation and termination of radical cascades. In particular, reactive radicals can react further in an undesirable way. We aimed to design the cascade such that the balance between stability and reactivity is struck, resulting in the sole formation of naphthalene derivatives. We found that this is possible upon altering the alkene substituent to $CH_2XCH_3$, where X=O or NMe. See FIGS. 3A, 3B, and 3C.

Figures 3A, 3B, 3C:
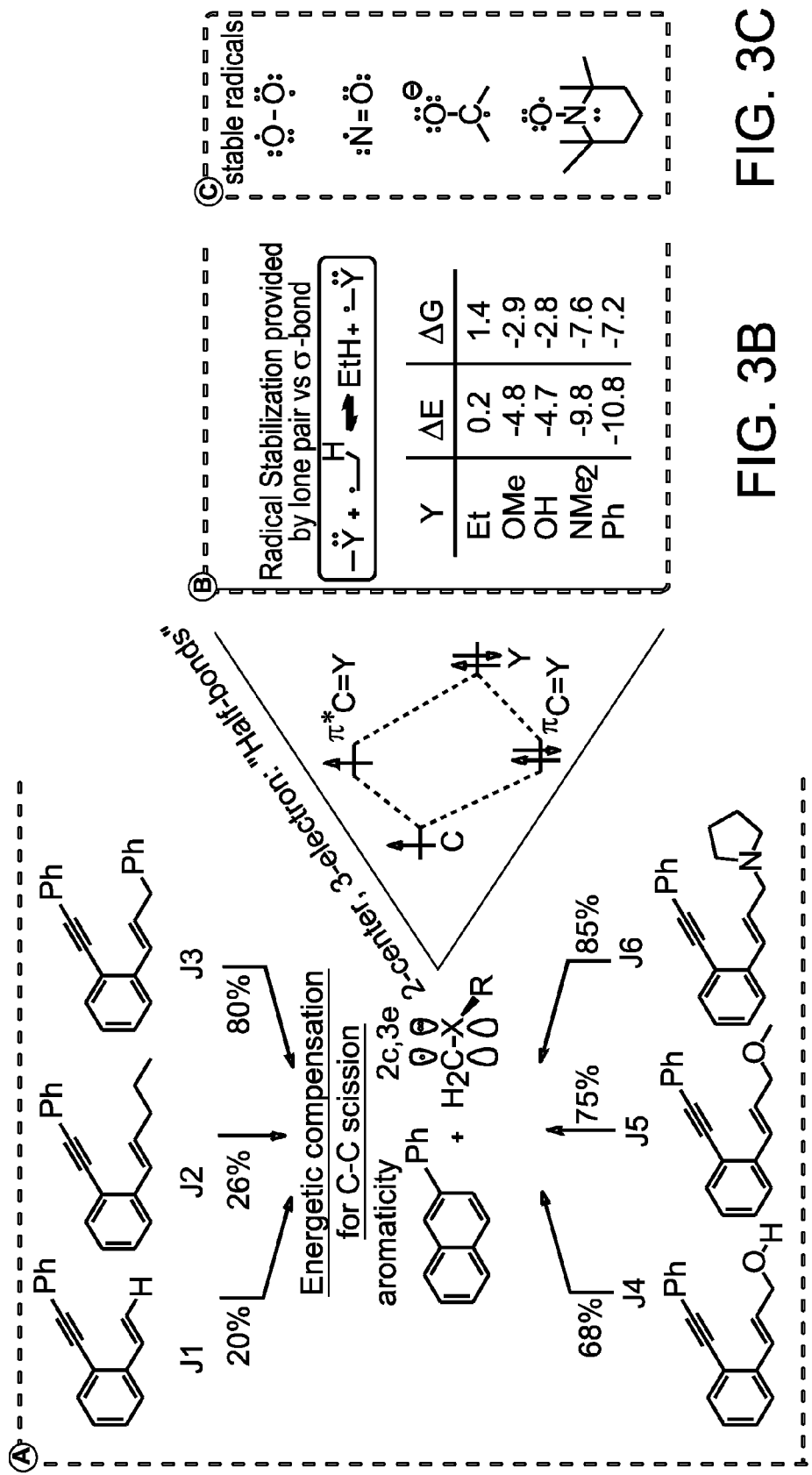
FIGS. 3A through 3B depict reaction cascades according to the present invention.
FIG. 3C (Right) illustrates molecules stabilized by 2c-3e bonds.

2-Center, 3-electron (2c-3e) delocalization between the alkyl radical center and lone pair of the adjacent heteroatom serves to stabilize the radical leaving group effectively allowing the cascade to "self-terminate." This term was introduced by Wille et al. to describe transformations where stable fragmenting radicals "exit" the reaction without exhibiting subsequent reactivity. See References 22 and 23. Such 2c-3e interactions correspond to the formal bond order of ½ and can be referred to as "half-bonds." Their presence accounts for the observed increase in the yield of naphthalene derivatives from enynes incorporating this rational design. FIG. 3A shows substrates containing either Ph or a heteroatom at the pendant alkene. For both substitution patterns, the fragmentation/aromatization proceeds fully because both the Ph group and the lone pairs are better radical stabilizing substituents than C—H/C—C bonds. See Reference 24. Furthermore, the higher product yield for X=N relative to X=O is consistent with nitrogen being a better donor than oxygen. See Reference 25. As expected, an increase in the experimental yields correlates with greater reaction exergonicity: $CH_2NMe_2$>$CH_2OMe$/$CH_2OH$>$CH_2Alkyl$. See FIGS. 3A and 3B. Elimination of a benzylic radical (R=$CH_2Ph$) is also a viable, albeit less atom-economical, option.

Accordingly, the present invention is directed to a method of synthesizing compounds comprising fused aromatic ring systems. Stated another way, in some embodiments, the method of the present invention involves a cyclization reaction of a starting material comprising an aromatic ring, e.g., a benzene ring, substituted with an alkene and an alkyne. The alkene further comprises a rationally designed radical leaving group which is eliminated from the product via C—C bond scission. This last step aromatizes the product without the need for external oxidant. The use of rationally designed alkenes successfully overcomes restrictions which had previously inhibited formal access to a synthetically valuable cyclization mode. This selective radical transformation opens a new approach for the controlled transformation of enynes into extended polycyclic structures of tunable dimensions.

I. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds.

As used in the specification and the appended claims, unless specified to the contrary, the following terms have the meaning indicated:

The term "alkyl", as used herein, means a straight or branched, saturated hydrocarbon chain containing from 1 to 12 carbon atoms, such as from 1 to 10 carbon atoms, such as from 1 to 8 carbon atoms, or from 1 to 6 carbon atoms. In some embodiments, an alkyl comprises a straight or branched, saturated hydrocarbon chain containing from 1 to 6 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 1 to 6 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylpentyl, 2,2-dimethylbutyl, 2-methylhexyl, 3-methylhexyl, 2,2-dimethylpentyl, 2,3-dimethylpentyl, n-heptyl, n-octyl, 2-methylheptyl, 3-methylheptyl, 2,3-dimethylheptyl, isooctyl, n-nonyl, and n-decyl, n-undecyl, n-dodecyl, etc.

The term "alkylene", as used herein, means a divalent group derived from a straight or branched, saturated hydrocarbon chain of 1 to 10 carbon atoms, for example, of 1 to 8 carbon atoms, or of 1 to 6 carbon atoms. The term "$C_1$-$C_6$ alkylenyl", as used herein, means a divalent group derived from a straight or branched, saturated hydrocarbon chain of 1 to 6 carbon atoms. Examples of an alkylene include, but are not limited to, —$CH_2$—, —$C(H)(CH_3)$—, —$CH_2CH_2$—, —$CH_2CH_2CH_2$—, —$CH_2CH(CH_3)$—, —$CH_2CH_2CH_2CH_2$—, —$CH_2CH(CH_3)CH_2$—, and —$CH_2C(CH_3)_2CH_2$—.

The term "alkenyl", as used herein, means a straight or branched hydrocarbon chain containing from 2 to 10 carbons and containing at least one carbon-carbon double bond. In some embodiments, alkenyl may comprise a straight or branched hydrocarbon chain containing from 2 to 6 carbons and containing at least one carbon-carbon double bond. The term "$C_2$-$C_4$ alkenyl" means an alkenyl group containing 2-4 carbon atoms. Non-limiting examples of alkenyls include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl. An alkenyl group may be unsubstituted, or it may be substituted with hydroxyl, alkyl, alkoxy, cycloalkyl, heterocyclic, amino, aryl, heteroaryl, and benzyl.

The term "alkenylene", as used herein, means a divalent group derived from a straight or branched chain hydrocarbon of 2 to 4 carbon atoms and contains at least one carbon-carbon double. Representative examples of alkenylene include, but are not limited to, —CH=CH— and —$CH_2$CH=CH—.

The term "alkynyl", as used herein, means a straight or branched chain hydrocarbon group containing from 2 to 10 carbon atoms and containing at least one carbon-carbon triple bond. The term "$C_2$-$C_4$ alkynyl", as used herein, means an alkynyl group containing from 2 to 4 carbon atoms. Representative examples of alkynyl include, but are not limited to, acetylenyl, 1-propynyl, 2-propynyl, 3-butynyl, 2-pentynyl, 1-butynyl, and 2-butynyl. An alkynyl group may be unsubstituted or it may be substituted with aryl or heteroaryl.

The term "alkoxy", as used herein, means a straight or branched, saturated hydrocarbon chain containing from 1 to 12 carbon atoms, such as from 1 to 6 carbon atoms and —O— terminating the hydrocarbon chain. The term "$C_x$-$C_y$ alkoxy," as used herein, means a straight or branched chain, saturated hydrocarbon containing x to y carbon atoms and —O— terminating the hydrocarbon chain. For example "$C_1$-$C_6$ alkoxy" means a straight or branched chain, saturated hydrocarbon containing 1 to 6 carbon atoms and —O— terminating the hydrocarbon chain. Examples of an alkoxy include, but are not limited to, methoxy, ethoxy, n-propoxy, iso-propoxy, n-butoxy, sec-butoxy, iso-butoxy, tert-butoxy, n-pentoxy, isopentoxy, neopentoxy, n-hexoxy, 2-methylpentoxy, and 2,2-dimethylbutoxy.

In the context of the present specification, unless otherwise stated, a hydroxyalkyl substituent group or a hydroxyalkyl moiety in a substituent group may be linear or branched. Examples of $C_{1-6}$ hydroxyalkyl groups/moieties include methyl, ethyl, n-propyl, isopropyl, n-butyl, iso-butyl, tert-butyl, n-pentyl, n-hexyl, etc, each of which comprises at least one hydroxyl group substituent in place of a hydrogen.

In the context of the present specification, "amine" or "amino" encompasses all primary (one alkyl group), secondary (two alkyl groups), tertiary (three alkyl groups), or quaternary amine (four alkyl groups). The alkyl groups are defined as above. Exemplary amines include tetramethylammonium, tetraethylammonium, methylamine, dimethylamine, trimethylamine, triethylamine, diethylamine, ethylamine and the like. Other representative organic amines include ethylenediamine, ethanolamine, diethanolamine, piperidine, piperazine and the like.

In the context of the present invention, aryl or aromatic encompasses aromatic rings, which may be fused or unfused to other aromatic or cycloalkyl rings. Aryl or aromatic encompasses aromatic rings (i.e., comprising carbon and hydrogen). Aryl may comprise from 3 to 24 carbon atoms, such as from 6 to 24 carbon atoms. Examples of aryl include benzene, naphthalene, acenaphthene, anthracene, benz[a]anthracene, benzo[a]pyrene, benzo[e]pyrene, chrysene, indeno(1,2,3-cd)pyrene, phenanthrene, pyrene, coronene, fluorene, and the like.

The term "aryl", as used herein, means a phenyl or a bicyclic aryl. The bicyclic aryl may be naphthyl, or a phenyl fused to a monocyclic cycloalkyl, or a phenyl fused to a monocyclic cycloalkenyl. Non-limiting examples of the aryl groups include phenyl, dihydroindenyl (e.g. 2,3-dihydro-1H-inden-1-yl), indenyl, naphthyl, dihydronaphthalenyl, and tetrahydronaphthalenyl (e.g. 1,2,3,4-tetrahydronaphthalen-1-yl). The aryl groups can be unsubstituted or substituted, e.g., with alkyl, halo, haloalkyl, alkoxy, cyano, heterocyclo, etc., and the bicyclic aryl is attached to the parent molecular moiety through any substitutable carbon atom contained within the bicyclic ring system.

The term "cycloalkyl" or "cycloalkane", as used herein, means a monocyclic or a bicyclic ring system. The term "monocyclic cycloalkyl", as used herein, is a carbocyclic ring system containing three to eight carbon atoms, such as three to six carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic or bicyclic cycloalkyl ring may contain one or two alkylene bridges, each consisting of one, two, three, or four carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, e.g., with alkyl, halo, haloalkyl, alkoxy, cyano, heterocyclo, etc., and are attached to the parent molecular moiety through any substitutable atom contained within the ring system.

The term "cycloalkenyl" or "cycloalkene", as used herein, means a monocyclic or a bicyclic hydrocarbon ring system. The monocyclic cycloalkenyl has four, five, six, seven, eight, nine, or ten carbon atoms, e.g., $C_4$-$C_{10}$, or $C_5$-$C_{10}$ cycloalkenyl, and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, cyclooctenyl, cyclononenyl, cyclodecenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be unsubstituted or substituted, e.g., with alkyl, halo, haloalkyl, alkoxy, cyano, heterocyclo, etc., and are attached to the parent molecular moiety through any substitutable atom contained within the ring systems, and can be unsubstituted or substituted.

The term "halo" or "halogen" or "halide", as used herein, means Cl, Br, I, or F.

The term "haloalkyl", as used herein, means an alkyl group, as defined herein, in which one, two, three, four, five or six hydrogen atoms are replaced by halogen. The term "$C_1$-$C_6$ haloalkyl", as used herein, means a $C_1$-$C_6$ alkyl group, as defined herein, in which one, two, three, four, five, or six hydrogen atoms are replaced by halogen. The term "$C_1$-$C_4$ haloalkyl", as used herein, means a $C_1$-$C_4$ alkyl group, as defined herein, in which one, two, three, four, five, or six hydrogen atoms are replaced by halogen. Representative examples of haloalkyl include, but are not limited to, chloromethyl, fluoromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloaryl", as used herein, means a phenyl or bicyclic aryl in which one, two, three, four, five, six, seven, or eight hydrogen atoms are replaced by halogen. Non-limiting examples of the aryl groups include fluorophenyl, chlorophenyl, bromophenyl, iodophenyl, fluoro-, chloro-, bromo-, or iodo-dihydroindenyl (e.g. 2,3-dihydro-1H-inden-1-yl), fluoro-, chloro-, bromo-, or iodo-indenyl, fluoro-, chloro-, bromo-, or iodo-naphthyl, fluoro-, chloro-, bromo-, or iodo-dihydronaphthalenyl, and fluoro-, chloro-, bromo-, or iodo-tetrahydronaphthalenyl (e.g. 1,2,3,4-tetrahydronaphthalen-1-yl).

The term "heterocycle" or "heterocyclic", as used herein, means a monocyclic heterocycle or a bicyclic heterocycle. The monocyclic heterocycle, as used herein, is a three-, four-, five-, six-, seven-, eight-, nine-, or ten-membered ring containing at least one heteroatom independently selected from the group consisting of O, N, and S. The three-, four-, five-, six-, seven-, eight-, nine-, or ten-membered ring contains zero or one double bond, and one heteroatom selected from the group consisting of O, N, and S. The four-, five-, six-, seven-, eight-, nine-, or ten-membered heterocyclic ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle, as used herein, is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include e.g. dihydrochromenyl (e.g. 3,4-dihydro-2H-chromen-4-yl), benzopyranyl, benzothiopyranyl, 2,3-dihydrobenzofuranyl, 2,3-dihydrobenzothienyl, and 2,3-dihydro-1H-indolyl. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). In some embodiments, a 4- to 10-membered ring heterocyclyl may be selected from among 2,3-dihydrofuranyl, 2,5-dihydrofuranyl, tetrahydrofuranyl, 1,3-dioxolanyl, 1,3-dioxanyl, tetrahydro-2H-pyranyl, 3,4-dihydro-2H-pyranyl, 3,6-dihydro-2H-pyranyl, 2H-pyranyl, 4H-pyranyl, pyrrolidinyl, 2,3-dihydro-1H-pyrrolyl, 2,5-dihydro-1H-pyrrolyl, 4H-1,3-dioxinyl, 1,4-dioxanyl, 2,3-dihydro-1,4-dioxinyl, piperidinyl, 2-oxa-7-azaspiro[3.5]nonanyl, 1,2-dihydropyridinyl, 1,4-dihydropyridinyl, 2,3-dihydropyridinyl, 3,4-dihydropyridinyl, 1,2,3,6-tetrahydropyridinyl, isoxazolidinyl, oxazolidinyl, 2,3-dihydroisoxazolyl, 2,5-dihydroisoxazolyl, and morpholino, each of which may be substituted or unsubstituted. The monocyclic and the bicyclic heterocycles can be unsubstituted or substituted, e.g., with alkyl, halo, haloalkyl, alkoxy, cyano, heterocyclo, cycloalkyl, sulfonyl, etc., and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized.

The term "heteroaryl", as used herein, means a monocyclic heteroaryl or a bicyclic heteroaryl. The heteroaryl may comprise 5- to 10-membered ring. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-5H-cyclopenta[b]pyridinyl (e.g. 6,7-dihydro-5H-cyclopenta[b]pyridin-7-yl), 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolinyl (e.g. 5,6,7,8-tetrahydroquinolin-5-yl, 5,6,7,8-tetrahydroquinolin-8-yl). In some embodiments, 5- to 10-membered ring heteroaryl may be selected from among pyridinyl, pyrimidinyl, pyrazinyl, 1H-indolyl, 2H-indolyl, pyrazolyl, 1H-imidazolyl, oxazolyl, isoxazolyl, pyrazolyl, quinolinyl, isoquinolinyl, furo[3,2-b]pyridinyl, furo[4,3-b]pyridinyl, furo[5,4-b]pyridinyl, and benzo[c][1,2,5]oxadiazol-5-yl, each of which may be substituted or unsubstituted. The monocyclic and bicyclic heteroaryl groups can be substituted, e.g., with alkyl, halo, haloalkyl, alkoxy, cyano, heterocyclo, cycloalkyl, sulfonyl, etc., or unsubstituted and are connected to the parent molecular moiety through any substitutable carbon atom or any substitutable nitrogen atom contained within the ring systems.

The term "heteroatom", as used herein, means a nitrogen, oxygen, or sulfur atom.

The term "oxo", as used herein, means a =O group.

The term "carbonyl", as used herein, means a

group. A "carbonyl" group may alternatively be disclosed as —C(O)—.

The term "carboxy" or "carboxyl", as used herein, means a

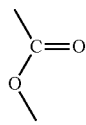

group. A "carboxy" or "carboxyl" group may alternatively be disclosed as —C(O)O—.

The term "hydroxy" or "hydroxyl", as used herein, means a —OH group. In some embodiments, a hydroxy or hydroxyl group may be bonded to an alkyl thereby forming an hydroxyalkyl, such as, but not limited to hydroxymethyl, hydroxyethyl, etc.

The term "cyano", as used herein, means a —C≡N group.

The term "imino", as used herein, means a

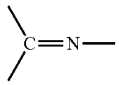

group. The imino may be bonded to one, two, or three groups, such as, but not limited to, alkyl, hydroxyl, alkoxy.

The term "thio", as used herein, means a group comprising a —S— group.

The term "sulfonyl", as used herein, means a group comprising a

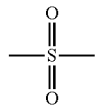

group.

The term "phosphate", as used herein, means a —PO$_3$H$_2$ group. One or both hydrogens in a phosphate may be replaced with cations, such as sodium or potassium.

II. Synthesis

In some embodiments, the method of the present invention is directed to the synthesis of a polycyclic aromatic compound, e.g., a naphthalene derivative. In some embodiments, the method of the present invention is directed to synthesizing a Sn-functionalized aromatic compound comprising a fused aromatic ring system. The Sn-functionalized aromatic compound may be contacted with acid to thereby remove the Sn-moiety and prepare a substituted naphthalene compound. Alternatively, the Sn-functionalized aromatic compound comprising a fused aromatic ring system may be contacted with other organic compounds to incorporate further functionality onto the fused aromatic ring system.

According to some embodiments, the method comprises contacting a stannane compound, e.g., a tin hydride, and a reactant compound having the following structure (I):

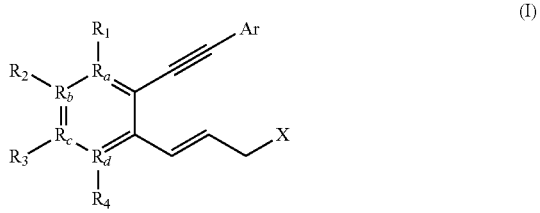

In some embodiments, the reaction mixture further comprises a radical initiator. In some embodiments, the reaction may occur in a solvent, such as an aprotic solvent. Accordingly, in some embodiments, the reaction mixture comprises a compound having the structure (I), a stannane compound, and a radical initiator. Contact of these components may occur in a solvent, such as an aprotic solvent.

In some embodiments, each of $R_a$, $R_b$, $R_c$, and $R_d$ are independently carbon or nitrogen. In some embodiments, each of $R_a$, $R_b$, $R_c$, and $R_d$ are carbon. In some embodiments, at least two of $R_a$, $R_b$, $R_c$, and $R_d$ are carbon, and the remainder are nitrogen. In some embodiments, three of $R_a$, $R_b$, $R_c$, and $R_d$ are carbon, and one is nitrogen.

In some embodiments, each $R_1$ $R_2$, $R_3$, and $R_4$ independently comprises hydrogen, halogen, cyano, amino, alkyl, alkoxy, alkenyl, alkynyl, aryl, or any two adjacent $R_1$ $R_2$, $R_3$, and $R_4$ together form a fused aromatic ring system. In some embodiments, each $R_1$ $R_2$, $R_3$, and $R_4$ independently comprises hydrogen, alkenyl, alkynyl, aryl, or any two adjacent $R_1$ $R_2$, $R_3$, and $R_4$ together form a fused aromatic ring system.

In some embodiments, the X is selected from the group consisting of hydroxyl, alkyl, alkoxy, cycloalkyl, heterocyclic, amino, aryl, heteroaryl, and benzyl. In some embodiments, the X moiety is selected from the group consisting of hydroxyl, alkoxy, amino, and phenyl. In some embodiments, the X moiety may be unsubstituted, such as hydroxyl or amine ($NH_2$). In some embodiments, the X moiety may comprise a substituted alkoxy, a substituted amino, or a substituted phenyl. Suitable substituents include aryl, alkyl, halo, and amino.

In the above compound having structure (I), Ar comprises aryl or heteroaryl, which may be unsubstituted or substituted. Suitable substituents include alkyl, alkenyl, alkynyl, halo, cyano, carbonyl, alkoxy, aryl (e.g., an additional ring or a fused aromatic ring), among others. In some embodiments, the Ar group is substituted with reactive alkene moieties and reactive alkyne moieties.

In some embodiments, the reactant compound has the following structure (I)-a:

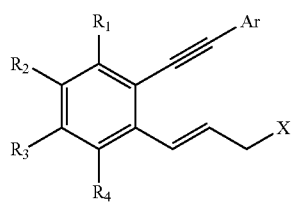

(I)-a wherein each of $R_1$, $R_2$, $R_3$, $R_4$, X, and Ar are as defined above in connection with structure (I).

In some embodiments of the compound of structure (I)-a, each of $R_1$, $R_2$, $R_3$, and $R_4$ independently comprises hydrogen, halogen, cyano, amino, alkyl, alkoxy, alkenyl, alkynyl, aryl, or any two adjacent $R_1$, $R_2$, $R_3$, and $R_4$ together form a fused aromatic ring system; X is selected from the group consisting of hydroxyl, alkyl, alkoxy, cycloalkyl, heterocyclic, amino, aryl, heteroaryl, and benzyl; and Ar comprises aryl or heteroaryl, which may be unsubstituted or substituted.

In some embodiments of the compound of structure (I)-a, each $R_1$, $R_2$, $R_3$, and $R_4$ independently comprises hydrogen, alkenyl, alkynyl, aryl, or any two adjacent $R_1$, $R_2$, $R_3$, and $R_4$ together form a fused aromatic ring system; X is selected from the group consisting of hydroxyl, alkoxy, amino, phenyl, and benzyl; and Ar comprises aryl or heteroaryl, which may be unsubstituted or substituted.

In some embodiments, the reactant compound has any of the following structures (I)-b, (I)-c, (I)-d, or (I)-e:

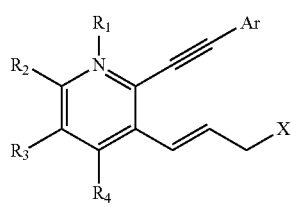

(I)-b

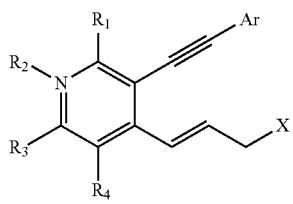

(I)-c

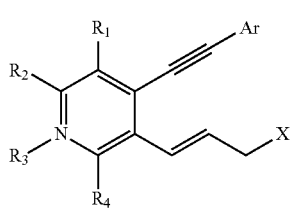

(I)-d

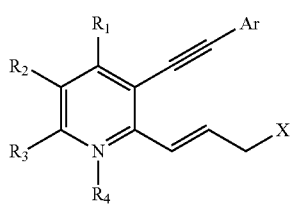

(I)-e wherein each of $R_1$, $R_2$, $R_3$, $R_4$, X, and Ar are as defined above in connection with structure (I).

In some embodiments of the compound of any of the structures (I)-b, (I)-c, (I)-d, or (I)-e, each of $R_1$, $R_2$, $R_3$, and $R_4$ independently comprises hydrogen, halogen, cyano, amino, alkyl, alkoxy, alkenyl, alkynyl, aryl, or any two adjacent $R_1$, $R_2$, $R_3$, and $R_4$ together form a fused aromatic ring system; X is selected from the group consisting of hydroxyl, alkyl, alkoxy, cycloalkyl, heterocyclic, amino, aryl, heteroaryl, and benzyl; and Ar comprises aryl or heteroaryl, which may be unsubstituted or substituted.

In some embodiments of the compound of any of the structures (I)-b, (I)-c, (I)-d, or (I)-e, each $R_1$, $R_2$, $R_3$, and $R_4$ independently comprises hydrogen, alkenyl, alkynyl, aryl, or any two adjacent $R_1$, $R_2$, $R_3$, and $R_4$ together form a fused aromatic ring system; X is selected from the group consisting of hydroxyl, alkoxy, amino, phenyl, and benzyl; and Ar comprises aryl or heteroaryl, which may be unsubstituted or substituted.

In some embodiments, the Ar group is substituted with reactive alkene moieties and reactive alkyne moieties. Still further configurations are possible, e.g., if the Ar group is substituted with reactive alkene and alkyne moieties. In some embodiments, the reactant compound may have the following structures (II)-a, (II)-b, (II)-c, or (II)-d:

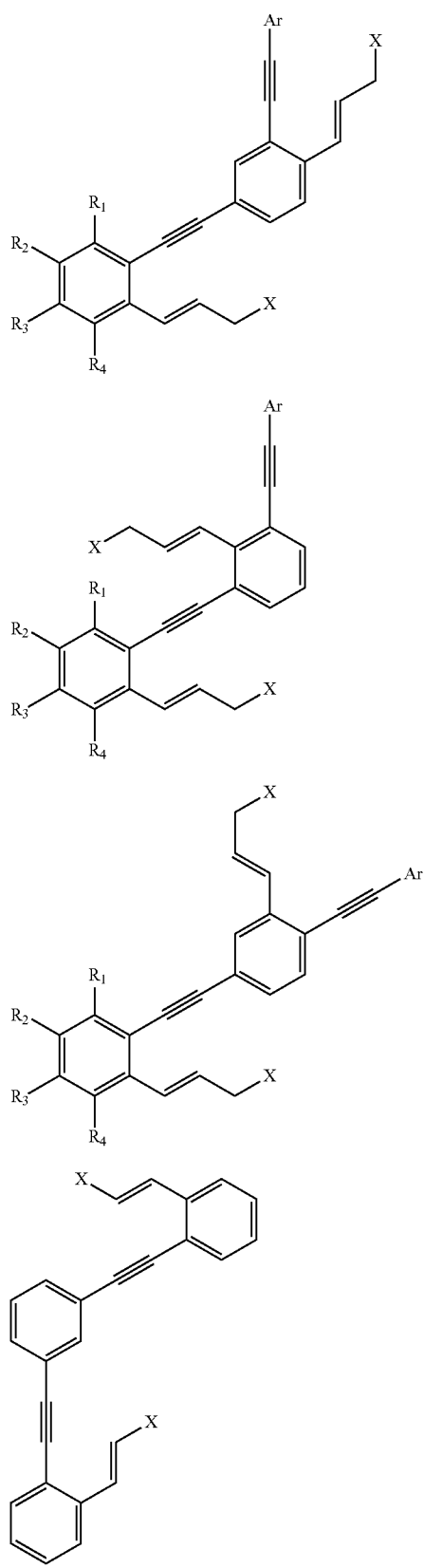

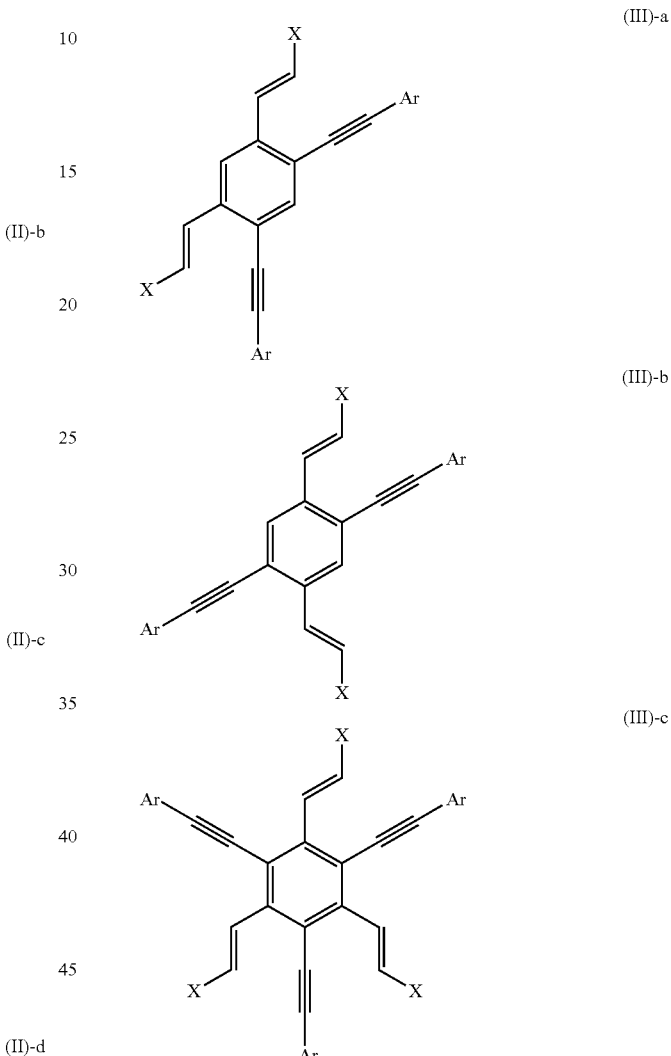

Each of the $R_1$, $R_2$, $R_3$, $R_4$, X, and Ar are as defined above in connection with structure (I). Such compounds are capable of preparing substituted naphthalene compounds linked by a bond or an intervening functional group.

Still further configurations are possible, such as the following compounds having structures (III)-a, (III)-b, and (III)-c in which a core benzene ring is substituted with two or three alkenyl moieties and two or three alkynyl moieties:

Each of the X and Ar are as defined above in connection with structure (I).

Still further examples of reactant compounds are provided in the Examples.

In some embodiments, the stannane compound, e.g., a tin hydride, has a general formula $X_3SnH$, wherein X is a $C_1$-$C_6$ alkyl or phenyl. In some embodiments, the stannane compound is selected from the group consisting of trimethyl stannane, triethyl stannane, tri(n-propyl) stannane, tri(iso-propyl) stannane, tri(n-butyl) stannane, tri(isobutyl) stannane, triphenyl stannane, and any combination there. The identity of X in structure (1-a) is determined primarily, if not wholly, by the stannane compound. In some preferred embodiments, the stannane compound is tri(n-butyl) stannane. In general, the stannane compound may be contacted with the reactant compound in relatively equivalent molar amounts, such as in a molar ratio of stannane compound to reactant compound between about 1:2 and about 3:1, such as between about 1:1 and about 2:1, such as about 1.2:1.

In some embodiments, the radical initiator is any compound that can provide radicals for the initiation step of a radical chain reaction. In some embodiments, the radical initiator is any compound that converts the stannane compound (generally, $X_3SnH$, wherein X is a $C_1$-$C_6$ alkyl or phenyl) into $X_3Sn$ radical. Suitable radical initiators include azo compounds, inorganic peroxides, or organic peroxides. In some embodiments, the radical initiator is Azobisisobutyronitrile (2,2'-azobis(2-methylpropionitrile), AIBN). In some embodiments, the radical initiator is 1,1'-Azobis(cyclohexanecarbonitrile) (ABCN). In some embodiments, the radical initiator is di-tert-butyl peroxide (TOOT, or DTBPB). In some embodiments, the radical initiator is benzoyl peroxide. The radical initiator may be added to the reaction mixture in less than molar equivalent amount of the radical initiator compared to the reactant compound, such as a molar ratio less than 1:1, or less than about 1:2 (i.e., about 0.5 molar equivalents per 1 molar reactant compound), or less than about 1:4.

The contact may occur in a solvent, suitably an aprotic solvent. Solvents suitable for the reaction of the present invention include benzene, diethyl ether, toluene, tetrahydrofuran, hexane, and dichloromethane. In some preferred embodiments, the solvent is toluene or benzene, with toluene being particularly preferred.

In some embodiments, contact between the reactant compound and the stannane compound yields a Sn-functionalized aromatic compound comprising a fused aromatic ring system having the following structure (IV)-a:

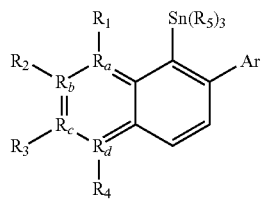

(IV)-a wherein each of $R_a$, $R_b$, $R_c$, $R_d$, $R_1$ through $R_4$ and Ar are as defined above in connection with Structure (I). Each $R_5$ independently comprises alkyl, aryl, or heteroaryl. Preferably, each $R_5$ independently comprises alkyl.

In some embodiments, contact between the reactant compound and the stannane compound yields a Sn-functionalized aromatic compound comprising a fused aromatic ring system having the following structure (IV)-b:

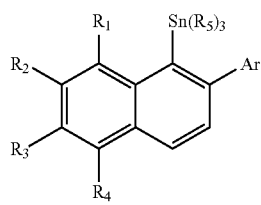

(IV)-b wherein $R_1$ through $R_4$ and Ar are as defined above. Each $R_5$ independently comprises alkyl, aryl, or heteroaryl. Preferably, each $R_5$ independently comprises alkyl.

According to some embodiments of the present invention, the Sn-functionalized aromatic compound comprising a fused aromatic ring system is further contacted with an acid to remove the Sn moiety. Contact with an acid thereby prepares a substituted naphthalene having the structure (V)-a:

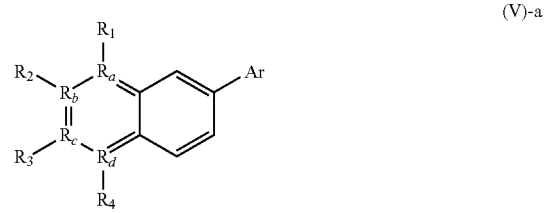

(V)-a wherein each of $R_a$, $R_b$, $R_c$, $R_d$, $R_1$ through $R_4$ and Ar are as defined above in connection with Structure (I). Suitable acids include any inorganic or mineral acid, such as hydrochloric acid, hydrofluoric acid, hydrobromic acid, hydroiodic acid, sulfuric acid, and the like.

According to some embodiments of the present invention, the Sn-functionalized aromatic compound comprising a fused aromatic ring system is further contacted with an acid to remove the Sn moiety. Contact with an acid thereby prepares a substituted naphthalene having the structure (V)-b:

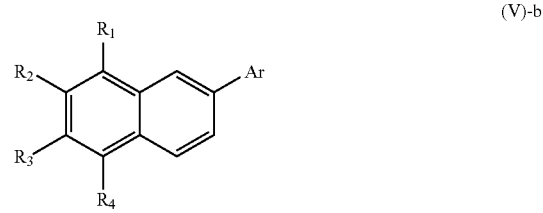

(V)-b $R_1$ through $R_4$ and Ar are as defined above. Suitable acids include any inorganic or mineral acid, such as hydrochloric acid, hydrofluoric acid, hydrobromic acid, hydroiodic acid, sulfuric acid, and the like.

Still further products may be prepared according to the present invention, as disclosed in the Examples.

According to some embodiments of the present invention, the Sn-functionalized aromatic compound comprising a fused aromatic ring system is subjected to further functionalization. Accordingly, in some embodiments, the Sn-functionalized aromatic compound may be contacted with organic precursor compounds sufficient to prepare a substituted naphthalene having the structure (VI)-a:

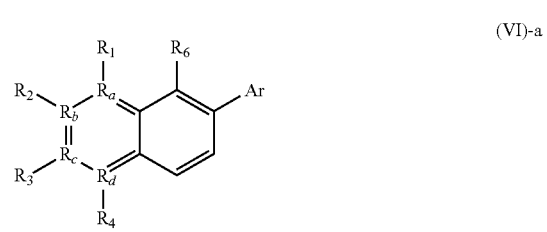

(VI)-a wherein each of $R_a$, $R_b$, $R_c$, $R_d$, $R_1$ through $R_4$ and Ar are as defined above in connection with Structure (I). $R_6$ is selected from the group consisting of alkyl, alkenyl, alkynyl, aryl, heteroaryl, amino, alkoxy, and halo.

According to some embodiments of the present invention, the Sn-functionalized aromatic compound comprising a fused aromatic ring system is subjected to further functionalization. Accordingly, in some embodiments, the Sn-functionalized aromatic compound may be contacted with organic precursor compounds sufficient to prepare a substituted naphthalene having the structure (VI)-b:

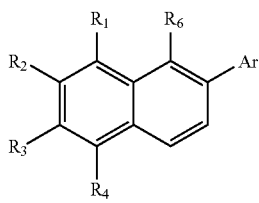

(VI)-b $R_1$ through $R_4$ and Ar are as defined above. $R_6$ is selected from the group consisting of alkyl, alkenyl, alkynyl, aryl, heteroaryl, amino, alkoxy, and halo.

In some embodiments, functionalization of products having structures (IV)-a and (IV)-b may be carried out by the Stille reaction in which the $Sn(R_5)_3$ group is replaced with an organic functionality by contacting the compound having structure (IV)-a or (IV)-b with an organic halide. The Stille reaction is catalyzed by a $Pd^0$ compound, such as tetrakis(triphenylphosphine) palladium(0). The Examples provide several reactions proceeding occurring to the Stille reaction.

In some embodiments, functionalization of products having structures (IV)-a and (IV)-b may be carried out by Sonogashira coupling in which the $Sn(R_5)_3$ group is replaced with a leaving group, such as iodo, bromo, chloro, or triflate. The Sonogashira coupling is catalyzed by a palladium catalyst and a copper catalyst. The Sonogashira coupling of the product compounds enables functionalization with an alkynyl compound. The Examples provide several reactions proceeding occurring to Sonogashira coupling.

In some embodiments, functionalization of products having structures (IV)-a and (IV)-b may be carried out by the Suzuki reaction in which the $Sn(R_5)_3$ group is replaced with a leaving group, such as iodo, bromo, chloro, or triflate. The Suzuki reaction is catalyzed by a palladium catalyst. The Suzuki reaction of the product compounds enables functionalization through single bonds. The Examples provide several reactions proceeding occurring to the Suzuki reaction.

III. Design of Radical Leaving Groups

In order to break unstrained C—C bonds under relatively mild conditions, both thermodynamics and kinetics of this process need to be optimized. See Reference 7. In the present example, the energetic penalty for the homolytic cleavage of a strong C—C bond is partially compensated by the aromatic stabilization gained in the product. However, the $2^{nd}$ product (the propyl radical) is a high energy, unstable species. We envisioned that stabilization of the alkyl radical would further promote the fragmentation. See FIG. 2 and FIGS. 3A, 3B, and 3C. In order to accelerate this reaction, this stabilization should develop early and become sufficiently large in the transition state (TS). See Reference 8.

Radical fragmentations provide a valuable option for the termination of cascade transformations. See Reference 9. The reactivity of radicals formed in the fragmentation step dictates the outcome of the competition between propagation and termination of radical cascades. Our design of stabilized radical leaving groups was guided by the electronic structure of super-stable radicals, i.e., molecular oxygen, nitric oxide, and TEMPO, where a half-filled orbital is stabilized by an adjacent lone pair. In the extreme, such strong 2-center, 3-electron (2c-3e) interactions correspond to the bond order of ½ and can be referred to as "half-bonds". Stabilization provided by the 2c-3e interactions depends on the relative electronegativity of the heteroatom.

Figure 4:
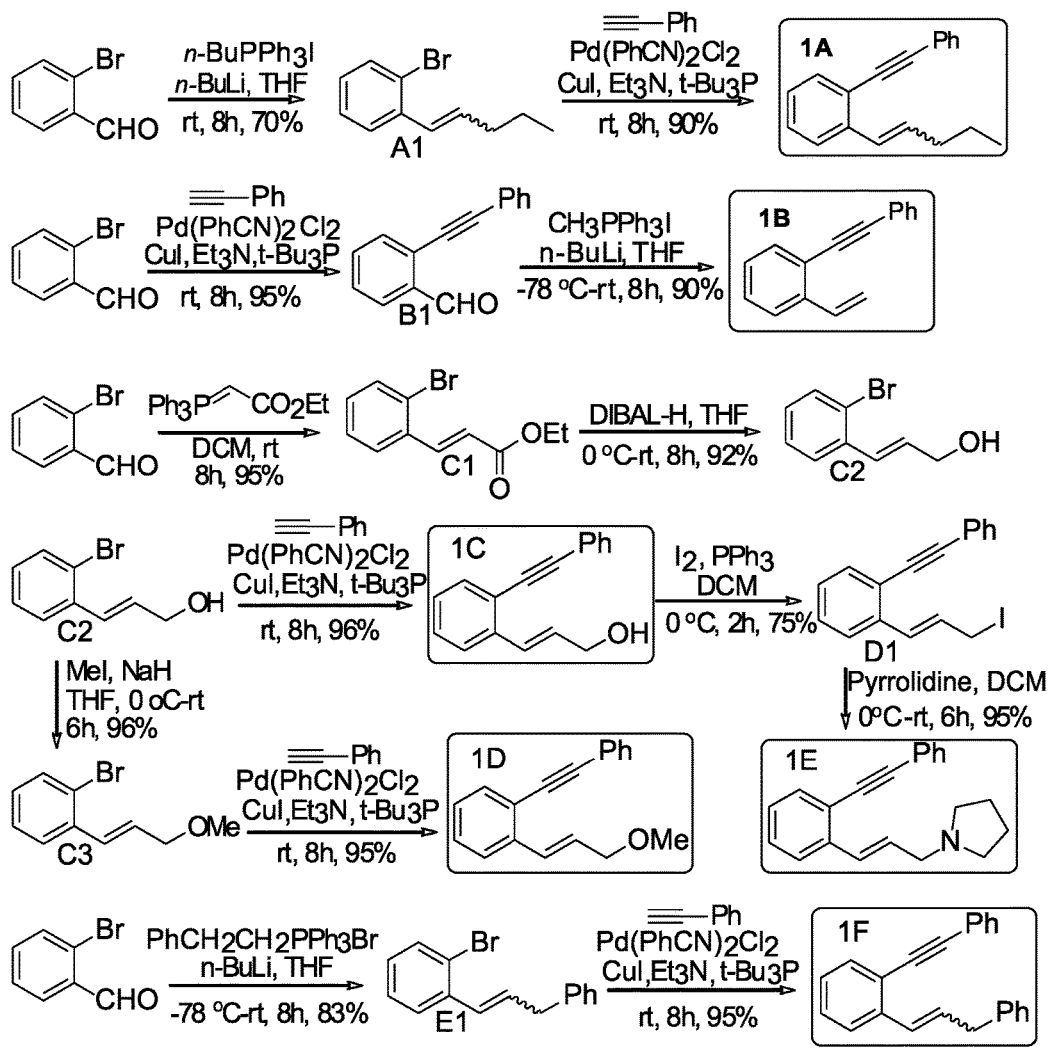
FIG. 4 depicts the synthesis of starting materials.

We expected that such strong stabilization via incorporation of heteroatoms adjacent to the radical center will increase the efficiency of the "self-terminating" fragmentation and also render the fragmented radical relatively inert, preventing undesirable side reactions. Allylic oxygen, nitrogen, and aromatic substituents can be easily incorporated at the ene terminus using well established C—C coupling procedures, affording the requisite set of substrates. See FIG. 4, which depicts the synthesis of starting materials.

Figure 5:
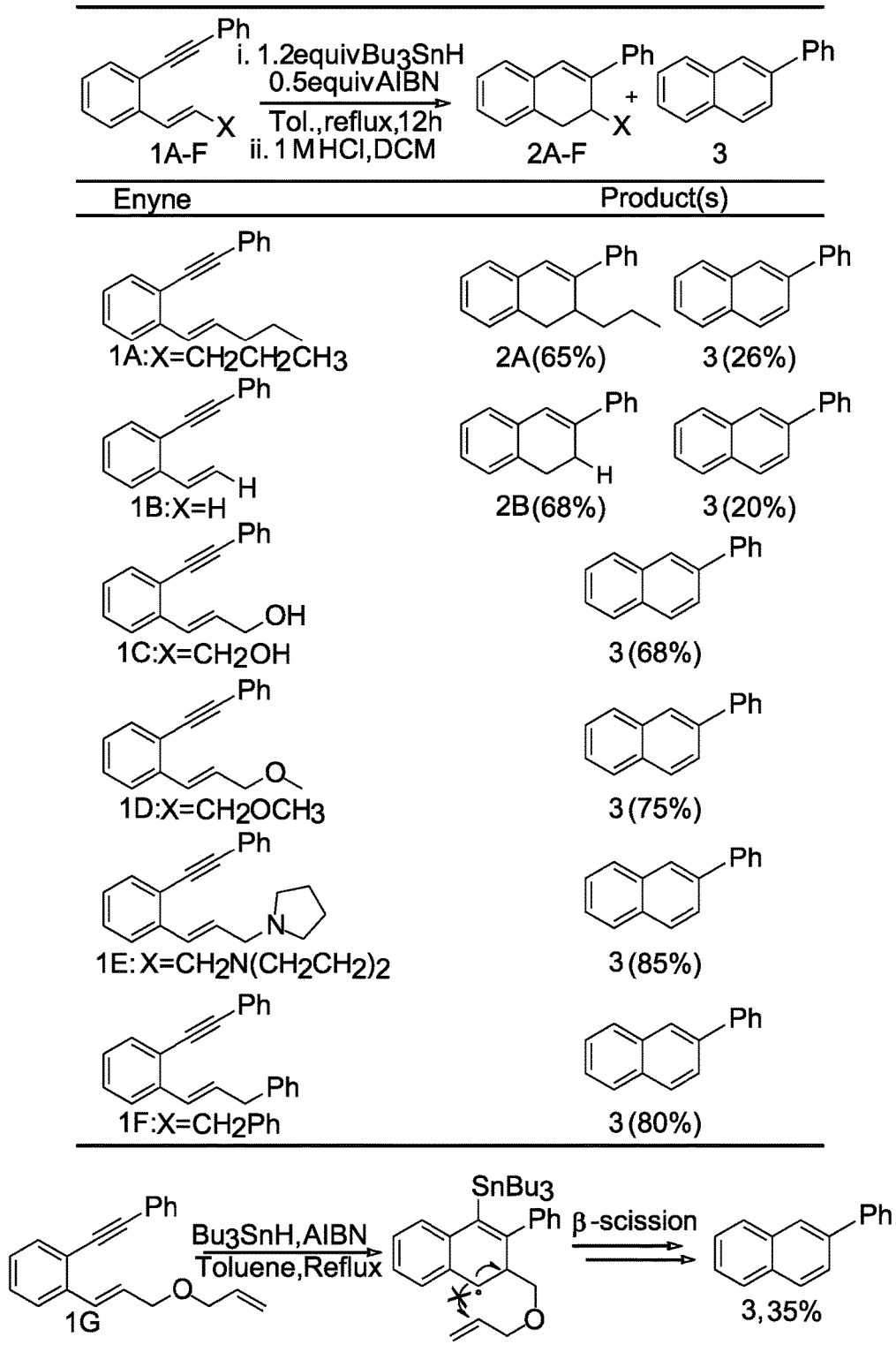
FIG. 5 depicts the reaction of H-abstraction to fragmentation promoted by 2c-3e bonds. The loss of $CH_2OR$ group successfully competes with 6-exo-cyclization.

To our delight, heteroatom incorporation completely switched the selectivity in favor of the "self-terminating" fragmentation. See FIG. 5, which depicts the reaction of H-abstraction to fragmentation promoted by 2c-3e bonds. The loss of $CH_2OR$ group successfully competes with 6-exo-cyclization. Furthermore, the fragmentation is sufficiently fast to compete with 6-exo-dig radical cyclization.

The "self-terminating" nature of the fragmentation is supported by the need to use stoichiometric amount of initiator (0.5 equiv. AIBN produces 1 equiv. of isobutyronitrile radical) for full conversion. See Table 1. While bond dissociation energies (BDE) suggest propagation via hydrogen abstraction by $.CH_2$—X from $Bu_3SnH$ to be a thermodynamically favorable process (H—$CH_2OH$, BDE=96 kcal/mol vs. $Bu_3Sn$—H, BDE=74 kcal/mol), kinetics of such a process may be relatively slow as both species are nucleophilic. See reference 11.

TABLE 1

Optimization of equivalents of AIBN.[a]

| $Bu_3SnH$ (equiv.) | AIBN (equiv.) | Time (h) | Yield[b] (%) | Unreacted SM[b] (%) |
|---|---|---|---|---|
| 1D 1.2 | 0.1 | 12 | 11 | 42 |
| 1D 1.2 | 0.2 | 12 | 31 | 19 |
| 1D 1.2 | 0.2 | 12 | 10[c] | 24 |
| 1D 1.2 | 0.4 | 12 | 65 | 9 |
| 1D 1.2 | 0.5 | 12 | 78 | 0 |

Figure 7A:
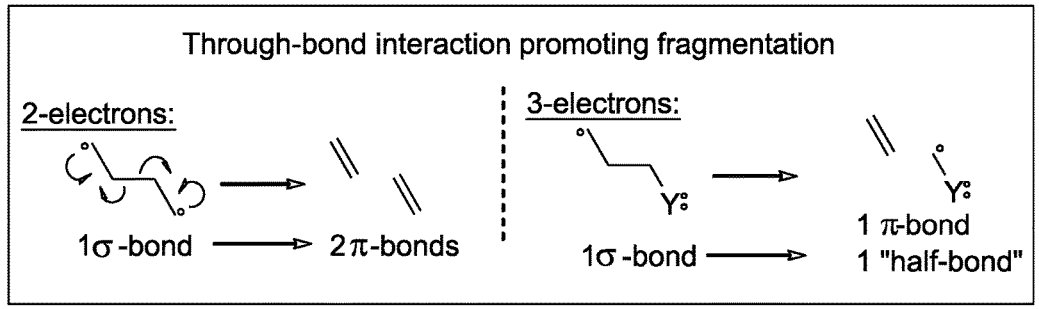
FIG. 7A depicts the transformation of TB electronic coupling between non-bonding orbitals in 1,4-diradicals and β-heteroatom substituted radicals in a C—C bond fragmentation.
Figure 7B:
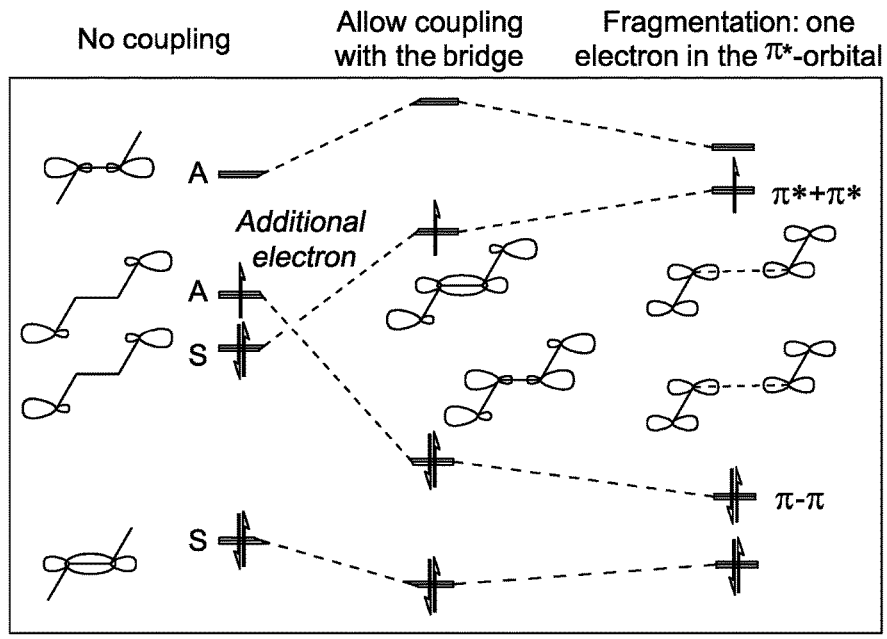
FIG. 7B depicts the energy penalty for inclusion of an additional electron in the fragmenting system.

[a]See FIG. 7 for reaction conditions.
[b]Determined by $Ph_3CH$ internal standard.
[c]With 0.2 eq. PhSH We envisioned that the fragmented radical could be coerced into propagating the radical chain via polarity reversal catalysis. See Reference 10. In such processes, H-atom transfer between two nucleophilic radicals is promoted via an "H-shuttle" with an electrophilic radical.

However, our attempt at increasing the efficiency of propagation steps using thiophenol as the "H-shuttle" decreased the napthalene yield. See Table 1, entry 3. While 10% of 3 was formed (along with 24% of the reactant), we also obtained significant amounts of reduced acyclic products. Product 3 is derived from the least stable of equilibrating radicals, suggesting the radical pool can be depleted if the more stable radicals (incapable of cyclization) find a suitable reaction path. This is consistent with the previous reports of polarity reversal catalysts prematurely terminating radical cascades by trapping relatively unreactive intermediates. See Reference 12.

Another possibility preventing propagation is the facility of further fragmentation of the CH₂XR radical. See Reference 13. We are currently investigating the mechanistic details in hopes of obtaining fragmented species and finding conditions for efficient propagation.

IV. Computational Analysis

Figure 6:
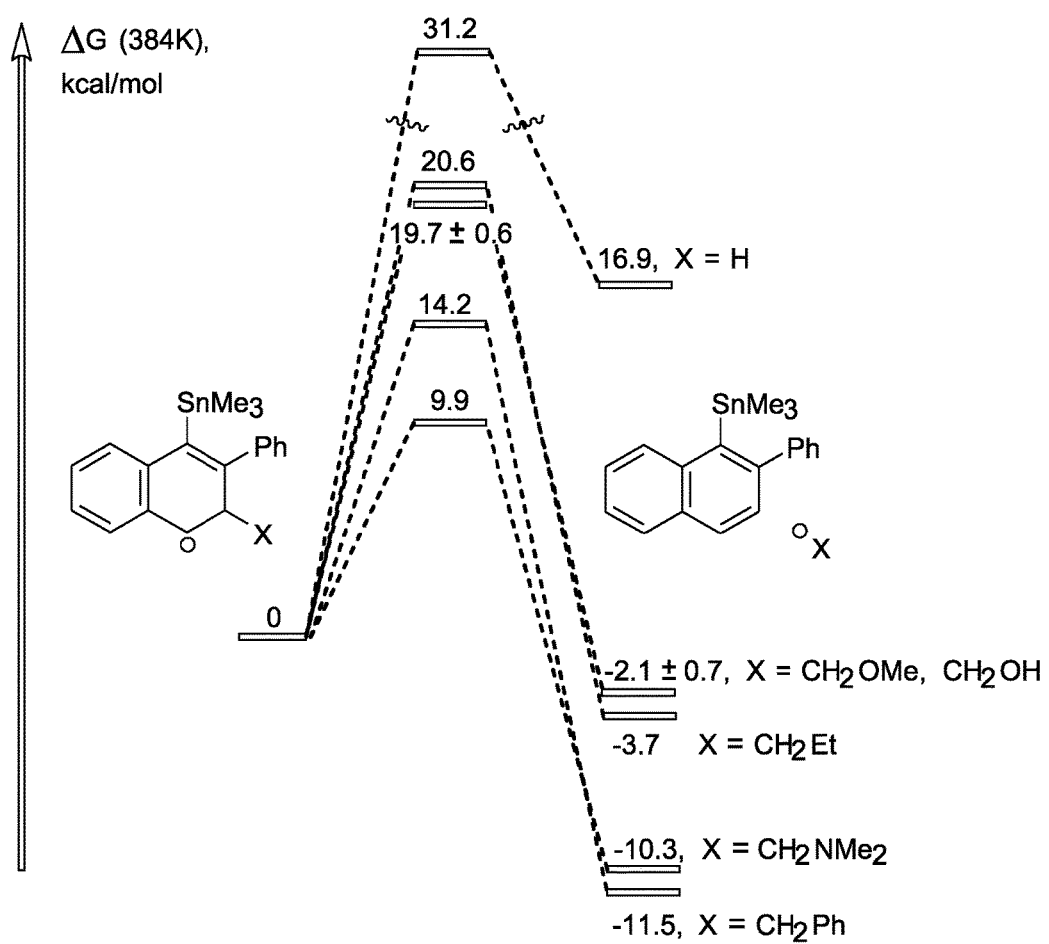
FIG. 6 depicts the calculated energy profiles for the fragmentation at the UM06-2X/LanL2DZ level of theory. Energies in kcal/mol, ΔG values are calculated at 384K.

Further insights into electronic factors responsible for the facile fragmentations came from DFT calculations. Free energies ($\Delta G$) of fragmentation were negative due to combination of radical stabilization and the favorable entropic contribution. Because nitrogen is a better donor than oxygen and because lone pairs are better donors than C—H/C—C bonds, we expected reaction energies to reflect the importance of donor abilities of lone pairs in the stabilization of the fragmented radical in the order analogous to that in FIGS. 3A and 3B; $CH_2NMe_2 > CH_2OMe/CH_2OH > CH_2Alkyl$. See References 14 and 15. However, the calculated exergonicities for the fragmentation of O-containing substrates ($CH_2OMe/CH_2OH$) were lower than that for the propyl-substituted substrate. See FIG. 6 and FIGS. 7A and 7B. This unexpected observation suggests the presence of a new remote electronic effect that stabilizes the benzylic reactants containing a $\beta$-C—X bond, thus decreasing the exergonicity of their fragmentation. We suggest that this effect is a Through-Bond (TB) coupling of the two non-bonding orbitals populated with three electrons (vide infra).

V. Through-Bond Interactions in Odd Electron Systems

Such electronic effects are well-known when both of the non-bonding orbitals are singly occupied (i.e., in 1,4-diradicals). In these systems, through-bond coupling of radical centers increases population of the $\sigma^*$ bridge orbital, ultimately leading to fragmentation into two 2-center, 2-electron bonds (2c-2e). See Reference 16. The same effect is responsible for rendering the Bergman cyclization a symmetry-allowed reaction and providing ca. 3-5 kcal/mol stabilization to p-benzyne. See References 17 and 18. Symmetry-enforced TB interactions play an important role in "aborted" sigmatropic shifts, an unusual class of pericyclic reactions where geometry corresponding to the cyclic TS is more stable than the acyclic reactants. See Reference 8c. However, the role of TB coupling between radical centers and lone pairs in 2c-3e systems is not commonly recognized, perhaps due to the decreased driving force for the fragmentation of monoradicals, where one of the formed bonds is the 2c-3e "half-bond." See FIGS. 7A and 7B and Reference 19.

VI. Increased TB Interaction in the Fragmentation TS

Reactant stabilization is a potentially counterproductive factor in the design of fragmentations. However, the surprisingly large magnitude of kinetic effects on the calculated activation energies in FIG. 6, suggest that these stabilizing interactions become even more important in the transition state and facilitate the fragmentation. See Reference 8.

In order to differentiate thermodynamic contributions to the barrier (the consequence of the increased stability of reaction products) from stabilizing effects intrinsic to the transition state (Equation 1), we turned to Marcus theory. See Reference 20. This approach dissects reaction energy as a combination of intrinsic energy and thermodynamic contribution as described in Eq. 1.

$$\Delta E^{\neq} = \Delta E_0^{\neq} + \frac{1}{2}\Delta E_{rxn} + \Delta E_{rxn}^2/16(\Delta E_0^{\neq}) \qquad \text{Eq. (1)}$$

Stereoelectronic differences in the TS can be identified by examining the intrinsic barrier ($\Delta E_0^{\neq}$), i.e., the barrier of a thermoneutral process lacking the thermodynamic contributions. See Reference 21. The intrinsic barrier can be estimated when both the activation and reaction energies are known. See FIG. 8, which illustrates the stereoelectronics of the fragmentation viewed through the prism of Marcus Theory: The top insert summarizes differences in reaction and activation free energies imposed by the substituents. The bottom insert shows intrinsic reaction barriers for the fragmentation. Energies in kcal/mol.

Based on the Marcus model, one would expect that the effect on the activation barrier should be significantly smaller than effect on the reaction energy ($\Delta\Delta G^{\neq} \sim \frac{1}{2}\Delta\Delta G$). Contrary to these expectations the effect on $\Delta G^{\neq}$ rivals the effect on $\Delta G$ in the case of $X=CH_2NMe_2$. The relatively small and sometimes negative activation entropies are surprising for a fragmentation reaction, suggesting an increased degree of structural organization in the TS. In order to eliminate the complication associated with the difference in the entropic penalties, we focused our attention on reaction energies ($\Delta E$) and discovered even more striking trends (e.g., $\Delta E^{\neq}=22.0$ with $\Delta\Delta E=21.4$ kcal/mol, respectively, for 1A vs. 1E. These surprising observations suggest that the stabilizing effect of the heteroatom starts to manifest itself before a radical center is fully developed at the adjacent carbon.

Figure 8:
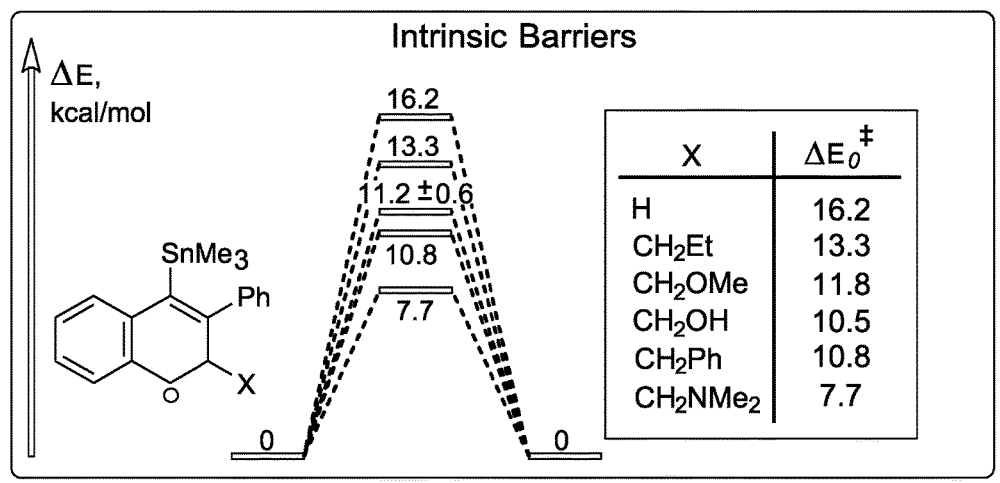
FIG. 8 illustrates the stereoelectronics of the fragmentation viewed through the prism of Marcus Theory: The top insert summarizes differences in reaction and activation free energies imposed by the substituents. The bottom insert shows intrinsic reaction barriers for the fragmentation. Energies in kcal/mol.

The intrinsic reaction barriers are given in FIG. 8. It is clear that when thermodynamic contributions to the barrier are removed, significant differences in the transition state energies remain (1-2 kcal for $X=CH_2OR$ and ~6 kcal/mol for $X=CH_2NMe_2$).

Figure 9:
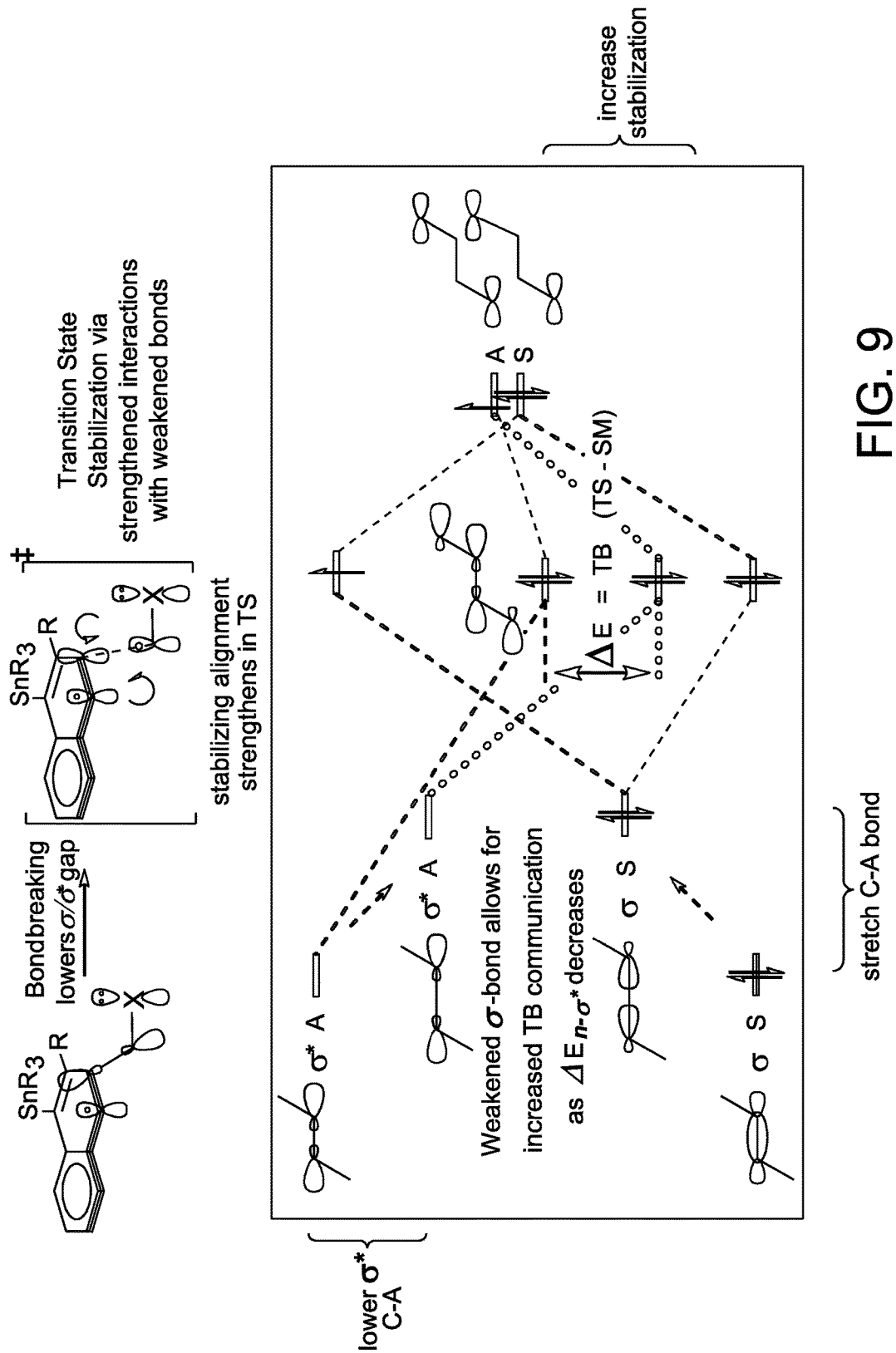
FIG. 9 illustrates electronic coupling between non-bonding orbitals in 1,4-diradicals and β-heteroatom substituted radicals strengthens in the TS, facilitating C—C bond fragmentation. Additional stabilization due to TB coupling through a breaking bridging bond is shown as ΔE. σ and σ* energies in the starting radical are shown in grey.

These large effects on the fragmentation barrier originate from an electronic communication between the non-bonding orbitals that weakens the bridging $\sigma$-bond in the TS. See FIG. 9, which illustrates electronic coupling between non-bonding orbitals in 1,4-diradicals and $\beta$-heteroatom substituted radicals strengthens in the TS, facilitating C—C bond fragmentation. Additional stabilization due to TB coupling through a breaking bridging bond is shown as $\Delta E$. $\sigma$ and $\sigma^*$ energies in the starting radical are shown in grey.

The final computational evidence was provided by Natural Bond Orbital (NBO) analysis of the initial radical, transition state, and "half-bonded" radical fragments that revealed the presence of very strong stabilizing interactions between radical, lone pair of oxygen, and the bridge orbitals. See Table 2.

TABLE 2

NBO analysis at the UM062X/LanL2DZ level of theory. Interaction energies in kcal/mol.

| Interaction | SM | | TS[a] | |
| --- | --- | --- | --- | --- |
|  | α-spin | β-spin | α-spin | β-spin |
| $n_C \to \sigma^*_{C-C}$ | 5.9 | 1.7 | 89.6 | 13.4 |
| $n_O \to \sigma^*_{C-C}$ | 3.9 | 4.9 | 2.7 | 30.7 |
| $\sigma_{C-C} \to n_C$ | — | 5.0 | — | 79.9 |

[a]The given Lewis structure was obtained using the $CHOOSE keyword.
— Indicates the interaction is less than the threshold of 0.5 kcal/mol.

While communication through the a-bridge is present in the radical, the effects become much larger in the TS. The increase in interactions can be understood from the second order perturbation energies provided by NBO analysis (Equation 2).

$$E(2) = q_i \frac{F_{ij}^2}{\Delta E_{ij}}$$   Eq. (2)

During fragmentation the energy of the a-bonding orbital is raised as the σ* is lowered, decreasing the $\Delta E_{ij}$ term for interactions with non-bonding orbitals (i.e., the radical and lone pair). In addition, as the fragmentation progresses, the ~$sp^3$ σ-bond is transformed into two p-orbitals (one π-bonded in naphthalene and the other in a 2c-3e "half-bond"), increasing overlap between interacting orbitals. Together these interactions are responsible for selective TS stabilization for the fragmentation process.

VII. Practical Applications: Access to Extended Polyaromatics

Figure 10:
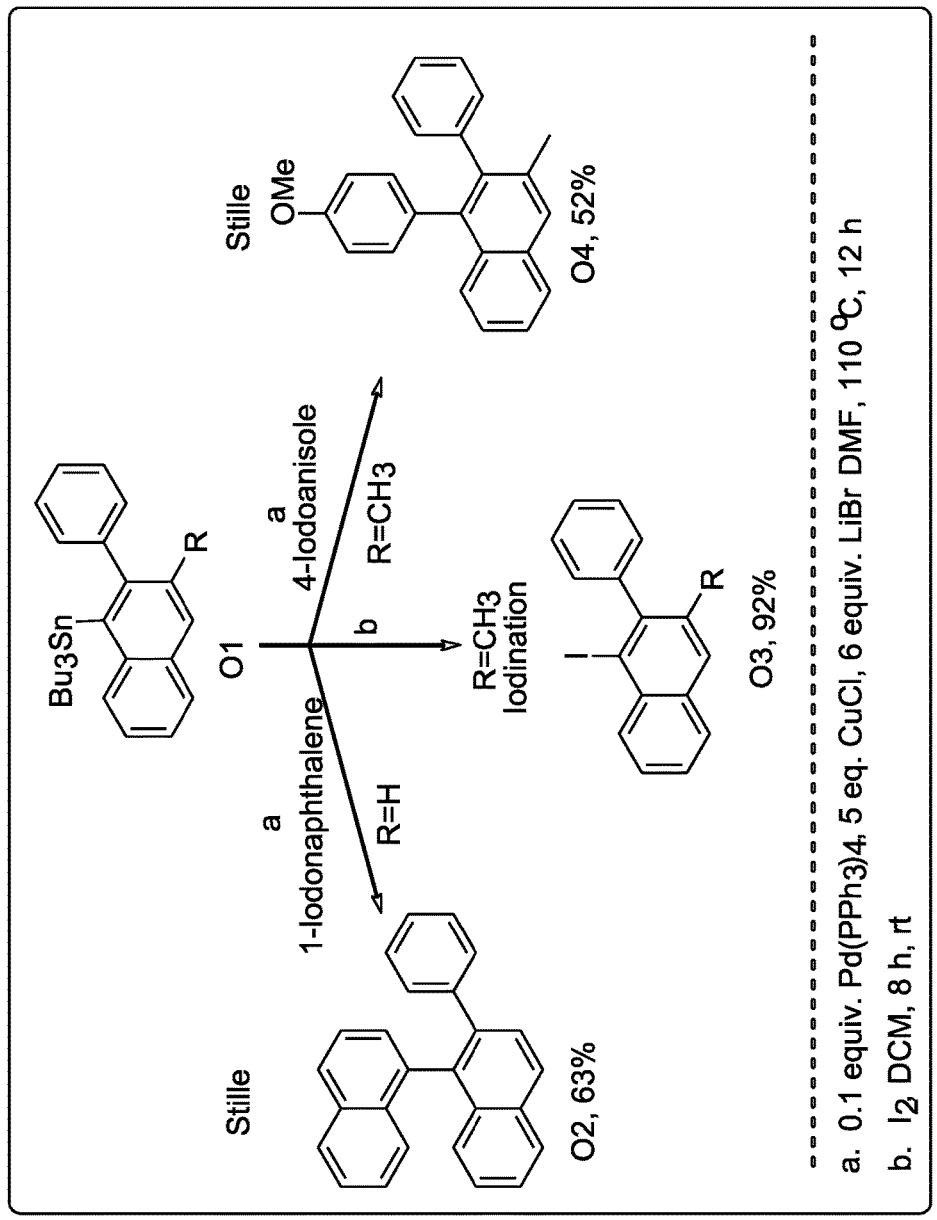
FIG. 10 illustrates the use of $Bu_3Sn$-group as a functional handle for the preparation of more substituted naphthalene building blocks.

For convenience, we usually remove the $Bu_3Sn$ moiety by protodestannylation of the reaction mixtures prior to purification. However, the Sn moiety in the indene and naphthalene products can be retained and utilized as a useful functionality for further synthetic transformations. In particular, Stille coupling and iodination of the α-Sn-substituted naphthalene confirmed the direction of tin attack and presented a synthetic advantage for facile functionalization of naphthalene cores. Both approaches provided highly substituted naphthalene derivatives that are otherwise difficult to prepare from the parent aromatic core, shown in FIG. 10, which illustrates the use of $Bu_3Sn$-group as a functional handle for the preparation of more substituted naphthalene building blocks.

Figure 11:
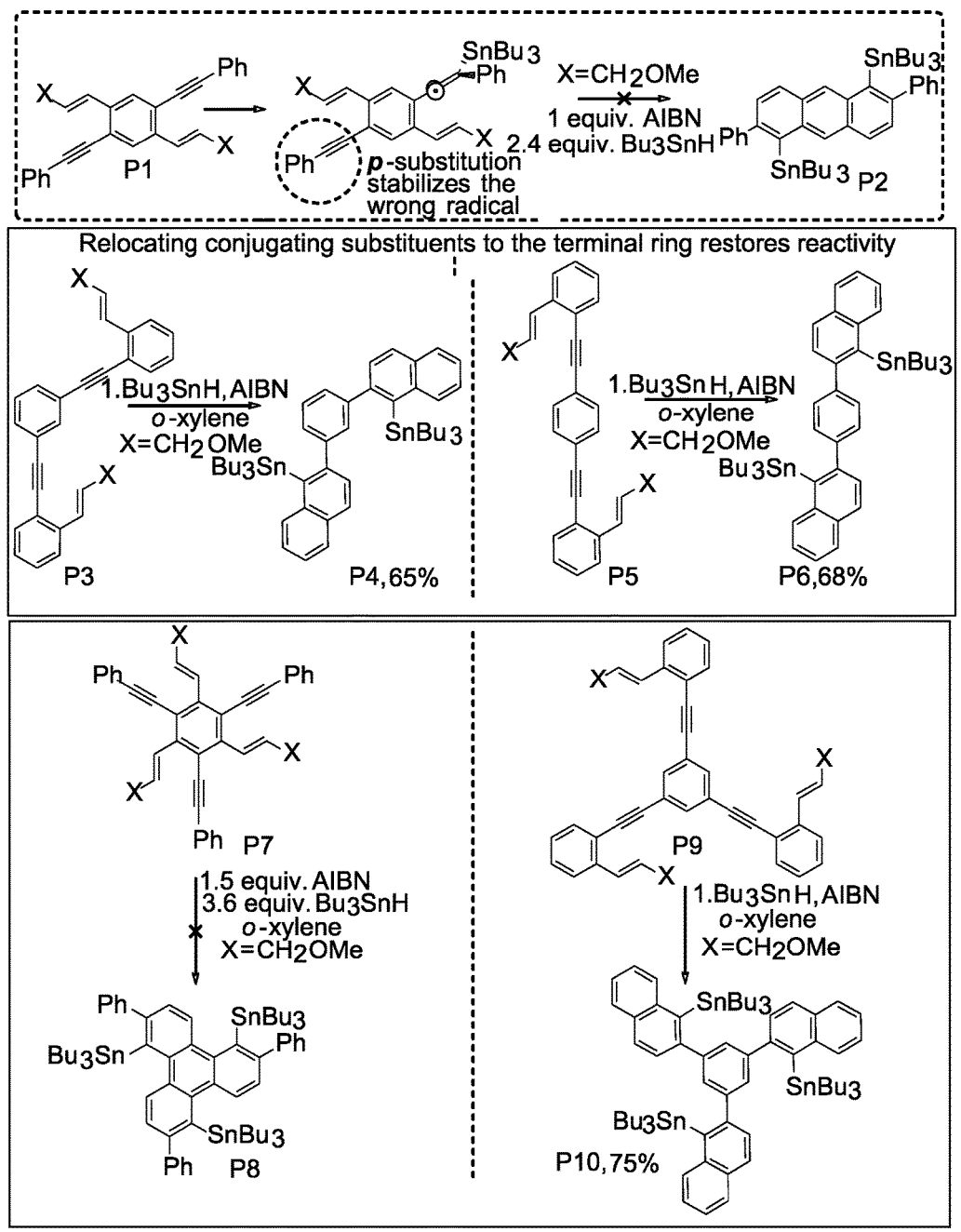
FIG. 11 illustrates conjugating substituents at the core interfere with the cyclization but the same substituents at the periphery effectively participate in the reaction. Furthermore, substitution at the cores is likely to make the substrates too crowded for successful cyclization using the bulky $Bu_3Sn$ radical.

As noted above, changing the alkyne substituent in simple enynes, from benzene to naphthalene or anthracene decreases the product yield. We attribute this decrease to an increase in steric congestion during the intramolecular attack of the vinyl radical on the alkene (compounds K33 and K34). The stabilizing effect of conjugating substituents for the unproductive $Bu_3Sn$ attack at the external alkyne (and, possibly, alkene) positions pose limitations that are illustrated by unsuccessful attempts to directly access triphenylene derivatives from the cyclization of enyne P7 shown in FIG. 11. FIG. 11 illustrates conjugating substituents at the core interfere with the cyclization but the same substituents at the periphery effectively participate in the reaction. Furthermore, substitution at the cores is likely to make the substrates too crowded for successful cyclization using the bulky $Bu_3Sn$ radical.

To test the validity of the above assumption, we moved conjugating substituents to the outside aryl group where they would stabilize the productive radicals. To our delight, we found that, with this structural change, the reaction successfully gives bis- and tris-naphthalene substituted biphenyl compounds P4 and P6 in excellent yield. See FIG. 11. The success of the cascade and selectivity of the transformation was confirmed by X-ray analysis. The overall efficiency of >75% is remarkable considering that nine bonds were formed and six bonds were broken in the process of this cascade that involves the cyclization/expansion/fragmentation sequence at each of the three enyne functionalities.

Figure 12:
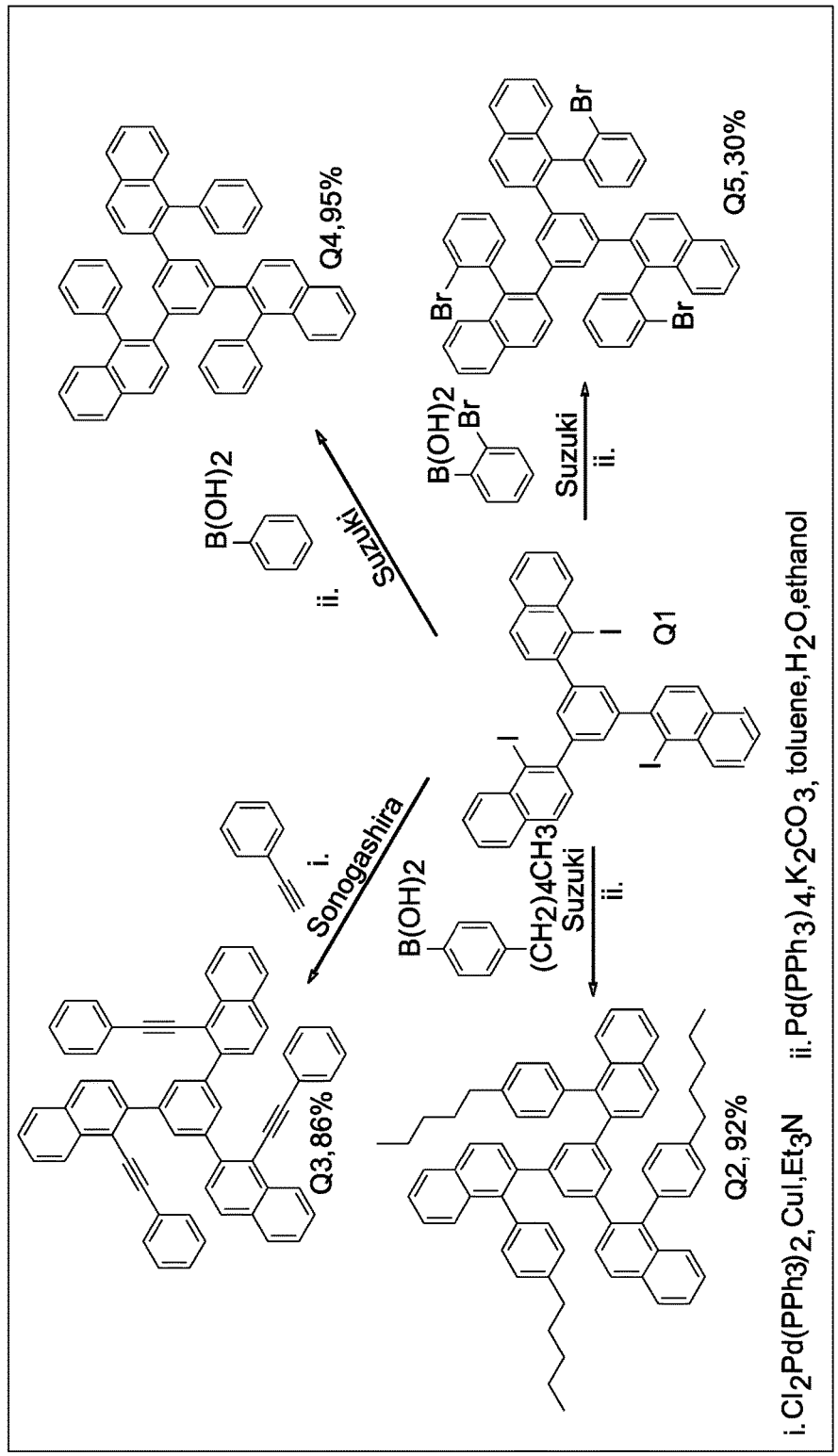
FIG. 12 demonstrates that the utility of the Sn functional handle is demonstrated by iodination and subsequent extension of the trinaphthalene aromatic core with Suzuki and Sonogashira couplings to form large functionalized polyaromatics.

Furthermore, such products can serve as a convenient launching point for the preparation of extended polyaromatics. See FIG. 12, which demonstrates that the utility of the Sn functional handle is demonstrated by iodination and subsequent extension of the trinaphthalene aromatic core with Suzuki and Sonogashira couplings to form large functionalized polyaromatics. For example, the successful iodination of the Sn-substituted 1,3,5-tris(naphthyl)benzene structure P10 creates a versatile scaffold for iterative expansion into larger derivatives. Suzuki coupling with (4-pentylphenyl)boronic acid, phenyl boronic acid, and bromophenyl boronic acid yielded Q2, Q4, Q5 in 92, 95 and 30% yield, respectively. Alternatively, Sonogashira coupling with phenylacetylene gave the trialkynyl product Q3 in 86%.

The present work describes a radical cascade which self-terminates via expulsion of primary C-centered radicals. Even though the energetic penalty for the homolytic cleavage of a strong C—C bond is significant, the combination of two stabilizing effects (the aromatic stabilization gained in the product and stabilization of radical leaving groups with 2c-3e bonds) can compensate for the cost of C—C bond cleavage. In the reaction sequence, a radical center is relocated to a position where it can communicate with a donor lone pair through a C—C bridge (TB interaction). Such communication leads to selective TS stabilization for the C—C bond cleavage. This work illustrates the potential of 2c-3e interactions in the design of radical leaving groups. Incorporation of C—C bond cleavage into self-terminating radical cascades allows the use of alkenes as alkyne equivalents for the preparation of aromatic structures.

EXAMPLES

The following non-limiting examples are provided to further illustrate the present invention.

Example 1. General Procedures

Toluene and THF were obtained from Glass Contour Solvent Purification System. Hexanes for column chromatography and preparatory thin layer chromatography were distilled prior to use. All other solvents were used as purchased. Column chromatography was performed using silica gel (60 Å) and Preparatory thin layer chromatography was performed using a 1000 μm glass backed plate containing UV dye. Unless otherwise noted, $^1H$ NMRs were run on 400 MHz and 600 MHz spectrometer in $CDCl_3$ and $^{13}C$ NMR were run on 100 MHz and 150 MHz spectrometer in $CDCl_3$. Proton chemical shifts are given relative to the residual proton signal of $CDCl_3$ (7.26 ppm). Carbon chemical shifts were internally referenced to $CDCl_3$ (77.23 ppm) signal. All J-coupling values are reported in Hertz (Hz).

Example 2. Cyclization Reaction

The starting enyne (0.34 mmol) was degassed in 4 mL of toluene and heated to reflux. Two separate solutions of AIBN (0.5 eq.) and $Bu_3SnH$ (1.2 eq.) each in 3 mL toluene were added using syringe pump through the top of a condenser over the course of 4 hours into the refluxing solution. The reaction was allowed to stir at reflux. Reaction progress was monitored by TLC. After completion, the solvent was evaporated and the product was dissolved in 20 mL DCM and washed with a 1M HCl. The product was purified on silica gel using a gradient of ethyl acetate:hexane as eluent.

Example 3. Scheme A: Procedure for Synthesis of Compound 1A

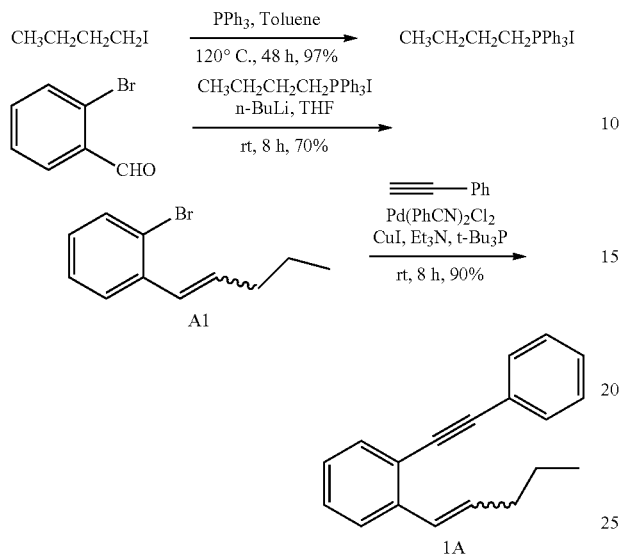

Preparation of Wittig Salt—Butyltriphenylphosphonium Iodide

Butyl iodide (2 g, 10.8 mmol) was added dropwise into a solution of triphenylphosphine (7 g, 10.8 mmol) in toluene in a pressure tube at room temperature. It was stirred for 48 hours at 120° C. The separated solid was filtered through a Buchner funnel and the residue was washed with petroleum ether. The resulting white solid was recrystallized from distilled petroleum ether (60-80° C.). Yield: 97%.

Wittig Reaction n-BuLi (3 mL of a 1.5M solution in Hexane, 3.0 mmol) was added slowly to a solution of Wittig salt from butyl iodide (3.5 mmol) in anhydrous THF (10 mL) at room temperature. After 30 min, a solution of 2-bromobenzaldehyde (3.5 mmol) in THF (10 mL) was added dropwise. The resulting solution was allowed to stir at room temperature for 12 h and quenched with saturated NH$_4$Cl solution. The aqueous phase was extracted with Et$_2$O (3×30 mL), and the combined organic layers were washed with brine, dried over anhydrous Na$_2$SO$_4$, and evaporated under reduced pressure. The crude mixture was purified by column chromatography (hexane) on silica gel affording A1 (70%) as colorless oil.

Sonogashira Cross Coupling of Aryl Bromide A1 with Phenylacetylene (1A):

A suspension of aryl bromide (4.5 mmol), PdCl$_2$ (PhCN)$_2$ (0.23 mmol), Cu(I) iodide (0.23 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.45 mmol in a 10% solution of toluene) was added, immediately followed by 1.2 equiv. of phenylacetylene (5.4 mmol) using a syringe. The mixture was allowed to react for 8 hours and monitored by TLC. After total consumption of the aryl bromide, the reaction mixture was filtered through celite and extracted with DCM (3×30 mL). The organic layer was washed with a saturated solution of ammonium chloride, water and dried over anhydrous Na$_2$SO$_4$. Solvent was removed under educed pressure. The reaction mixture was purified by flash chromatography (eluent: hexane/ethyl acetate) on silica gel to afford compound 1A (90%).

Compound A1: 1-bromo-2-(pent-1-en-1-yl)benzene (Mixture of Z and E (3:2))

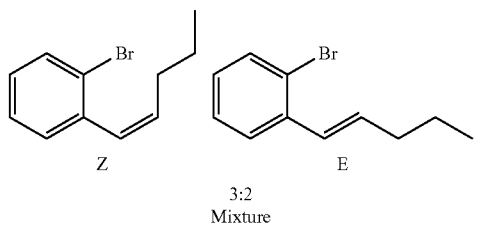

Chromatographic purification (hexane) afforded compound 1A (70% yield) as a yellow oil. Rf=0.6 (hexane); $^1$H NMR (400 MHz; CDCl$_3$) δ7.59 (d, J=8.0 Hz), 7.55-7.49 (m), 7.32-7.23 (m), 7.13-7.04 (m), 6.64 (d, J=15.7 Hz), 6.48 (d, J=11.5 Hz), 6.19 (td, J=15.7, 7.0 Hz), 5.80 (td, J=11.5, 7.4 Hz), 2.26 (dq, J=7.4, 1.2 Hz), 2.18 (dq, J=7.4, 1.7 Hz), 1.57-1.42 (m), 1.0 (t, J=7.4 Hz), 0.93 (t, J=7.4 Hz). $^{13}$C NMR (100 MHz; CDCl$_3$) δ 137.9, 134.2, 134.1, 133.0, 132.7, 130.8, 129.0, 128.7, 128.3, 127.5, 127.0, 124.2, 123.3, 35.4, 30.6, 23.0, 22.6, 14.0, 13.9. HRMS (EI): calcd for C$_{11}$H$_{13}$Br [M]+224.0201, found 224.0198. IR (neat, cm$^{-1}$): 3022, 1499, 1020.

Compound 1A: 1-(pent-1-en-1-yl)-2-(phenylethynyl)benzene (Mixture of Z and E (3:2))

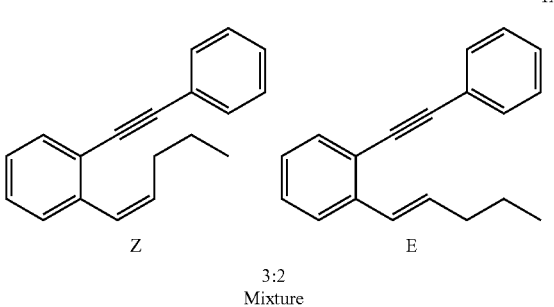

Chromatographic purification (hexane) afforded compound 1A (90% yield) as a yellow oil. Rf=0.6 (hexane); $^1$H NMR (400 MHz; CDCl$_3$) δ 7.66-7.59 (m), 7.50-7.46 (m), 7.45-7.36 (m), 7.33-7.29 (m), 7.28-7.25 (m), 7.15-7.06 (m), 7.11 (t, J=16.9 Hz), 6.90 (d, J=11.7 Hz), 6.50-6.40 (m), 5.90 (td, J=11.7, 7.3 Hz), 2.40-2.33 (m), 1.66-1.54 (m), 1.08 (t, J=7.4 Hz), 1.03 (t, J=7.4 Hz). $^{13}$C NMR (100 MHz; CDCl$_3$) δ 141.4, 139.8, 139.6, 134.1, 133.1, 132.6, 132.4, 131.7, 129.3, 129.0, 128.9, 128.8, 128.6, 128.5, 128.4, 128.3, 128.2, 128.0, 127.7, 126.6, 126.5, 124.9, 123.7, 122.8, 121.9, 121.3, 108.3, 99.9 (2C), 88.6, 88.4, 35.6, 31.0, 23.2, 22.6, 14.0. HRMS (ED: calcd for C$_{19}$H$_{18}$[M]+246.1409, found 246.1400. IR (neat, cm$^{-1}$): 3024, 1491, 1069.

Example 4. Scheme B: Procedure for Synthesis of Compound (1B)

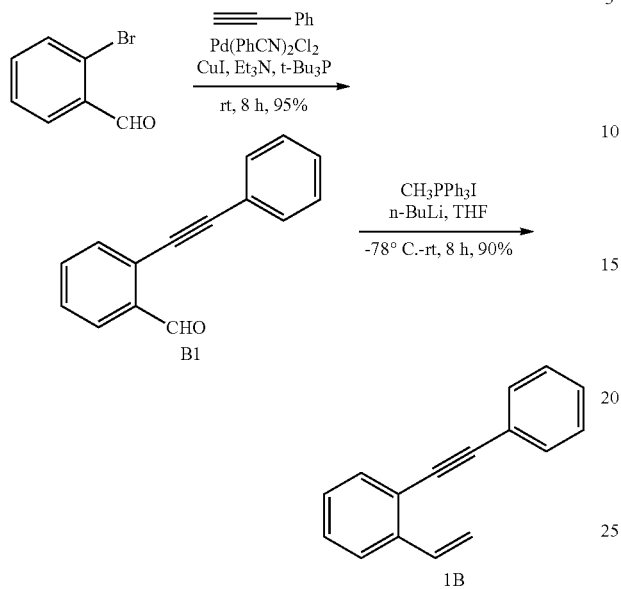

Sonogashira Cross Coupling of 2-bromobenzaldehyde with Phenylacetylene (B1):

A suspension of aryl bromide (4.5 mmol), PdCl$_2$(PhCN)$_2$ (0.23 mmol), Cu(I) iodide (0.23 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.45 mmol in a 10% solution of toluene) was added, immediately followed by 1.2 equiv. of phenylacetylene (5.4 mmol) using a syringe. The mixture was allowed to react for 8 hours and monitored by TLC. After total consumption of the aryl bromide, the reaction mixture was filtered through celite and extracted with DCM (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compounds B1 (95%).

Wittig Reaction

To a solution of the Wittig salt from iodomethane (3.5 mmol) in anhydrous THF (10 mL) at −78° C. was added slowly n-BuLi (3 mL of a 1.5M solution in hexane, 3.0 mmol). After 45 min, a solution of B1 (3.5 mmol) in THF (10 mL) was added dropwise. The resulting solution was stirred for 40 min at −78° C. Then, the reaction mixture was allowed to reach room temperature and quenched with saturated NH$_4$Cl solution. The aqueous phase was extracted with Et$_2$O (3×30 mL), and the combined organic layers were washed with brine, dried over anhydrous Na$_2$SO$_4$, and evaporated under reduced pressure. The crude was purified by column chromatography (hexane) on silica gel affording 1B (90%) as a yellow oil.

Compound 1B: 1-(phenylethynyl)-2-vinylbenzene

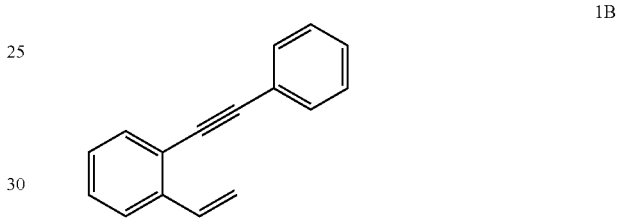

Chromatographic purification (hexane) afforded compound 1B (90% yield) as a yellow oil. Rf=0.6 (hexane); $^1$H NMR (400 MHz; CDCl$_3$) δ 7.65 (1H, d, J=8.1 Hz), 7.63-7.56 (3H, m), 7.42-7.33 (5H, m), 7.27 (1H, dt, J=7.5, 1.1 Hz), 5.91 (1H, d, J=17.6 Hz), 5.45 (1H, d, J=11.0 Hz). $^{13}$C NMR (100 MHz; CDCl$_3$) δ 139.2, 135.1, 132.7, 131.7 (2C), 128.6, 128.5 (3C), 127.7, 124.9, 123.5, 122.1, 115.8, 94.2, 87.9. HRMS (EI): calcd for C$_{16}$H$_{12}$ [M]+204.0939, found 204.0936. IR (neat, cm$^{-1}$): 3059, 2213, 1490, 898.

Example 5. Scheme C: General Procedure for Synthesis of Compounds 1C-1D

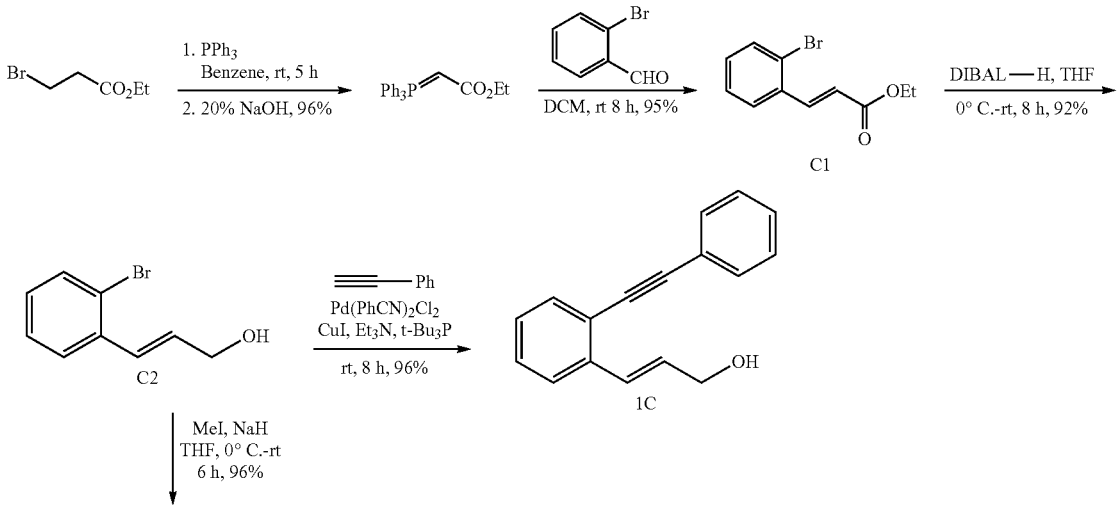

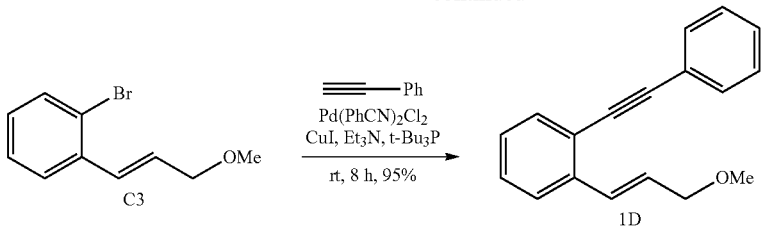

Preparation of Wittig Salt—Ethyl (Triphenylphosphoranylidene) Acetate:

Ethyl bromoacetate (2.9 mL, 26.7 mmol) was added dropwise into a solution of triphenylphosphine (7 g, 26.7 mmol) in benzene at room temperature. It was stirred for 4-5 hours. The separated solid was filtered through a Buchner funnel and the residue was washed with hexane. The resulting white solid was taken in benzene (200 mL) and 15 g sodium hydroxide in 100 mL of water. It was stirred until both layers became clear. The benzene layer was taken out, dried over sodium sulfate and concentrated. The white salt was recrystallized from distilled petroleum ether (60-80° C.). Yield: 96%.

Wittig Reaction (C1):

Ethyl (triphenylphosphoranylidene) acetate (2.80 g, 8.17 mmol) was added to a solution of bromobenzaldehyde (1.0 g, 5.4 mmol) in dry DCM (dichloromethane) at 0° C. and stirred for 8 hours at room temperature. The solvent was then evaporated under vacuum. The colorless oil was partitioned between ethyl acetate and water. The organic layer was washed with water, brine and dried over $Na_2SO_4$. It was then filtered and evaporated to give an oil from which the title compound C1 was isolated by column chromatography (Si-gel, PE:EA=15:1). Yield: 95%; State: colorless oil.

DIBAL-H Reduction of α,β-Unsaturated Ester C1(C2):

A THF solution of compound C1 (2.0 g, 7.8 mmol) was cooled to 0° C. Diisobutylaluminum hydride (DIBAL-H, 1.0M in hexane, 15 ml, 15 mmol) was slowly added to this solution under a nitrogen atmosphere and was stirred for 6 h. The reaction was quenched with aq. $NH_4Cl$ sol. (20 ml) and extracted with ethyl acetate (100 ml). The extract was washed with brine solution, dried over $MgSO_4$, and concentrated under reduced pressure. The residue was eluted through a silica column to afford C2 as a colorless oil (92%).

Methylation of 2-bromocinnamyl alcohol C2 (C3):

To a suspension of NaH (60% dispersion in mineral oil) in THF (20 mL) was added 2-bromocinnamyl alcohol C2 (1.0 g, 4.7 mmol) at room temperature. The mixture was stirred for 100 min at room temperature, after which MeI (0.9 ml, 14 mmol, 3 equiv) was added in one portion. The mixture was stirred for 1 h at room temperature, then filtrated through a pad of silica gel. The solid was washed using hexane/ethyl acetate (1:1) as the eluent, and the filtrate was concentrated and purified by silica gel column chromatography, using 5% ethylacetate in hexane as the eluent, to afford the title compound C3 (96% yield) as colorless oil.

Sonogashira Cross Coupling of Aryl Bromides (C2, C3) with Phenylacetylene (1C-1D):

A suspension of aryl bromide (4.5 mmol), $PdCl_2(PhCN)_2$ (0.23 mmol), Cu(I) iodide (0.23 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.45 mmol in a 10% solution of toluene) was added, immediately followed by 1.2 equiv. of phenylacetylene (5.4 mmol) using a syringe. The mixture was allowed to react for 8 hours and monitored by TLC. After total consumption of the aryl bromide, the reaction mixture was filtered through celite and extracted with DCM (3×30 mL). The organic layer was washed with a saturated solution of ammonium chloride, water and dried over anhydrous $Na_2SO_4$. Solvent was removed under reduced pressure. The reaction mixture was purified by flash chromatography (eluent: hexane/ethyl acetate) on silica gel to afford compounds 1C-1D in 96-95% yields.

Compound 1C: (E)-3-(2-(phenylethynyl)phenyl) prop-2-en-1-ol

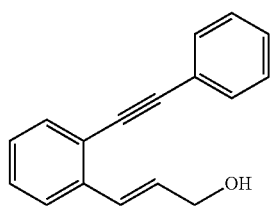

Chromatographic purification (5% ethyl acetate in hexane) afforded compound 1C (96% yield) as a brown solid; m.p. 59° C.; Rf=0.6 (5% ethyl acetate in hexane); $^1H$ NMR (600 MHz; $CDCl_3$) δ 7.58-7.53 (4H, m), 7.38-7.34 (3H, m), 7.30 (1H, t, J=7.4 Hz), 7.25-7.22 (1H, m), 7.20 (1H, d, J=15.9 Hz), 6.48 (1H, td, J=15.9, 5.7 Hz), 4.38 (2H, dd, J=5.7, 1.3 Hz), 1.73 (1H, bs). $^{13}C$ NMR (150 MHz; $CDCl_3$) δ 138.2, 132.6, 131.6 (2C), 130.8, 128.8, 128.6, 128.5 (2C), 128.4, 127.3, 125.2, 123.3, 121.9, 94.1, 87.9, 63.7. HRMS (ED: calcd for $C_{17}H_{14}O$ [M]+234.1045, found 234.1039. IR (neat, $cm^{-1}$): 3325 (b), 3056, 2856, 1491.

Compound C3: (E)-1-bromo-2-(3-methoxyprop-1-en-1-yl)benzene

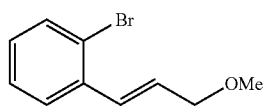

Chromatographic purification (5% ethyl acetate in hexane) afforded compound C3 (96% yield) as a colorless oil. Rf=0.5 (3% ethyl acetate in hexane); $^1H$ NMR (400 MHz; $CDCl_3$) δ 7.54 (2H, dt, J=7.9, 1.1 Hz), 7.26 (1H, t, J=7.6 Hz), 7.09 (1H, dt, J=7.7, 1.5 Hz), 6.80 (1H, d, J=15.8 Hz), 6.22 (1H, td, J=15.8, 5.6 Hz), 4.12 (2H, dd, J=5.9, 1.4

Hz), 3.41 (3H, s). $^{13}$C NMR (100 MHz; CDCl$_3$) δ 136.8, 133.1, 131.3, 129.2, 129.1, 127.7, 127.3, 123.8, 73.1, 58.3. HRMS (ED: calcd for C$_{10}$H$_{11}$BrO [M]+225.9993, found 225.9989. IR (neat, cm$^{-1}$): 3055, 1440, 1113.

Compound 1D: (E)-1-(3-methoxyprop-1-en-1-yl)-2-(phenylethynyl)benzene

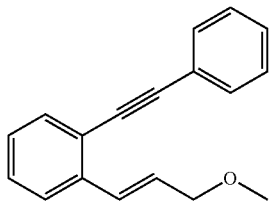

Chromatographic purification (5% ethyl acetate in hexane) afforded compound 1D (95% yield) as a brown oil. Rf=0.6 (5% ethyl acetate in hexane); $^1$H NMR (400 MHz; CDCl$_3$) δ 7.61-7.54 (4H, m), 7.41-7.36 (3H, m), 7.31 (1H, t, J=7.6 Hz), 7.26-7.20 (2H, m), 6.41 (1H, td, J=16.0, 6.0 Hz), 4.18 (2H, dd, J=6.0, 1.1 Hz), 3.43 (3H, s).). $^{13}$C NMR (100 MHz; CDCl$_3$) δ 138.3, 132.7, 131.7 (2C), 130.7, 128.7, 128.6, 128.5 (2C), 128.1, 127.5, 125.4, 123.5, 122.1, 94.2, 88.0, 73.4, 58.2. HRMS (ED: calcd for C$_{18}$H$_{16}$O [M]+ 248.1201, found 248.1200. IR (neat, cm$^{-1}$): 3055, 2214, 1489, 965.

Example 6. Scheme D: Procedure for Synthesis of Compound 1E

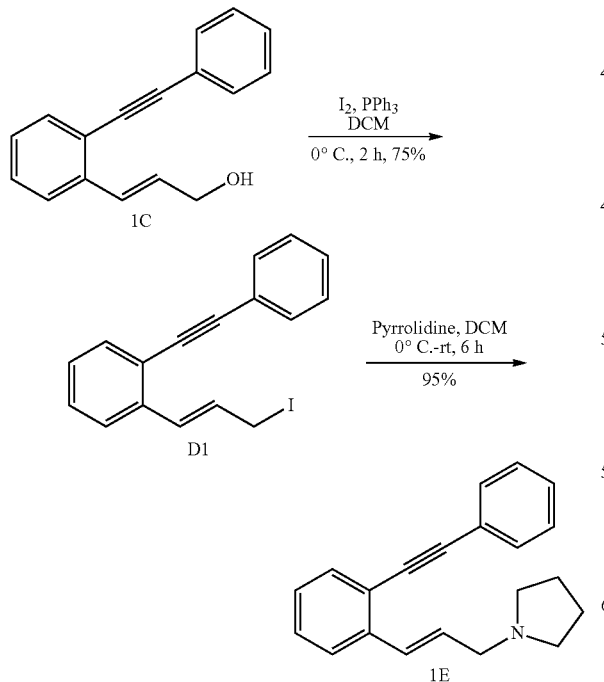

Iodination of Alcohol 1C (D1):
A DCM solution of compound 1C (0.5 g, 2.13 mmol) was cooled to 0° C. Triphenylphosphine (0.61 g, 2.35 mmol), iodine (0.59 g, 2.35 mmol), and imidazole (0.29 g, 4.26 mmol) were slowly added to this solution. After stirring at 0° C. for 2 h, the reaction was quenched with water and extracted with ethyl acetate (50 ml). The extract was washed with brine solution, dried over MgSO4, and concentrated under reduced pressure. The residue was eluted through a silica column to afford compound D1 (75%) as darkbrown solid.

Allylic Substitution Reaction of D1 with Pyrrolidine (1E):
A DCM solution of compound D1 (0.5 g, 2.13 mmol) was cooled to 0° C. Pyrrolidine (0.59 g, 2.35 mmol), was slowly added to this solution and it was stirred at room temperature for 6 h. The reaction was quenched with water and extracted with ethyl acetate (50 ml). The extract was washed with brine solution, dried over MgSO4, and concentrated under reduced pressure. The residue was eluted through a silica column with 15% ethyl acetate in hexane to afford compound 1E (95%) as dark green oil.

Compound D1: (E)-1-(3-iodoprop-1-en-1-yl)-2-(phenylethynyl)benzene

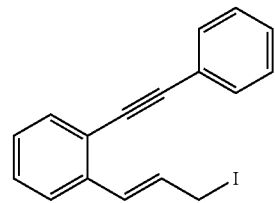

Chromatographic purification (hexane) afforded compound D1 (75% yield) as a dark brown solid; m.p. 63° C.; Rf=0.3 (hexane); $^1$H NMR (400 MHz; CDCl$_3$) δ 7.60-7.52 (4H, m), 7.42-7.37 (3H, m), 7.31 (1H, dt, J=7.6, 1.5 Hz), 7.24 (1H, dt, J=7.5, 1.4 Hz), 7.18 (1H, d, J=15.6 Hz), 6.57 (1H, td, J=15.6, 8.2 Hz), 4.18 (2H, dd, J=8.2, 1.0 Hz). $^{13}$C NMR (100 MHz; CDCl$_3$) δ 137.4, 132.9, 131.8 (2C), 131.2, 128.9, 128.7 (2C), 128.6 (2C), 128.0, 125.5, 123.4, 122.3, 94.6, 87.7, 7.0. HRMS (EI): calcd for C$_{17}$H$_{13}$I [M]+ 344.0062, found 344.0054. IR (neat, cm$^{-1}$): 3015, 2923, 1490, 1135, 958.

Compound 1E: (E)-1-(3-(2-(phenylethynyl)phenyl)allyl)pyrrolidine

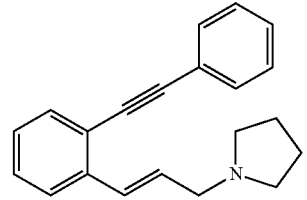

Chromatographic purification (15% ethyl acetate in hexane) afforded compound 1E (95% yield) as a dark green oil. Rf=0.5 (20% ethyl acetate in hexane); $^1$H NMR (400 MHz; CDCl$_3$) δ 7.58-53 (3H, m), 7.51 (1H, dd, J=7.5, 1.1 Hz), 7.38-7.33 (3H, m), 7.30-7.26 (1H, m), 7.20 (1H, dt, J=7.5, 1.2 Hz), 7.13 (1H, d, J=15.9 Hz), 6.43 (1H, td, J=15.9, 6.7 Hz), 3.33 (2H, dd, J=6.7, 1.3 Hz), 2.61-2.57 (4H, m), 1.82-1.79 (4H, m). $^{13}$C NMR (100 MHz; CDCl$_3$) δ 138.8, 132.6, 131.6 (2C), 130.0, 129.8, 128.6, 128.5 (2C), 128.4, 127.2, 125.1, 123.5, 121.8, 94.0, 88.1, 58.7, 54.2 (2C), 23.6 (2C). HRMS (EI): calcd for C$_{21}$H$_{21}$N[M]+ 287.1674, found 287.1679. IR (neat, cm$^{-1}$): 3057, 2959, 2783, 1491, 966.

Example 7. Scheme E: Procedure for Synthesis of Compound 1F

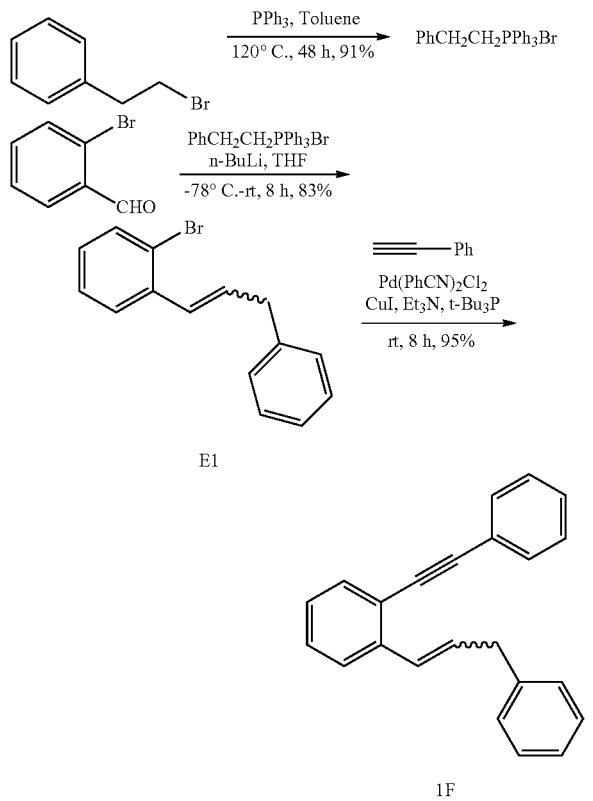

Preparation of Wittig Salt—Phenethyltriphenylphosphoniumbromide (2-bromoethyl)benzene (10.0 mmol) was added dropwise into a solution of triphenylphosphine (10.0 mmol) in toluene in a pressure tube at room temperature. It was stirred for 48 hours at 120° C. The separated solid was filtered through a Buchner funnel and the residue was washed with hexane. The resulting white solid was recrystallized from distilled petroleum ether (60-80° C.). Yield: 91%.

Wittig Reaction

To a solution of the Wittig salt from (2-bromoethyl) benzene (3.5 mmol) in anhydrous THF (10 mL) at −78° C. was added slowly n-BuLi (3 mL of a 1.5M solution in hexane, 3.0 mmol). After 30 min, a solution of 2-bromobenzaldehyde (3.5 mmol) in THF (10 mL) was added dropwise. The resulting solution was stirred for 1 h at −78° C. and then at room temperature for 12 h and quenched with saturated NH$_4$Cl solution. The aqueous phase was extracted with Et$_2$O (3×30 mL), and the combined organic layers were washed with brine, dried over anhydrous Na$_2$SO$_4$, and evaporated under reduced pressure. The crude was purified by column chromatography (hexane) on silica gel affording E1 (E:Z=1: 4, 83%) as colorless oil.

Sonogashira Cross Coupling of Aryl Bromide E1 with Phenylacetylene(1F):

A suspension of aryl bromide (4.5 mmol), PdCl$_2$(PhCN)$_2$ (0.23 mmol), Cu(I) iodide (0.23 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.45 mmol in a 10% solution of toluene) was added, immediately followed by 1.2 equiv. of phenylacetylene (5.4 mmol) using a syringe. The mixture was allowed to react for 8 hours and monitored by TLC. After total consumption of the aryl bromide, the reaction mixture was filtered through celite and extracted with DCM (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compounds 1F (95%).

Compound E1: 1-bromo-2-(3-phenylprop-1-en-1-yl)benzene

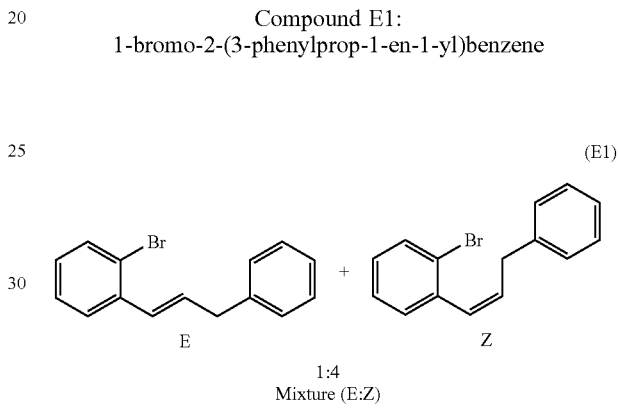

Chromatographic purification (hexane) afforded compound E1 (78% yield) as a colorless oil.; Rf=0.4 (hexane); $^1$H NMR (400 MHz; CDCl$_3$) δ 7.61 (dd, J=8.0, 1.0 Hz), 7.54-7.48 (m), 7.34-7.28 (m), 7.23-7.20 (m), 7.13 (dt, J=7.8, 1.8 Hz), 7.07 (dt, J=7.8, 1.6 Hz), 6.82 (d, J=15.6 Hz), 6.62 (d, J=11.3 Hz), 6.29 (td, J=15.6, 7.0 Hz), 5.98 (td, J=11.3, 7.6 Hz), 3.64 (d, J=7.0 Hz), 3.52 (d, J=7.6 Hz). $^{13}$C NMR (100 MHz; CDCl$_3$) δ 140.4, 137.4, 133.0, 132.8, 132.4, 131.8, 130.6, 130.1, 129.8, 128.8, 128.7, 128.6, 128.5, 127.6, 127.1, 126.5, 126.3, 124.3, 39.6, 34.6. HRMS (EI): calcd for C$_{15}$H$_{13}$Br[M]+ 272.0201, found 272.0198. IR (neat, cm$^{-1}$): 3058, 1490.

Compound 1F: 1-(phenylethynyl)-2-(3-phenylprop-1-en-1-yl)benzene

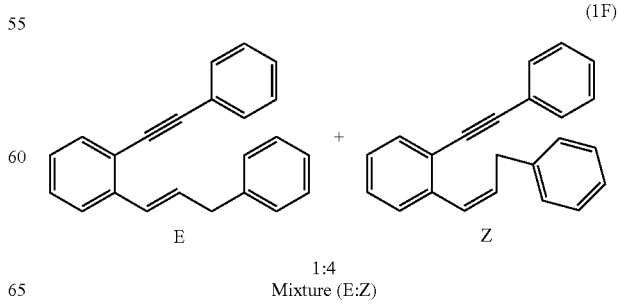

Chromatographic purification (hexane) afforded compound 1F (78% yield) as a colorless oil.; Rf=0.4 (hexane); $^1$H NMR (600 MHz; CDCl$_3$) δ 7.62-7.61 (m), 7.58-7.56 (m), 7.54 (d, J=7.7 Hz), 7.51-7.49 (m), 7.45 (d, J=7.7 Hz), 7.43-7.36 (m), 7.35-7.31 (m), 7.29-7.27 (m), 7.24-7.20 (m), 7.04 (d, J=15.8 Hz), 6.96 (d J=11.4 Hz), 6.53 (td, J=15.8, 6.8 Hz), 6.03 (td, J=11.4, 7.6 Hz), 3.67 (d, J=7.6 Hz), 3.65 (d, J=7.4 Hz), $^{13}$C NMR (150 MHz; CDCl$_3$) δ 140.8, 139.3, 132.7, 132.5, 131.9, 131.8, 131.7, 131.5, 129.3, 129.1, 129.0, 128.9, 128.7 (2C), 128.6, 128.5 (2C), 128.2, 127.1, 127.0, 126.5, 126.4, 126.3, 125.1, 123.6, 123.0, 94.1, 88.5, 39.8, 35.0. HRMS (EI): calcd for C$_{23}$H$_{18}$ [M]+294.1409, found 294.1405. IR (neat, cm$^{-1}$): 3059, 3024, 1490, 1027.

Example 8. Scheme F: Procedure for Synthesis of Compound 1G

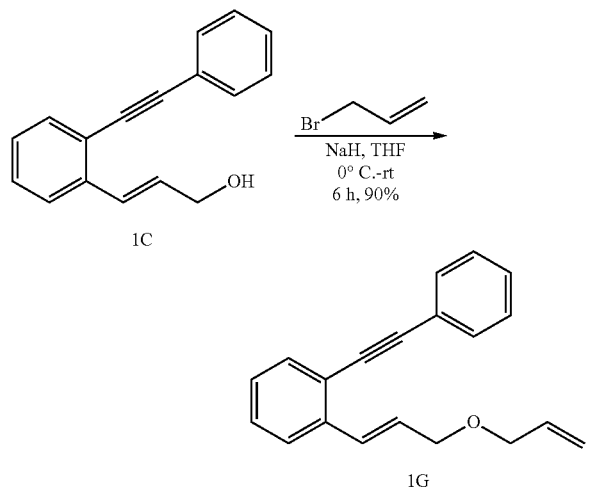

Allylation of Enynealcohol 1C (1G):

To a suspension of NaH (60% dispersion in mineral oil) in THF (20 mL) was added cinnamyl alcohol 1C (0.5 g, 2.3 mmol) at room temperature. The mixture was stirred for 100 min at room temperature, after which allylbromide (7 mmol, 3 equiv) was added in one portion. The mixture was stirred for 1 h at room temperature, then filtered through a pad of silica gel. The solid was washed using hexane/ethyl acetate (1:1) as the eluent, and the filtrate was concentrated and purified by silica gel column chromatography, using 5% ethyl acetate in hexane as the eluent, to afford the title compound 1G (90% yield) as colorless oil.

Compound 1G: (E)-1-(3-(allyloxy)prop-1-en-1-yl)-2-(phenylethynyl)benzene

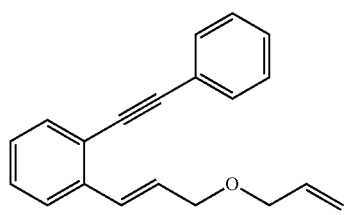

Chromatographic purification (5% ethyl acetate in hexane) afforded compound 1G (91% yield) as a white oil.; Rf=0.6 (5% ethyl acetate in hexane); $^1$H NMR (400 MHz; CDCl$_3$) δ 7.60-7.53 (4H, m), 7.39-7.35 (3H, m), 7.31 (1H, t, J=7.5 Hz), 7.26-7.22 (2H, m), 6.46-6.39 (1H, m), 6.03-5.93 (1H, m), 5.34 (1H, td, J=17.2, 1.2 Hz), 5.22 (1H, d, J=11.4 Hz), 4.24 (2H, d, J=6.0 Hz), 4.09 (2H, d, J=5.6 Hz). $^{13}$C NMR (100 MHz; CDCl$_3$) δ 138.3, 134.9, 132.7, 131.7 (3C), 130.5, 128.6, 128.5 (2C), 128.2, 127.5, 125.3, 123.5, 122.1, 117.3, 94.2, 88.0, 71.3, 71.0. HRMS (EI): calcd for C$_{20}$H$_{18}$O [M]+274.1358, found 274.1354. IR (neat, cm$^{-1}$): 3059, 2849, 1492, 1069.

Example 9. Scheme G: AIBN/Bu$_3$SnH Cyclization

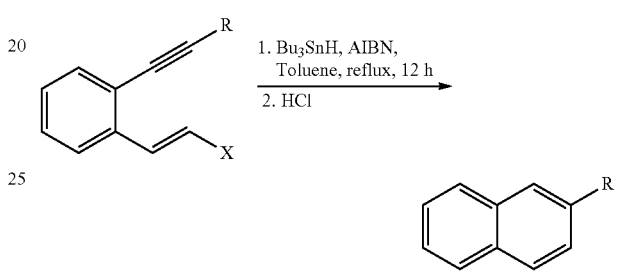

The starting enyne (0.34 mmol) was degassed in 4 mL of toluene and heated to reflux. Two separate solutions of AIBN (0.5 eq.) and Bu$_3$SnH (1.2 eq.) in 3 mL toluene were added using syringe pump through the top of a condenser over the course of 4 hours into the refluxing solution. The reaction was allowed to stir at reflux. After completion, confirmed by TLC, the solvent was evaporated and the product was dissolved in 20 mL DCM and washed with a 2M HCl solution to hydrolyze the tin. The product was purified on silica gel using a gradient of hexanes followed by ethyl acetate:hexane eluent.

Compound 3: 2-phenylnaphthalene

Chromatographic purification (hexane) afforded compound 3 as a white solid; m.p. 105-106° C.; Rf=0.5 (hexane); $^1$H NMR (600 MHz; CDCl$_3$) δ 8.06 (1H, s), 7.94-7.88 (3H, m), 7.78-7.74 (3H, m), 7.54-7.50 (4H, m), 7.40 (1H, t, J=7.3 Hz). $^{13}$C NMR (150 MHz; CDCl$_3$) δ 141.3, 38.8, 133.8, 132.8, 129.1 (2C), 128.6, 128.4, 127.8, 127.6 (2C), 127.5, 126.5, 126.1, 126.0, 125.8. HRMS (EI): calcd for C$_{16}$H$_{12}$ [M]+204.0939, found 204.0938. IR (neat, cm$^{-1}$): 3056, 2921, 1947, 1453.

Example 10. Procedure for the Synthesis of Compound M3

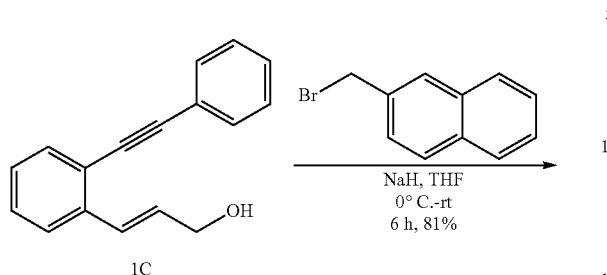

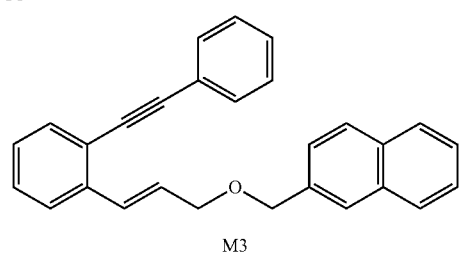

Allylation of Enyne Alcohol 1C (M3):

To a suspension of NaH (60% dispersion in mineral oil) in THF (20 mL) was added enyne alcohol 1C (0.5 g, 2.3 mmol) at rt. The mixture was stirred for 100 min at rt, after which 2-(bromomethyl)naphthalene (1.0 equiv) was added in one portion. The mixture was stirred for 6 hours at room temperature, then filtrated through a pad of silica gel. The solid was washed using hexane/AcOEt (1/1) as the eluent, and the filtrate was concentrated and purified by silica gel column chromatography, using 10% Ethyl acetate in hexane as the eluent, to afford the title compound M3 (81% yield) as yellow oil.

Compound M3: (E)-2-(((3-(2-(phenylethynyl)phenyl)allyl)oxy)methyl)naphthalene

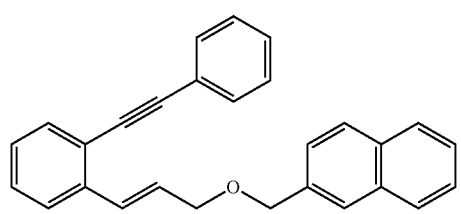

Chromatographic purification (10% ethyl acetate in hexane) afforded compound M3 (81% yield) as a yellow oil.; Rf=0.6 (10% ethyl acetate in hexane); $^1$H NMR (400 MHz; CDCl$_3$) δ 7.89-7.83 (4H, m), 7.67-7.50 (7H, m), 7.39-7.29 (6H, m), 6.54 (1H, td, J=16.0, 5.8 Hz), 4.82 (2H, s), 4.37 (2H, dd, J=5.8, 1.1 Hz). $^{13}$C NMR (100 MHz; CDCl$_3$) δ 138.3, 135.9, 133.5, 133.1, 132.7, 131.7 (2C), 130.5, 128.6, 128.5 (2C), 128.3, 128.2, 128.1, 127.8, 127.5, 126.6, 126.2, 126.0 (2C), 125.3, 123.4, 122.194.3, 88.0, 72.3, 70.9. HRMS (EI): calcd for C$_{28}$H$_{22}$O[M]+ 374.1671, found 374.1670.

2-((2-methoxyethoxy)methyl)-3-phenylnaphthalene (M6)

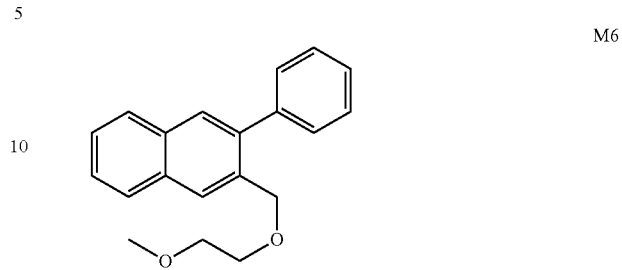

Chromatographic purification (5% ethyl acetate in hexane) afforded compound M6 (56% yield) as a pale-yellow oil. Rf=0.5 (5% ethyl acetate in hexane); 1H NMR (400 MHz; CDCl3) δ 8.03 (1H, s), 7.90-7.87 (1H, m), 7.84-7.80 (1H, m), 7.74 (1H, s), 7.50-7.44 (5H, m), 7.43-7.40 (1H, m), 4.60 (2H, s), 3.61-3.69 (2H, m), 3.57-3.54 (2H, m), 3.39 (3H, s). $^{13}$C NMR (100 MHz; CDCl$_3$) δ 141.0, 140.1, 134.0, 132.9, 132.8, 129.6 (2C), 129.0, 128.3 (2C), 128.1, 128.0, 127.8, 127.4, 126.4, 126.2, 72.1, 72.6, 69.8, 59.2. HRMS (EI): calcd for C$_{20}$H$_{20}$O$_2$[M]+292.1463, found 292.1459.

Example 11. Procedure for the Synthesis of Compound M5

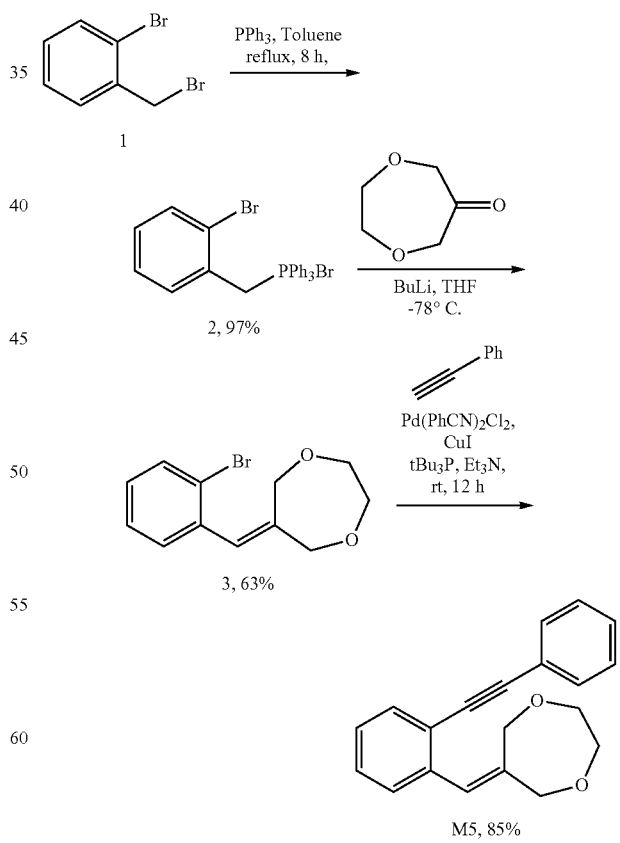

Preparation of Wittig Salt—Bromo(2-bromobenzyl)triphenyl-λ$^5$-Phosphane

Bromobenzylbromide (2.49 g, 10.0 mmol) was added dropwise into a solution of triphenylphosphine (2.62 g, 10.0 mmol) in toluene in a pressure tube at room temperature. It was stirred for 8 h at 120° C. The separated solid was filtered through a Buchner funnel and the residue was washed with hexane. The resulting white solid was recrystallized from distilled petroleum ether (60-80° C.). Yield: 4.96 g, 97%.

Wittig Reaction

To a solution of the Wittig salt bromo(2-bromobenzyl) triphenyl-λ⁵-phosphane (3.6 g, 7 mmol) in anhydrous THF (10 mL) at −78° C. was added slowly n-BuLi (7 mL of a 1.0 M solution in hexane, 7.0 mmol). After 30 min, a solution of 1,4-dioxepan-6-one (0.812 g, 7.0 mmol) in THF (10 mL) was added dropwise. The resulting solution was stirred for 1 h at −78° C. and then at room temperature for 12 h and quenched with saturated NH$_4$Cl solution. The aqueous phase was extracted with Et$_2$O (3×30 mL), and the combined organic layers were washed with brine, dried over anhydrous Na$_2$SO$_4$, and evaporated under reduced pressure. The crude was purified by column chromatography (hexane) on silica gel affording 3 as colorless oil (1.18 g, 63%).

Sonogashira Cross Coupling of Aryl Bromide 3 with Phenylacetylene (M5):

A suspension of aryl bromide 3 (0.605 g, 2.25 mmol), PdCl$_2$(PhCN)$_2$ (0.11 mmol), Cu(I) iodide (0.11 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.22 mmol in a 10% solution of toluene) was added, immediately followed by 1.2 equiv. of phenylacetylene (2.7 mmol) using a syringe. The mixture was allowed to react for 8 hours and monitored by TLC. After total consumption of the aryl bromide, the reaction mixture was filtered through celite and extracted with DCM (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compounds M5 (0.554 g, 85%) as brown oil.

Compound 3:
6-(2-bromobenzylidene)-1,4-dioxepane

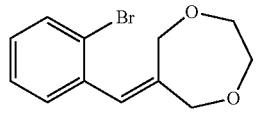

3

Chromatographic purification (5% ethyl acetate in hexane) afforded compound 3 (63% yield) as a colorless oil. Rf=0.5 (5% ethyl acetate in hexane); 1H NMR (400 MHz; CDCl3) δ 7.56 (1H, dd, J=8.0, 0.6 Hz), 7.29-7.24 (2H, m), 7.13-7.08 (1H, m), 6.53 (1H, s), 4.44 (2H, d, J=0.4 Hz), 4.36 (2H, d, J=1.0 Hz), 3.77 (4H, s). $^{13}$C NMR (100 MHz; CDCl$_3$) δ 142.0, 136.3, 132.7, 130.6, 128.9, 127.7, 127.2, 123.8, 74.4, 73.9, 72.7, 72.0. HRMS (ED: calcd for C$_{12}$H$_{13}$BrO$_2$ [M]+ 268.0099, found 268.0096.

Compound M5:
6-(2-(phenylethynyl)benzylidene)-1,4-dioxepane

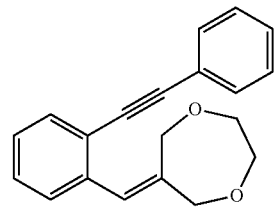

M5

Chromatographic purification (5% ethyl acetate in hexane) afforded compound M5 (85% yield) as a brown oil. Rf=0.5 (5% ethyl acetate in hexane); 1H NMR (400 MHz; CDCl3) δ 7.58-7.54 (3H, m), 7.39-7.34 (3H. m), 7.29-7.33 (2H, m), 7.28-7.24 (1H, m), 6.90 (1H, s), 4.52 (2H, d, J=1.3H), 4.51 (2H, s), 3.81 (4H, s).). $^{13}$C NMR (100 MHz; CDCl$_3$) δ 141.9, 138.1, 132.3, 1311.6 (2H, 128.9, 128.5 (2H), 128.2, 127.2, 127.0, 123.3, 122.7, 94.4, 88.1, 75.8, 74.0, 72.6, 70.4. HRMS (ED: calcd for C$_{20}$H$_{18}$O$_2$[M]+ 290.1307, found 290.1302.

Example 12. General Procedure for the Synthesis of Enynes

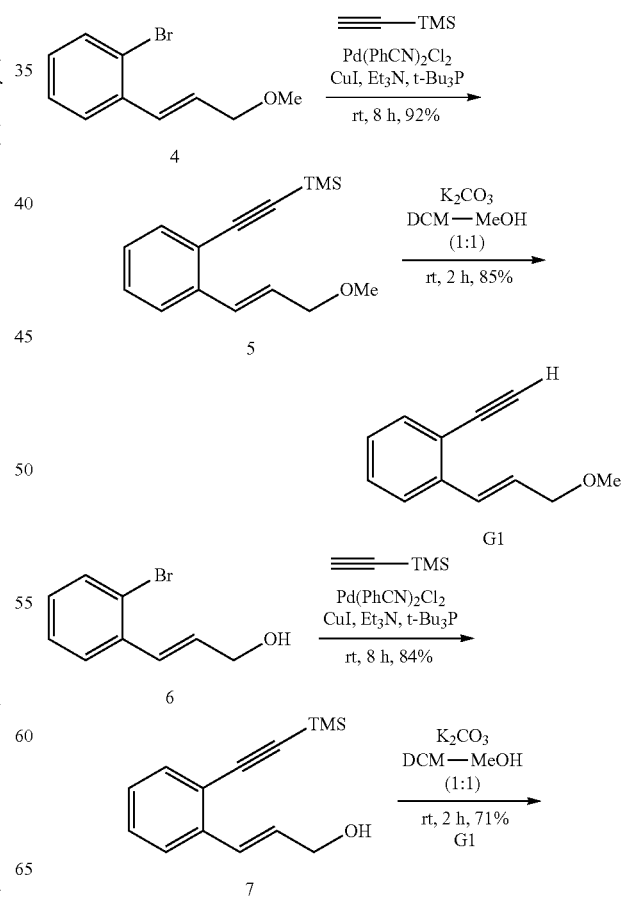

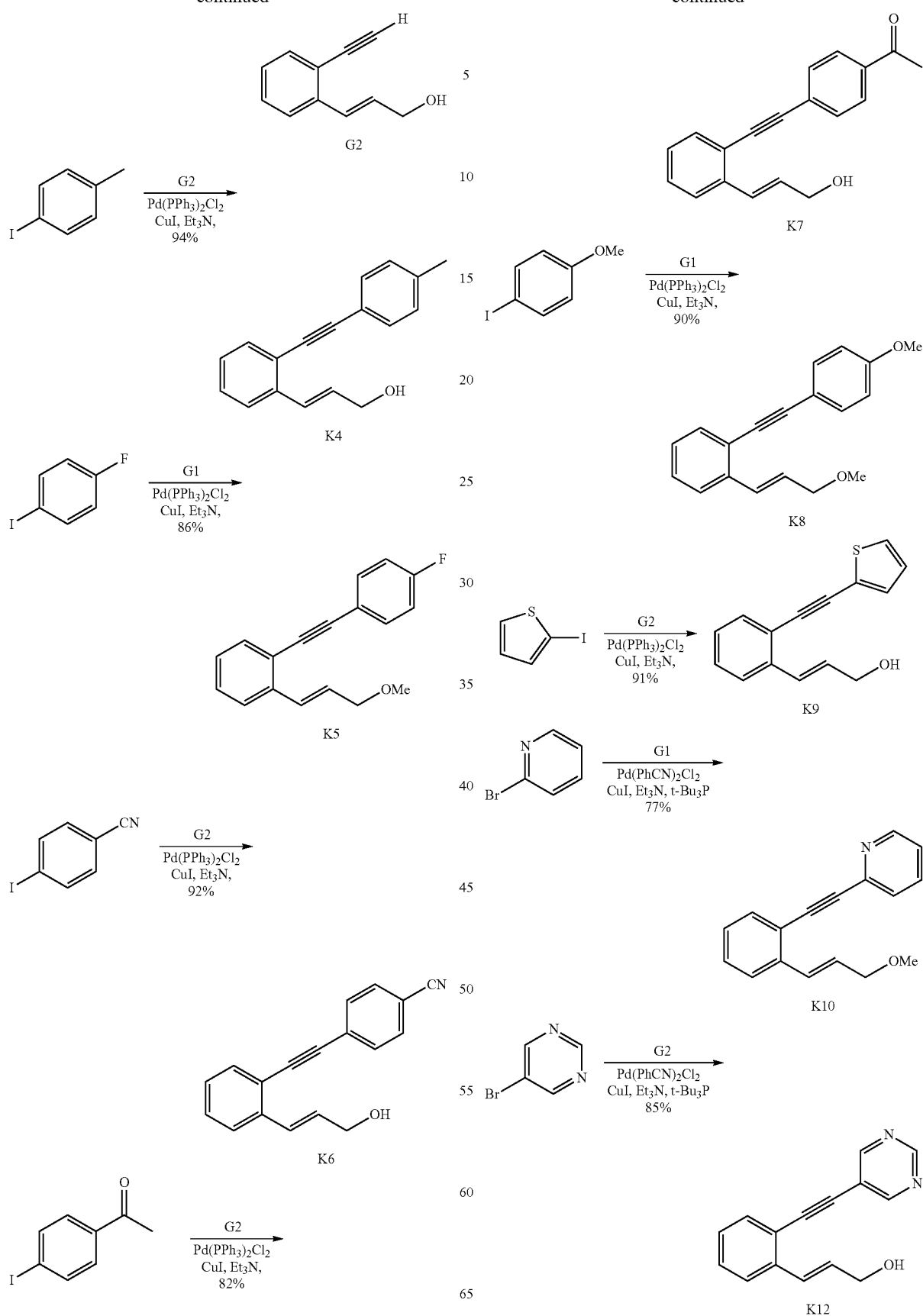

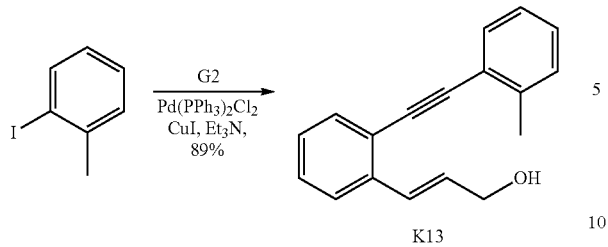

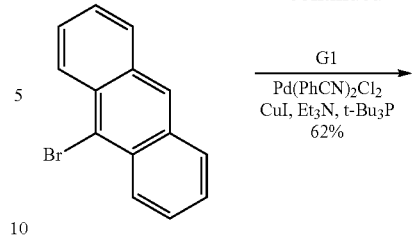

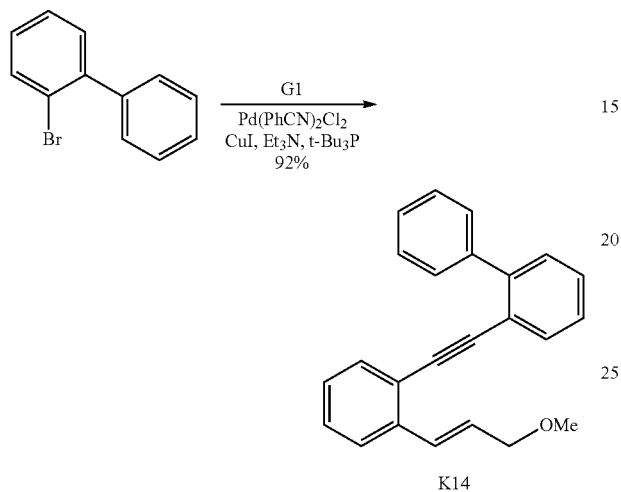

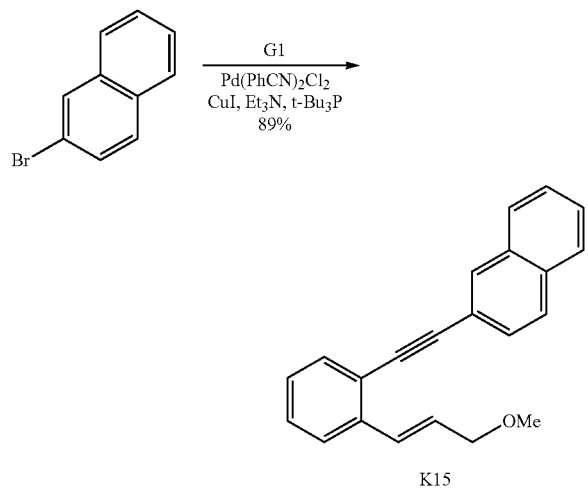

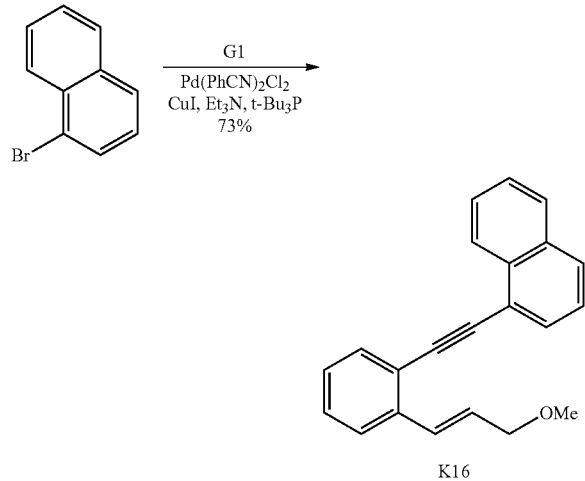

Sonogashira Cross Coupling of Aryl Bromide (4, 6) with TMS-Acetylene (5, 7):

A suspension of aryl bromide (4.5 mmol), PdCl$_2$(PhCN)$_2$ (0.23 mmol), Cu(I) iodide (0.23 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.45 mmol in a 10% solution of toluene) was added, immediately followed by 1.2 equiv. of acetylene (5.4 mmol) using a syringe. The reaction was allowed to react for 8 hours and monitored by TLC. After total consumption of the aryl bromide, the reaction mixture was filtered through celite and extracted with methylene chloride (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compounds 5 and 7 (92% and 84%) as brown oils.

Removal of TMS (G1, G2):

To a solution of enyne 5 and 7 (3.8 mmol) in MeOH-DCM (1:1, 10 mL), was added K$_2$CO$_3$ (0.54 mmol). The solution was stirred at room temperature for 2 h under argon. Water was added to quench the reaction and an aqueous work-up was performed. The reaction mixture was purified by flash chromatography (eluent: hexane/ethyl acetate) on silica gel to afford compound G1 and G2 in 85% and 71% yield as yellow oils which were then used in subsequent Sonogashira reactions with Bromo and Iodo aryl compounds Sonogashira Cross Coupling of Aryl Bromides with Acetylenes G1 and G2 (K10, K14-K17):

A suspension of aryl bromide (4.5 mmol), PdCl$_2$(PhCN)$_2$ (0.23 mmol), Cu(I) iodide (0.23 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.45 mmol in a 10% solution of toluene) was added, immediately followed by 1.0 equiv. of acetylene (5.4 mmol) solution in dry THF using a syringe. The reaction was allowed to react for 12 hours and monitored by TLC. After total consumption of the aryl bromide, the reaction mixture was filtered through celite and extracted with methylene chloride (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compounds K10, K14-K17.

Sonogashira Cross Coupling of Aryl Iodide with Acetylenes G1 and G2 (K4-9, K13):

A suspension of aryl iodide (3.5 mmol), PdCl$_2$(PPh$_3$)$_2$ (0.23 mmol), Cu(I) iodide (0.23 mmol) in 18 mL of triethylamine was degassed three times with freeze/pump/thaw technique in a flame-dried round bottom flask. Then 1.0 equiv. of acetylene (3.5 mmol) solution in dry THF using a syringe. The reaction was allowed to react for 8 hours and monitored by TLC. After total consumption of the aryl iodide, the reaction mixture was filtered through celite and extracted with methylene chloride (3×30 mL). The organic layer was washed with a saturated solution of ammonium chloride (2×30 mL), water (2×30 mL) and dried over anhydrous Na$_2$SO$_4$. Solvent was removed in vacuo. The reaction mixture was purified by flash chromatography on silica gel, (eluent: hexane/EtOAc) to afford compounds K4-9, K13.

Compound 5: (E)-((2-(3-methoxyprop-1-en-1-yl)phenyl)ethynyl)trimethylsilane

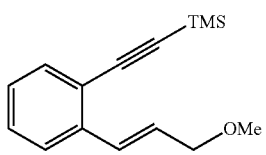

Chromatographic purification (3% ethyl acetate in hexane) afforded compound 5 (92% yield) as a brown oil. Rf=0.5 (3% ethyl acetate in hexane); $^1$H NMR (400 MHz; CDCl$_3$) δ 7.53 (1H, d, J=7.7 Hz), 7.45 (1H, dd, J=7.6, 1.0 Hz), 7.29-7.21 (1H, m), 7.17 (1H, dd, J=7.6, 1.1 Hz), 7.12 (1H, d, J=16.0 Hz), 6.35 (1H, td, J=16.0, 6.0 Hz), 4.13 (2H, dd, J=6.0, 1.5 Hz), 3.41 (3H, s), 0.28 (9H, s).). $^{13}$C NMR (100 MHz; CDCl$_3$) δ 138.7, 132.9, 130.6, 128.8, 128.0, 127.4, 125.2, 122.0, 103.6, 99.4, 73.4, 58.1, 0.1 (3C). HRMS (EI): calcd for C$_{15}$H$_{20}$OSi [M]+224.1283, found 224.1281. IR (neat, cm$^{-1}$): 3039, 1488, 1070.

Compound G1: (E)-1-ethynyl-2-(3-methoxyprop-1-en-1-yl)benzene

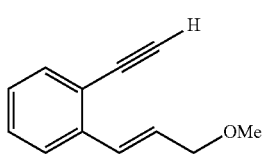

Chromatographic purification (5% ethyl acetate in hexane) afforded compound G1 (85% yield) as a yellow oil. Rf=0.5 (5% ethyl acetate in hexane); $^1$H NMR (400 MHz; CDCl$_3$) δ 7.56 (1H, d, J=7.8 Hz), 7.49 (1H, dd, J=7.7, 1.1 Hz), 7.31 (1H, t, J=7.5 Hz), 7.19 (1H, dt, J=8.0, 0.9 Hz), 7.12 (1H, d, J=16.0 Hz), 6.36 (1H, td, J=16.0, 6.0 Hz), 4.13 (2H, dd, J=6.0, 1.4 Hz). 3.40 (3H, s), 3.33 (1H, s). $^{13}$C NMR (100 MHz; CDCl$_3$) δ 138.9, 133.3, 130.3, 129.1, 128.4, 127.4, 125.2, 120.9, 82.1 (2C), 73.3, 58.2. HRMS (ED: calcd for C$_{12}$H$_{12}$O [M]+172.0888, found 172.0884. IR (neat, cm$^{-1}$): 3299, 3020, 1497, 1011.

Compound G2: (E)-3-(2-ethynylphenyl)prop-2-en-1-ol

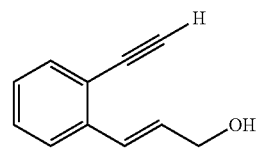

Chromatographic purification (15% ethyl acetate in hexane) afforded compound G2 (71% yield) as a yellow viscous oil. Rf=0.5 (5% ethyl acetate in hexane); $^1$H NMR (600 MHz; CDCl$_3$) δ 7.51 (1H, d, J=7.9 Hz), 7.47 (1H, d, J=7.7 Hz), 7.27 (1H, t, J=7.6 Hz), 7.18 (1H, t, J=7.5 Hz), 7.10 (1H, d, J=16.0 Hz), 6.41 (1H, dt, J=16.0, 5.5 Hz), 4.33 (2H, d, J 5.5 Hz), 3.33 (1H, s), 2.56 (1H, bs). $^{13}$C NMR (150 MHz; CDCl$_3$) δ 138.8, 133.3, 131.0, 129.1, 128.6, 127.4, 125.1, 120.8, 82.2, 82.1, 63.7. HRMS (ED: calcd for C$_{11}$H$_{10}$O[M]+ 158.0732, found 158.0727.

Compound K4: (E)-3-(2-(p-tolylethynyl)phenyl)prop-2-en-1-ol

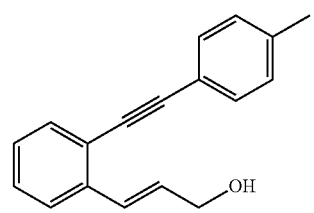

Chromatographic purification (15% ethyl acetate in hexane) afforded compound K4 (94% yield) as a brown liquid. Rf=0.6 (15% ethyl acetate in hexane); $^1$H NMR (400 MHz; CDCl$_3$) δ 7.57-7.48 (4H, m), 7.28-7.16 (5H, m), 6.46 (1H, dt, J=16.0, 5.3 Hz), 4.39 (2H, d, J 5.3 Hz), 3.49 (1h, bs), 2.36 (3H, s). $^{13}$C NMR (100 MHz; CDCl$_3$) δ 138.2, 137.8, 132.1, 131.1 (2C), 130.4, 128.9 (2C), 128.3, 128.0, 126.9, 124.8, 121.7, 119.6, 94.1, 87.0, 63.2, 21.2. HRMS (EI): calcd for C$_{18}$H$_{16}$O[M]+ 248.1201, found 248.1198. IR (neat, cm$^{-1}$): 3560 (b), 3022, 2978, 1444, 781.

Compound K5: (E)-1-((4-fluorophenyl)ethynyl)-2-(3-methoxyprop-1-en-1-yl)benzene

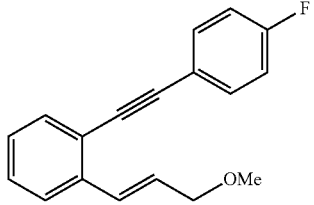

Chromatographic purification (5% ethyl acetate in hexane) afforded compound K5 (86% yield) as a dark-brown oil. Rf=0.6 (10% ethyl acetate in hexane); $^1$H NMR (400 MHz; CDCl$_3$) δ 7.60-7.52 (4H, m), 7.32-7.18 (3H, m), 7.10-7.04 (2H, m), 6.42 (1H, dt, J=16.0, 6.0 Hz), 4.17 (2H, dd, J=6.0, 1.52 Hz), 3.43 (3H, s). $^{13}$C NMR (100 MHz; CDCl$_3$) δ 162.6 (d, J 248.3 Hz), 138.3, 133.5 (2C, d, J=8.3 Hz), 132.6, 130.3, 128.6, 128.2, 127.4, 125.3, 121.8, 119.5, 135.7 (2C, d, J=21.9 Hz), 93.1, 87.7, 73.3, 58.1. HRMS (EI: calcd for C$_{18}$H$_{15}$FO[M]+266.1107, found 266.1103. IR (neat, cm$^{-1}$): 3057, 2890, 1421, 790.

Compound K6: (E)-4-((2-(3-hydroxyprop-1-en-1-yl)phenyl)ethynyl)benzonitrile

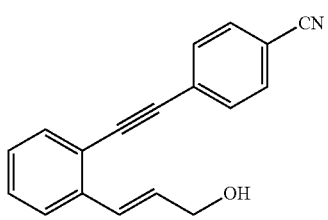

Chromatographic purification (10% ethyl acetate in hexane) afforded compound K6 (92% yield) as a yellow solid. m. p. 157° C.; Rf=0.5 (15% ethyl acetate in hexane); $^1$H NMR (400 MHz; CDCl$_3$) δ 7.61-7.60 (4H, m), 7.57 (1H, d, J=8.3 Hz), 7.52 (1H, dd, J=7.7, 1.1 Hz), 7.33 (1H, dt, J=7.59, 1.2 Hz), 7.24 (1H, dt, J=7.6, 1.2 Hz), 7.13 (1H, d, J=16.0 Hz), 7.47 (1H, dt, J=16.0, 5.5 Hz), 4.38 (2H, dd, J=5.5, 1.6 Hz). $^{13}$C NMR (100 MHz; CDCl$_3$) δ 138.4, 132.7, 132.0 (2C), 131.9 (2C), 131.1, 129.3, 128.2, 128.1, 127.4, 125.2, 120.7, 118.4, 111.4, 92.2, 92.1, 63.6. HRMS (EI: calcd for C$_{18}$H$_{13}$NO[M]+ 259.0997, found 259.0992. IR (neat, cm$^{-1}$): 3566 (b), 3095, 2709, 2276, 1482.

Compound K7: (E)-1-(4-((2-(3-hydroxyprop-1-en-1-yl)phenyl)ethynyl)phenyl)ethan-1-one

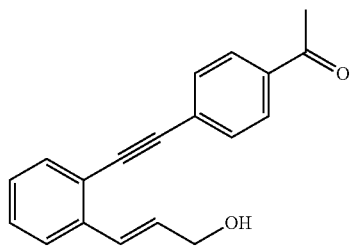

Chromatographic purification (10% ethyl acetate in hexane) afforded compound K7 (82% yield) as a brown oil. Rf=0.4 (15% ethyl acetate in hexane); $^1$H NMR (400 MHz; CDCl$_3$) δ 7.93 (2H, d, J=8.4 Hz), 7.61 (2H, d, J=8.0 Hz), 7.57 (1H, d, J=7.7 Hz), 7.53 (1H, d, J=7.7 Hz), 7.33 (1H, t, 7.5 Hz), 7.24 (1H, t, J=7.6 Hz), 7.17 (1H, d, J=16.0 Hz), 6.48 (1H, dt, J=16.0, 5.6 Hz), 4.39 (2H, d, J=5.6 Hz), 2.60 (3H, s). $^{13}$C NMR (100 MHz; CDCl$_3$) δ 197.6, 138.5, 132.8, 131.7 (2C), 131.2, 129.2, 128.5, 128.4 (2C), 128.3, 127.5, 125.3, 121.3, 93.3, 91.3, 63.8, 26.7.23 HRMS (EI): calcd for C$_{19}$H$_{16}$O$_2$[M]+ 276.1150, found 276.1148. IR (neat, cm$^{-1}$): 3456 (b), 3091, 2813, 1756.

Compound K8: (E)-1-((4-methoxyphenyl)ethynyl)-2-(3-methoxyprop-1-en-1-yl)benzene

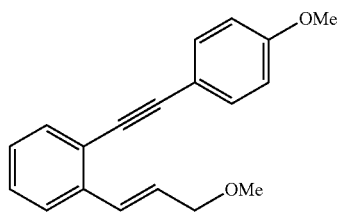

Chromatographic purification (5% ethyl acetate in hexane) afforded compound K8 (90% yield) as a yellow semisolid. Rf=0.6 (10% ethyl acetate in hexane); $^1$H NMR (400 MHz; CDCl$_3$) δ 7.57 (1H, dd, J=7.9, 1.3 Hz), 7.51-7.45 (3H, m), 7.29 (1H, dd, J=7.6, 1.5 Hz), 7.23-7.16 (2H, m), 6.91-6.87 (2H. m), 6.39 (1H, dt, J=16.0 Hz), 4.16 (2H, dd, J=5.6, 1.5 Hz). 3.84 (3H, s), 3.41 (3H, s). $^{13}$C NMR (100 MHz; CDCl$_3$) δ 159.9, 138.1, 133.2 (2C), 132.6, 130.9, 128.3, 127.9, 127.5, 125.4, 115.7, 114.3 (2C), 94.3, 86.7, 73.5, 58.2, 55.5. HRMS (EI): calcd for C$_{19}$H$_{18}$O$_2$ [M]+ 278.1307, found 278.1305. IR (neat, cm$^{-1}$): 3075, 2998, 1523, 976.

Compound K9: (E)-3-(2-(thiophen-2-ylethynyl)phenyl)prop-2-en-1-ol

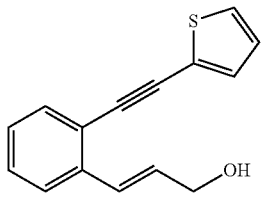

Chromatographic purification (20% ethyl acetate in hexane) afforded compound K9 (91% yield) as a yellow oil. Rf=0.5 (20% ethyl acetate in hexane); $^1$H NMR (400 MHz; CDCl$_3$) δ 7.55 (1H, d, J=7.7 Hz), 7.50 (1H, d, J=7.6 Hz), 7.31-7.7.27 (3H, m), 7.26-7.21 (1H, m), 7.12 (1H, d, J=15.8 Hz), 7.03-7.01 (1H, m), 6.46 (1H, dt, J=15.8, 5.6 Hz), 4.37 (2H, d, J=5.6 Hz), 1.97 (1H, bs). $^{13}$C NMR (100 MHz; CDCl$_3$) δ 138.1, 132.5, 132.0, 130.9, 128.9, 128.8, 127.6, 127.5, 127.3, 125.3, 123.3, 121.6, 91.7, 87.4, 63.9. HRMS (ED: calcd for C$_{15}$H$_{12}$OS[M]+240.0609, found 246.0605 IR (neat, cm$^{-1}$): 3610 (b), 3075, 2811, 1498, 978.

Compound K10: (E)-2-((2-(3-methoxyprop-1-en-1-yl)phenyl)ethynyl)pyridine

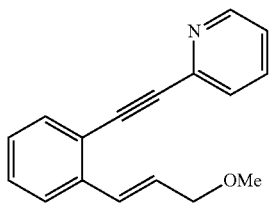

Chromatographic purification (10% ethyl acetate in hexane) afforded compound K10 (77% yield) as a yellow oil. Rf=0.5 (10% ethyl acetate in hexane); $^1$H NMR (400 MHz; CDCl$_3$) δ 8.60 (1H, d, J=4.3 Hz), 7.65 (1H, dt, J=7.6, 1.8 Hz), 7.56 (2H, d, J=7.9 Hz), 7.51 (1H, d, J=7.8 Hz), 7.30 (1H, t, J=7.1 Hz), 7.23-7.16 (3H, m), 6.38 (1H, dt, J=16.0, 6.0 Hz), 4.13 (2H, dd, J=6.0, 1.4 Hz), 3.38 (3H, s). $^{13}$C NMR (100 MHz; CDCl$_3$) δ 150.2, 143.6, 138.8, 136.3, 133.2, 130.2, 129.3, 128.5, 127.5, 127.4, 125.3, 122.9, 121.0, 93.3, 87.7, 73.3, 58.1. HRMS (ED: calcd for C$_{17}$H$_{15}$NO[M]+ 249.1154, found 249.1150. IR (neat, cm$^{-1}$): 3029, 2878, 1533, 988.

Compound K11: (E)-3-(2-(pyrimidin-5-ylethynyl)phenyl)prop-2-en-1-ol

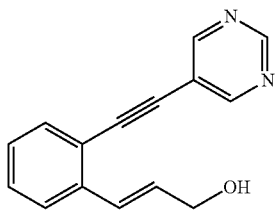

Chromatographic purification (20% ethyl acetate in hexane) afforded compound K11 (85% yield) as a brown solid. m. p. 163° C.; Rf=0.5 (25% ethyl acetate in hexane); $^1$H NMR (400 MHz; CDCl$_3$) δ 9.11 (1H, s), 8.84 (2H, s), 7.58 (1H, d, J=8.0 Hz), 7.54-7.50 (1H, m), 7.35 (1H, t, J=7.4 Hz), 7.24 (1H, dt, J=7.6, 1.0 Hz), 7.12 (1H, d, J=15.9 Hz), 6.48 (1H, dt, J=15.9, 5.4 Hz), 4.39 (2H, dd, J=5.4, 1.5 Hz), 2.42 (1H, bs). $^{13}$C NMR (100 MHz; CDCl$_3$) δ 158.7 (2C), 156.8, 154.4, 138.8, 132.9, 131.8, 129.8, 128.1, 127.6, 125.5, 120.4, 95.1, 86.9, 63.3. HRMS (ED: calcd for C$_{15}$H$_{12}$N$_2$O[M]+ 236.0950, found 236.0944. IR (neat, cm$^{-1}$): 3560 (b), 3075, 2811, 1498, 978.

Compound K13: (E)-3-(2-(o-tolylethynyl)phenyl)prop-2-en-1-ol

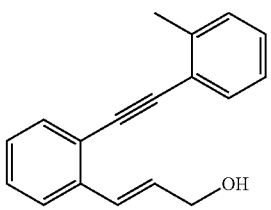

Chromatographic purification (15% ethyl acetate in hexane) afforded compound K13 (89% yield) as a brown oil. Rf=0.6 (15% ethyl acetate in hexane); $^1$H NMR (400 MHz; CDCl$_3$) δ 7.57 (1H, d, J=7.9 Hz), 7.53 (1H, t, J=7.0 Hz), 7.29 (1H, t, J=7.5 Hz), 7.26-7.22 (5H, m), 7.20-7.18 (1H, m), 6.46 (1H, dt, J=16.0, 5.4 Hz), 4.36 (2H, d, J=5.4 Hz), 2.54 (3H, s), 2.21 (1H, bs). $^{13}$C NMR (100 MHz; CDCl$_3$) δ 162.6 (d, J=248.3 Hz), 140.2, 138.2, 132.7, 132.0, 130.8, 129.7, 129.2, 128.6 (2C), 127.5, 125.8, 15.2, 123.2, 122.4, 93.3, 91.9, 63.9, 21.12. HRMS (ED: calcd for C$_{18}$H$_{16}$O[M]+ 248.1201, found 248.1200. IR (neat, cm$^{-1}$): 3029, 2993, 1439, 778.

Compound K14: (E)-2-((2-(3-methoxyprop-1-en-1-yl)phenyl)ethynyl)-1,1'-biphenyl

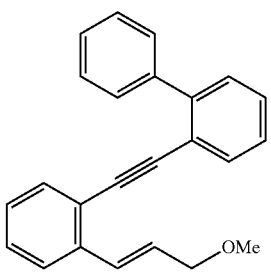

Chromatographic purification (5% ethyl acetate in hexane) afforded compound K14 (92% yield) as a yellow oil. Rf=0.5 (5% ethyl acetate in hexane); $^1$H NMR (400 MHz; CDCl$_3$) δ 7.71-7.67 (2H, m), 7.54 (1H, d, J=7.5 Hz), 7.47-7.35 (9H, m), 7.26 (1H, t, J=6.2 Hz), 7.19 (1H, dt, J=7.6, 0.9 Hz), 6.86 (1H, d, J=16.0 Hz), 6.30 (1H, dt, J=16.0, 6.2 Hz), 4.00 (2H, dd, J=6.2, 1.2 Hz), 3.38 (3H, s). $^{13}$C NMR (100 MHz; CDCl$_3$) δ 143.9, 140.8, 138.1, 134.0, 133.8, 133.3, 132.7, 130.8, 129.8, 129.5 (2C), 128.8, 128.5, 128.2

(2C), 127.9, 127.7, 127.4, 127.3, 125.1, 122.3, 121.9, 94.00, 90.8, 73.3, 58.0, HRMS (EI): calcd for $C_{24}H_{20}O$ [M]+ 324.1514, found 324.1511. IR (neat, cm$^{-1}$): 3288, 3033, 1452, 998.

Compound 15: (E)-2-((2-(3-methoxyprop-1-en-1-yl)phenyl)ethynyl)naphthalene

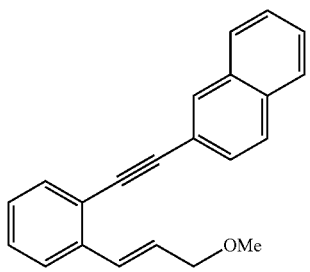

K15

Chromatographic purification (5% ethyl acetate in hexane) afforded compound K15 (89% yield) as a yellow semisolid. Rf=0.6 (10% ethyl acetate in hexane); $^1$H NMR (400 MHz; CDCl$_3$) δ 8.09 (1H, s), 7.86-7.83 (3H, m), 7.63-7.58 (3H, m), 7.53-7.50 (2H, m), 7.35-7.24 (3H, m), 6.44 (1H, dd, J=16.0, 6.0 Hz), 4.20 (2H, dd, J=6.0, 1.3 Hz), 3.46 (3H, s). $^{13}$C NMR (100 MHz; CDCl$_3$) δ 138.4, 133.2, 133.0, 132.8, 131.5, 130.6, 128.7, 128.5, 128.2, 128.1, 128.0 (2C), 127.6, 126.9, 126.8, 125.4, 122.1, 120.8, 94.7, 88.4, 73.5, 58.2. HRMS (EI): calcd for $C_{22}H_{18}O$ [M]+ 298.1358, found 298.1355. IR (neat, cm$^{-1}$): 3055, 2921, 1446, 1112.

Compound K16: (E)-1-((2-(3-methoxyprop-1-en-1-yl)phenyl)ethynyl)naphthalene

K16

Chromatographic purification (5% ethyl acetate in hexane) afforded compound K16 (73% yield) as a yellow semisolid. Rf=0.6 (10% ethyl acetate in hexane); $^1$H NMR (400 MHz; CDCl$_3$) δ 8.51 (1H, d, J=8.1 Hz), 7.88 (2H, t, J=9.0 Hz), 7.81 (1H, dd, J=7.1, 1.0 Hz), 7.68-7.61 (3H, m), 7.58-7.54 (1H, s), 7.49 (1H, dd, J=7.3, 0.9 Hz), 7.37-7.34 (2H, m), 7.30 (1H, dt, J=7.5, 1.3 Hz), 6.46 (1H, td, J=16.0, 6.0 Hz), 4.20 (2H, dd, J=6.0, 1.5 Hz). 3.45 (3H, s). $^{13}$C NMR (100 MHz; CDCl$_3$) δ 138.4, 133.4, 132.8, 130.7, 130.6, 129.0, 128.8, 128.5 (2C), 128.3, 127.6, 127.0, 126.6, 126.4, 125.5, 12504, 122.3, 121.2, 92.9, 92.4, 73.4, 58.2. HRMS (ED: calcd for $C_{22}H_{18}O$ [M]+ 298.1358, found 298.1356. IR (neat, cm$^{-1}$): 3059, 2903, 1456, 1009.

Compound K17: (E)-9-((2-(3-methoxyprop-1-en-1-yl)phenyl)ethynyl)anthracene

K17

Chromatographic purification (5% ethyl acetate in hexane) afforded compound K17 (62% yield) as a yellow semisolid. Rf=0.6 (10% ethyl acetate in hexane); $^1$H NMR (400 MHz; CDCl$_3$) δ 8.70 (2H, d, J=8.5 Hz), 8.44 (1H, s), 8.03 (2H, d, J=8.5 Hz), 7.80-7.78 (1H, m), 7.67 (1H, d, J=8 Hz), 7.61 (2H, dt, J=6.6, 1.0 Hz), 7.57-7.51 (3H, m), 7.41-7.32 (2H, m), 6.48 (1H, dt, J=15.9, 5.9 Hz), 4.23 (2H, dd, J=5.9, 1.3 Hz), 3.46 (3H, s). $^{13}$C NMR (100 MHz; CDCl$_3$) δ 138.5, 132.8, 131.4, 130.9, 128.9, 128.5, 128.0, 127.7, 127.0, 126.8, 125.9, 125.5, 122.6, 117.6, 99.4, 91.3, 73.4, 58.3. HRMS (ED: calcd for $C_{26}H_{20}O$ [M]+ 348.1514, found 348.11511. IR (neat, cm$^{-1}$): 3088, 2828, 1466, 998.

Example 13. Procedure for the Synthesis of Compound K12

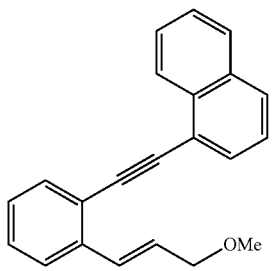

Wittig Reaction (8):

Ethyl (triphenylphosphoranylidene) acetate (2.80 g, 8.17 mmol) was added to a solution of 2-bromonicotinaldehyde (1.0 g, 5.4 mmol) in dry DCM (dichloromethane) at 0° C. and stirred for 8 h at room temperature. The solvent was then evaporated under vacuum. The colorless oil was partitioned between ethylacetate and water. The organic layer was washed with water, brine and dried over $Na_2SO_4$. It was then filtered and evaporated to give an oil from which the title compound 8 was isolated by column chromatography (Sigel, PE:EA=15:1). Yield: 1.3 g, 94%; State: colorless oil.

DIBAL-H Reduction of α,β-Unsaturated Ester 8 (9):

A THF solution of compound 8 (1.3 g, 5.2 mmol) was cooled to 0° C. Diisobutylaluminum hydride (DIBAL-H, 1.0 M in hexane, 14 mL, 14 mmol) was slowly added to this solution under a nitrogen atmosphere and was stirred for 6 h. The reaction was quenched with aq. $NH_4Cl$ sol. (20 mL) and extracted with ethyl acetate (100 mL). The extract was washed with brine solution, dried over $MgSO_4$, and concentrated under reduced pressure. The residue was eluted through a silica column to afford 9 as a colorless oil (0.930 g, 84%).

Sonogashira Cross Coupling of Aryl Bromides 9 with 2-ethynylpyridine (K12):

A suspension of aryl bromide 9 (0.480 g, 2.25 mmol), $PdCl_2(PhCN)_2$ (0.11 mmol), Cu(I) iodide (0.11 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.23 mmol in a 10% solution of toluene) was added, immediately followed by 1.0 equiv. of 2-ethynylpyridine (2.25 mmol) using a syringe. The reaction was allowed to react for 12 hours and monitored by TLC. After total consumption of the aryl bromide, the reaction mixture was filtered through celite and extracted with methylene chloride (3×30 mL). The organic layer was washed with a saturated solution of ammonium chloride, water and dried over anhydrous $Na_2SO_4$. Solvent was removed under reduced pressure. The reaction mixture was purified by flash chromatography (eluent: hexane/ethyl acetate) on silica gel to afford compound K12 (0.510 g, 96%) as brown oil.

Compound 8: ethyl (E)-3-(2-bromopyridin-3-yl)acrylate

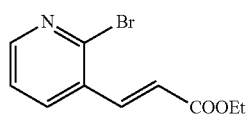

Chromatographic purification (10% ethyl acetate in hexane) afforded compound 8 (94% yield) as a colorless oil. Rf=0.7 (10% ethyl acetate in hexane); $^1$H NMR (400 MHz; $CDCl_3$) δ 8.32 (1H, dd, J=4.68, 1.9 Hz), 7.89 (1H, d, J=16.0 Hz), 7.84 (1H, dd, J=7.7, 1.9 Hz), 7.30-7.28 (1H, m), 6.38 (1H, d, J=16.0 Hz), 4.25 (2H, q, J=7.1 Hz), 1.31 (3H, t, J=7.1 Hz). HRMS (EI): calcd for $C_{10}H_{10}BrNO_2$[M]+ 258.9895, found 254.9892.

Compound 9: (E)-3-(2-bromopyridin-3-yl)prop-2-en-1-ol

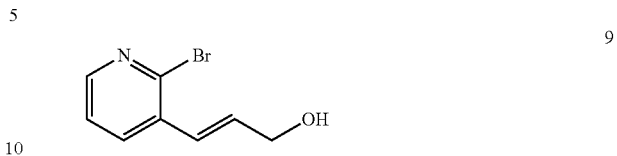

Chromatographic purification (20% ethyl acetate in hexane) afforded compound 9 (84% yield) as a colorless oil. Rf=0.3 (20% ethyl acetate in hexane); $^1$H NMR (400 MHz; $CDCl_3$) δ 8.11-8.09 (1H, m), 7.67 (1H, d, J=7.7 Hz), 7.14-7.12 (1H, m), 6.76 (1H, d, J=15.9 Hz), 6.26 (1H, dt, J=15.9, 5.1 Hz), 4.30 (2H, d, J=5.1 Hz), 3.69 (1H, bs). $^{13}$C NMR (100 MHz; $CDCl_3$) δ 148.4, 142.7, 138.7, 135.1, 134.4, 126.8, 123.2, 62.8. HRMS (EI): calcd for $C_8H_8BrNO$ [M]+ 212.9789, found 212.9787.

Compound K12: (E)-3-(2-(pyridin-2-ylethynyl)pyridin-3-yl)prop-2-en-1-ol

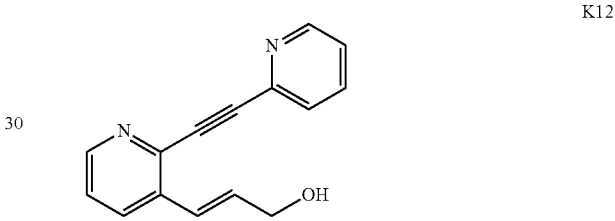

Chromatographic purification (20% ethyl acetate in hexane) afforded compound K12 (96% yield) as a Brown oil. Rf=0.3 (20% ethyl acetate in hexane); $^1$H NMR (600 MHz; $CDCl_3$) δ 8.52 (1H, d, J=7.0 Hz), 8.39 (1H, dd, J=4.5.0, 1.3 Hz), 7.74-7.73 (1H, m), 7.63-7.60 (1H, m), 7.54 (1H, d, J=7.8 Hz), 7.21-7.18 (1H, m), 7.15-7.13 (1H, m), 7.12 (1H, d, J=16.0 Hz), 6.46 (1H, dt, J=16.0, 5.0 Hz), 4.35 (2H, dd, J=5.0, 1.5 Hz). $^{13}$C NMR (150 MHz; $CDCl_3$) δ 149.9, 148.6, 142.4, 140.2, 136.6, 135.7, 135.1, 132.7, 128.0, 125.0, 123.7, 123.6, 91.7, 86.9, 62.8. HRMS (ED: calcd for $C_{15}H_{12}N_2O$[M]+ 236.0950, found 236.0944.

Example 14. Procedure for the Synthesis of Compound L1

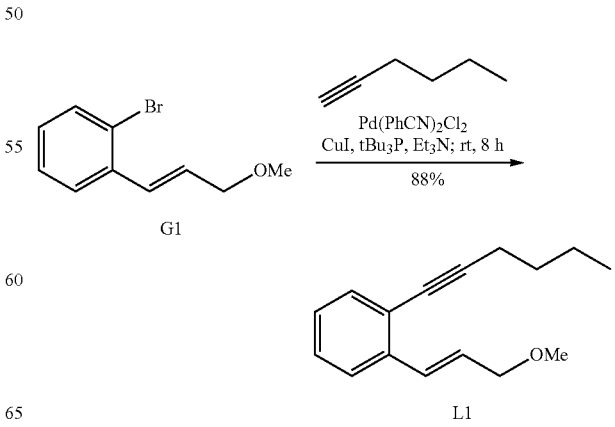

Sonogashira Cross Coupling of Aryl Bromides G1 with Hex-1-yne:

A suspension of aryl bromide G1 (0.511 g, 2.25 mmol), PdCl$_2$(PhCN)$_2$ (0.11 mmol), Cu(I) iodide (0.11 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.23 mmol in a 10% solution of toluene) was added, immediately followed by 1.0 equiv. of hex-1-yne (2.25 mmol) using a syringe. The reaction was allowed to react for 12 hours and monitored by TLC. After total consumption of the aryl bromide, the reaction mixture was filtered through celite and extracted with methylene chloride (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compound L1 (0.451 g, 88%) as brown liquid.

Compound L1: (E)-1-(hex-1-yn-1-yl)-2-(3-methoxyprop-1-en-1-yl)benzene

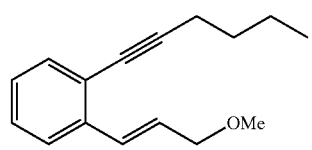

Chromatographic purification (5% ethyl acetate in hexane) afforded compound L1 (88% yield) as a brown liquid. Rf=0.5 (5% ethyl acetate in hexane); $^1$H NMR (400 MHz; CDCl$_3$) δ 7.52 (1H, d, J=7.6 Hz), 7.40-7.37 (1H, m), 7.22 (1H, t, J=7.1 Hz), 7.18-7.15 (1H, m), 7.12 (1H, d, J=16.2 Hz), 6.33 (1H, dt, J=16.2, 6.1 Hz), 4.13 (2H, dd, J=6.1, 1.3 Hz), 3.40 (3H, s), 2.48 (2H, t, J=6.9 Hz), 1.65-1.48 (4H, m), 1.0 (3H, t, J=7.2 Hz). $^{13}$C NMR (100 MHz; CDCl$_3$) δ 138.1, 132.7, 131.1, 127.8, 127.4 (2C), 125.1, 123.0, 95.5, 79.1, 73.5, 58.1, 31.0, 22.2, 19.5, 13.8. HRMS (EI): calcd for C$_{16}$H$_{20}$O[M]+ 228.1514, found 228.1511. IR (neat, cm$^{-1}$): 3022, 2978, 1444, 781.

Example 15. General Procedures for the Synthesis of Compounds L4, L4', P7

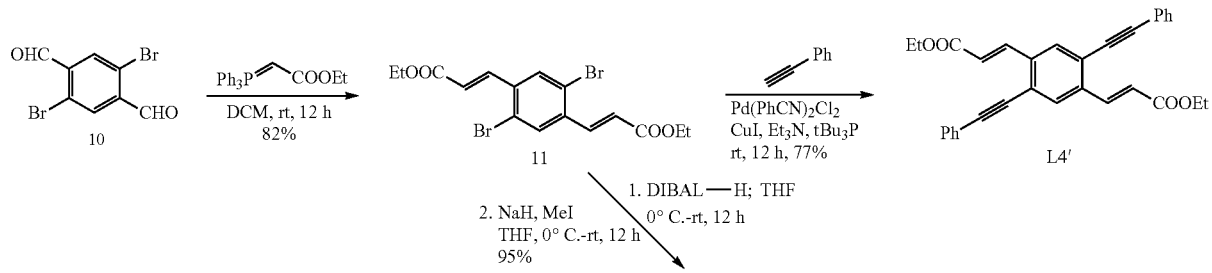

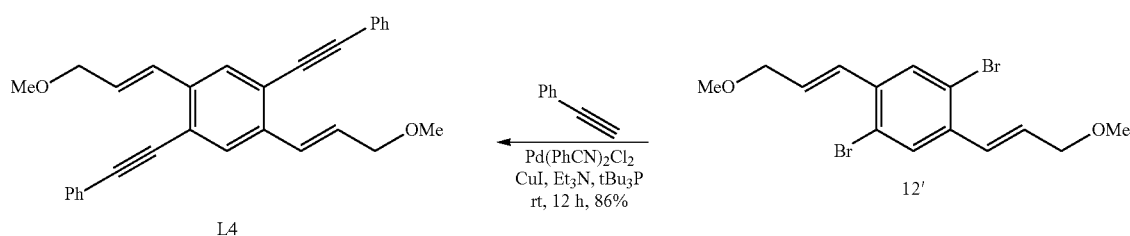

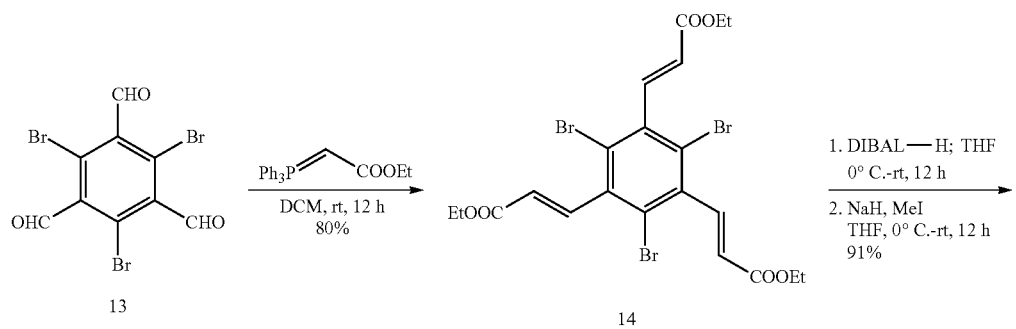

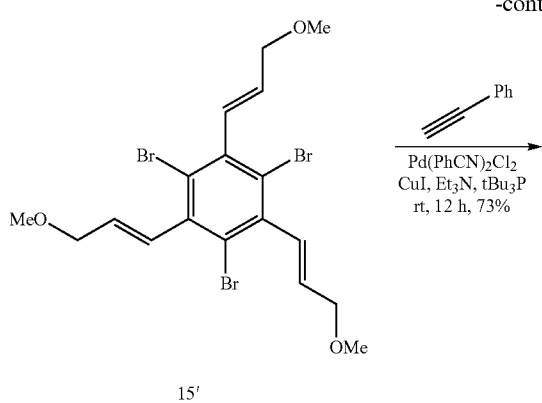
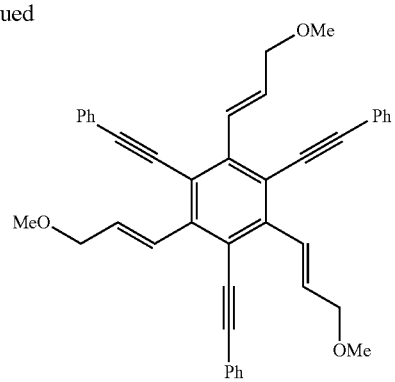

Wittig Reaction (11):

Ethyl (triphenylphosphoranylidene) acetate (1.5 eq. for each aldehyde group) was added to a solution of bromoaldehyde in dry DCM (dichloromethane) at 0° C. and stirred for 8 h at room temperature. The solvent was then evaporated under vacuum. The colorless oil was partitioned between ethylacetate and water. The organic layer was washed with water, brine and dried over $Na_2SO_4$. It was then filtered and evaporated to give an oil from which the title compound 11 was isolated by column chromatography (Si-gel, PE:EA=15:1). State: colorless viscous oil.

DIBAL-H Reduction of α,β-Unsaturated Ester 11 and 14 (12 and 15):

A THF solution of bromo ester compound (11 and 14) was cooled to 0° C. Diisobutylaluminum hydride (DIBAL-H, 1.0 M in hexane, 1 eq. for each ester group) was slowly added to this solution under a nitrogen atmosphere and was stirred for 6 h. The reaction was quenched with aq. $NH_4Cl$ sol. (20 ml) and extracted with ethyl acetate (100 ml). The extract was washed with brine solution, dried over $MgSO_4$, and concentrated under reduced pressure. The residue was directly used for the next step without further purification.

Methylation of Bromocinnamyl Alcohol (12' and 15'):

To a suspension of NaH (60% dispersion in mineral oil; 1.5 eq. for each alcohol group) in THF (20 mL) was added bromocinnamyl alcohol (Crude from the previous step) at room temperature. The mixture was stirred for 100 min at room temperature, after which MeI (3 eq. for each alcohol group) was added in one portion. The mixture was stirred for 6 h at room temperature, then filtrated through a pad of silica gel. The solid was washed using hexane/ethyl acetate (1:1) as the eluent, and the filtrate was concentrated and purified by silica gel column chromatography, using 10% ethylacetate in hexane as the eluent, to afford the title compound 12' and 15' (95% and 91% yield) as colorless oil.

Sonogashira Cross Coupling of Aryl Bromides (11, 12', 15') with Phenylacetylene (L4', L4, P7):

A suspension of aryl bromide (2.2 mmol), $PdCl_2(PhCN)_2$ (0.22 mmol for 11 and 12' and 0.33 mmol for 15'), Cu(I) iodide (0.22 mmol for 11 and 12' and 0.33 mmol for 15') in 20 mL of triethylamine was degassed three times with freeze/pump/thaw technique in a flame dried round bottom flask. Once the reaction mixture was completely thawed and the atmosphere replaced with argon, tri-tert-butylphosphine (0.44 mmol for 11 and 12' and 0.66 mmol for 15' in a 1 M solution of toluene) was added, immediately followed by phenylacetylene (5.3 mmol for 11 and 12' and 7.9 mmol for 15') using a syringe. The mixture was allowed to react for 8 hours and monitored by TLC. After total consumption of the aryl bromide, the reaction mixture was filtered through celite and extracted with DCM (3×30 mL). The organic layer was washed with a saturated solution of ammonium chloride, water and dried over anhydrous $Na_2SO_4$. Solvent was removed under reduced pressure. The reaction mixtures were purified by flash chromatography (eluent: hexane/ethyl acetate) on silica gel to afford compounds L4', L4 and, P7 in 77%, 86% and, 73% yields respectively.

Compound 11: diethyl 3,3'-(2,5-dibromo-1,4-phenylene)(2E,2'E)-diacrylate

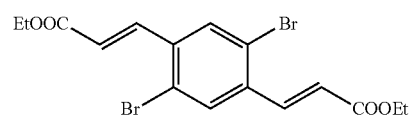

Chromatographic purification (10% ethyl acetate in hexane) afforded compound 11 (82% yield) as a gummy oil. Rf=0.3 (20% ethyl acetate in hexane); $^1$H NMR (400 MHz; $CDCl_3$) δ 7.91 (2H, d, H=15.9 Hz), 7.82 (2H, s), 6.42 (2H, d, J=15.9 Hz), 4.28 (4H, q, J=7.1 Hz), 1.34 (6H, t, J=7.1 Hz).

Compound L3: 1-((Z)-hex-1-en-1-yl)-2-((E)-3-methoxyprop-1-en-1-yl)benzene

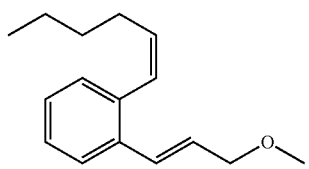

Chromatographic purification (5% ethyl acetate in hexane) afforded compound L3 (70% yield) as a yellow oil. Rf=0.5 (5% ethyl acetate in hexane); $^1$H NMR (400 MHz; $CDCl_3$) δ 7.52-7.5 (1H, m), 7.24-7.16 (3H, m), 6.79 (1H, d, J=15.9 Hz), 6.50 (1H, d, J=11.4 Hz), 6.21 (1H, dt, J=15.9, 6.0 Hz), 5.76 (1H, dt, J=11.4, 7.4 Hz), 4.10 (2H, dd, J=6.1, 1.3 Hz), 3.39 (3H, s), 2.13-2.08 (1H, m), 1.40-1.27 (4H, m), 0.85 (3H, t, J=7.2 Hz). $^{13}$C NMR (100 MHz; $CDCl_3$) δ

136.4, 135.4, 134.1, 131.1, 129.8, 127.7, 127.3, 127.2, 127.1, 125.9, 73.6, 58.1, 32.0, 28.35, 22.5, 14.1. HRMS (EI): calcd for $C_{16}H_{22}O[M]+$ 230.1671, found 230.1666.23.

Compound L4': diethyl 3,3'-(2,5-bis(phenylethynyl)-1,4-phenylene)(2E,2'E)-diacrylate

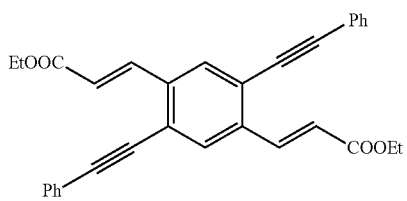

Chromatographic purification (10% ethyl acetate in hexane) afforded compound L4' (63% yield) as a brown semisolid. Rf=0.3 (20% ethyl acetate in hexane); $^1$H NMR (400 MHz; CDCl$_3$) δ 8.22 (2H, d, J=15.9 Hz), 7.85 (1H, s), 7.61-7.59 (4H, m), 7.40-7.38 (6H, m), 6.65 (2H, d, J=15.9 Hz), 4.29 (4H, q, J=7.1 Hz), 1.36 (6H, t, J=7.1 Hz). $^{13}$C NMR (100 MHz; CDCl$_3$) δ 166.5 (2C), 140.9 (2C), 136.6 (2C), 131.7 (4C), 130.5 (2C), 129.0 (2C), 128.5 (4C), 123.9 (2C), 122.4 (2C), 121.3 (2C), 97.3 (2C), 86.4 (2C), 60.7 (2C), 14.3 (2C). HRMS (EI): calcd for $C_{32}H_{26}O_4[M]+$ 474.1831, found 474.1828. IR (neat, cm$^{-1}$): 3029, 1745.

Compound L5: diethyl 2,2'-(2,6-diphenyl-1,5-dihydro-s-indacene-1,5-diyl)diacetate

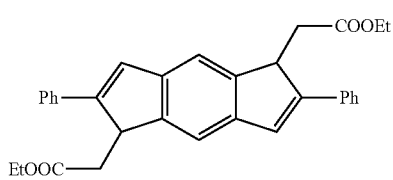

Chromatographic purification (10% ethyl acetate in hexane) afforded compound L5 (20% yield) as a yellow solid. m. p. 93-94° C. Rf=0.3 (20% ethyl acetate in hexane); $^1$H NMR (600 MHz; CDCl$_3$) δ 7.30 (4H, d, J=7.0 Hz), 7.49 (2H, s), 7.29 (2H, t, J=7.0 Hz), 7.11 (2H, s), 4.42 (2H, d, J=8.2 Hz), 4.26-4.15 (4H, m), 2.93 (2H, d, J=16.2 Hz), 2.22-2.16 (2H, m), 1.25 (6H, t, J=7.0 Hz). $^{13}$C NMR (100 MHz; CDCl$_3$) δ 172.9 (2C), 150.2 (2C), 147.4 (2C), 143.9 (2C), 135.0 (2C), 129.0 (4C), 127.8 (2C), 127.1 (4C), 125.3 (2C), 121.1 (2C), 60.8 (2C), 45.6 (2C), 37.0 (2C), 14.4 (2C). (HRMS (EI): calcd for $C_{32}H_{30}O_4[M]+$ 478.2144, found 478.2142.

Compound 12': 1,4-dibromo-2,5-bis((E)-3-methoxyprop-1-en-1-yl)benzene

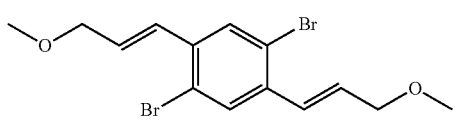

Chromatographic purification (10% ethyl acetate in hexane) afforded compound 12' as a yellow viscous oil. Rf=0.3 (10% ethyl acetate in hexane); $^1$H NMR (400 MHz; CDCl$_3$) δ 7.67 (2H, s), 6.82 (2H, d, J=15.8 Hz), 6.22 (2H, dt, J=15.8, 5.4 Hz), 4.10 (4H, dd, J=5.4, 1.4 Hz), 3.39 (6H, s). $^{13}$C NMR (150 MHz; CDCl$_3$) δ 137.3 (2C), 131.0 (2C), 130.4 (2C), 129.4 (2C), 122.6 (2C), 72.8 (2C), 58.4 (2C).

Compound L4: ((2,5-bis((E)-3-methoxyprop-1-en-1-yl)-1,4-phenylene)bis(ethyne-2,1-diyl))dibenzene

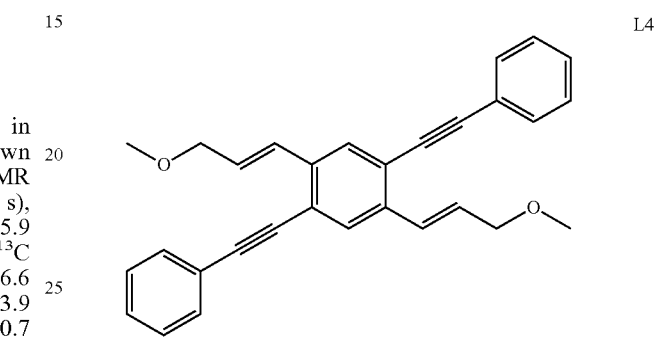

Chromatographic purification (10% ethyl acetate in hexane) afforded compound L4 (86% yield) as a yellow semisolid. Rf=0.3 (10% ethyl acetate in hexane); $^1$H NMR (400 MHz; CDCl$_3$) δ 7.75 (2H, s), 7.58-7.57 (4H, m), 7.42-7.38 (6H, m), 7.14 (2H, d, J=16.0 Hz), 6.45 (2H, dt, J=16.0, 5.4 Hz), 4.17 (4H, d, J=5.4 Hz), 3.43 (6H, s). $^{13}$C NMR (100 MHz; CDCl$_3$) δ 137.2 (2C), 131.7 (4C), 129.4 (4C), 128.8 (2C), 128.6 (4C), 123.2 (2C), 122.1 (2C), 95.5 (2C), 87.7 (2C), 73.3 (2C), 58.2 (2C). HRMS (EI): calcd for $C_{30}H_{22}O_2[M]+$ 418.1933, found 418.1930.

Compound 14: triethyl 3,3',3''-(2,4,6-tribromobenzene-1,3,5-triyl)-triacrylate

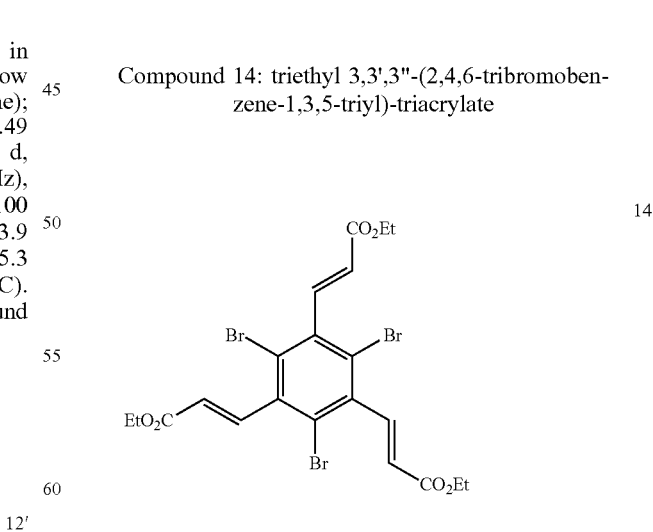

Chromatographic purification (10% ethyl acetate in hexane) afforded compound 14 (80% yield) as a pale-yellow semisolid. Rf=0.3 (10% ethyl acetate in hexane); $^1$H NMR (400 MHz; CDCl$_3$) δ 7.43 (2H, d, J=16.3 Hz), 6.10 (2H, d, J=16.3 Hz), 4.18 (4H, q, J=7.1 Hz), 1.25 (6H, t, J=7.1 Hz,).

Compound P7: ((2,4,6-tris((E)-3-methoxyprop-1-en-1-yl)benzene-1,3,5-triyl)tris(ethyne-2,1-diyl))tribenzene

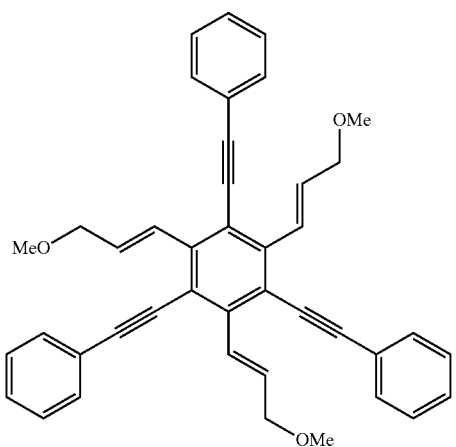

P7

Chromatographic purification (10% ethyl acetate in hexane) afforded compound P7 (73% yield) as a brown solid. Rf=0.3 m. p. 133° C. (10% ethyl acetate in hexane); $^1$H NMR (400 MHz; CDCl$_3$) δ 7.54 (6H, dd, J=6.4, 3.0 Hz), 7.42-7.34 (9H, m), 7.16 (3H, d, J=16.1 Hz), 6.85 (3H, dt, J=16.1, 5.8 Hz), 4.31-4.16 (6H, m), 3.45 (9H, s). $^{13}$C NMR (100 MHz, CDCl$_3$) δ 141.1 (3C), 133.7 (3C), 131.5 (6C), 129.6 (3C), 128.7 (3C), 128.6 (6C), 123.5 (3C), 119.6 (3C), 99.2 (3C), 87.8 (3C), 73.6 (3C), 58.0 (3C). HRMS (ED: calcd for C$_{42}$H$_{36}$O$_3$[M]+ 588.2664, found 588.2661.

Example 16. General Procedures Bu$_3$SnH/AIBN Radical Reaction

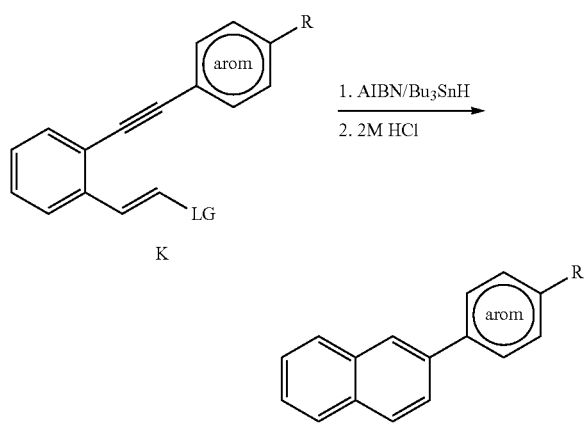

The starting enyne (K1-17) (0.34 mmol) was degassed in 4 mL of toluene and heated to reflux. Two separate solutions of AIBN (0.5 equiv.) and Bu$_3$SnH (1.2 equiv.) each in 3 mL toluene were added using syringe pump through the top of a condenser over the course of 4 hours into the refluxing solution. The reaction was stirred at reflux for 12 h. After completion, confirmed by TLC, the solvent was evaporated and the product was dissolved in 20 mL DCM and washed with a 2 M HCl solution to accomplish protodestannylation. The products were purified on silica gel using a gradient of hexanes followed by ethyl acetate:hexane eluent.

Example 17. General Procedure for Stille Coupling

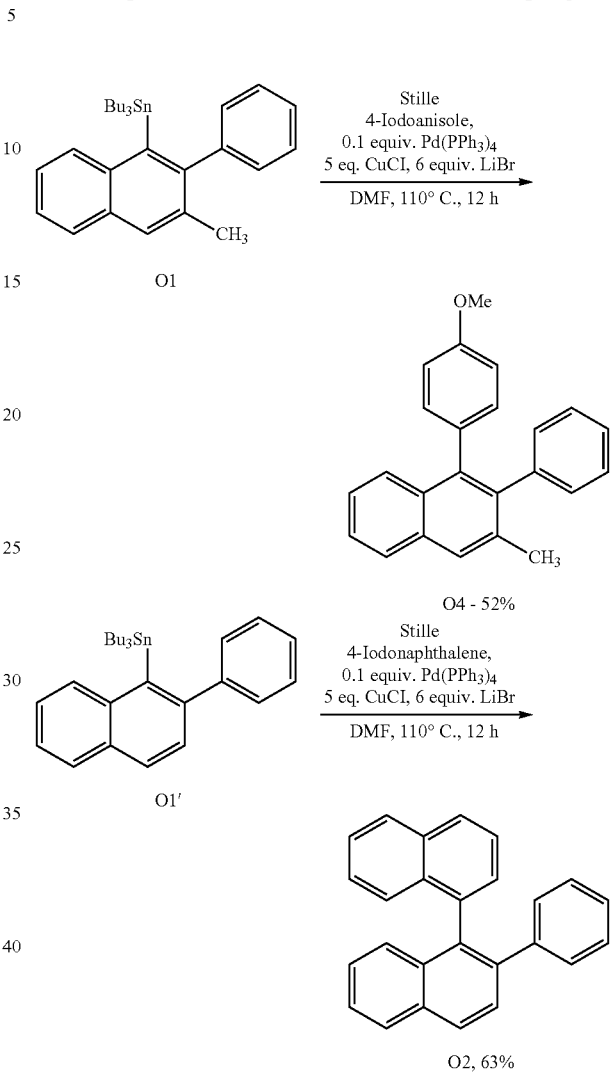

A solution of enyne (0.34 mmol) in toluene was brought to reflux. A solution of tributyltin hydride (1.2 equiv.) and AIBN (0.5 equiv.) in toluene was added dropwise to the refluxing solution. The reaction mixture was allowed to reflux for 12 hours. Toluene was evaporated in vacuum. A two-neck flask was charged with lithium bromide (2.04 mmol) and flame dried under high vacuum. Upon cooling, tetrakis(triphenylphosphine) palladium(0) (0.034 mmol), CuCl (1.7 mmol) were added, and the mixture was degassed (4×) under high vacuum with an argon purge. Dry DMF (4.0 mL) was introduced with concomitant stirring, followed by the addition of aryl iodide (0.35 mmol) and the tributyltin reaction mixture. The resulting mixture was rigorously degassed (4×) by the freeze-pump-thaw method using liquid nitrogen under argon atmosphere. The reaction mixture was stirred at room temperature for 1 h, then heated to 110° C. for 12 hours. Following completion of the coupling as monitored by TLC, the reaction mixture was cooled, diluted with Et$_2$O, and washed with brine. The aqueous layer was further extracted with Et$_2$O (3×), the combined organic layers were washed with water (2×40 mL) and brine (2×40 mL), and dried over Na$_2$SO$_4$. Concentration in vacuum afforded a residue that was purified by column chromatography (Si-gel/10% ethyl acetate in hexane) to afford O4 and O2 (52% and 63%) as a yellow and white solid.

Compound O2: 2-phenyl-1,1'-binaphthalene

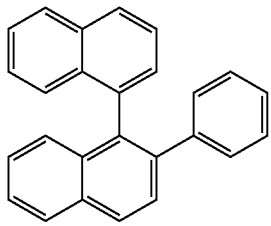

O2

Chromatographic purification (hexane) afforded compound 02 (63% yield) as a white solid; m.p. 133° C.; Rf=0.5 (hexane); $^1$H NMR (600 MHz; CDCl$_3$) δ 8.05 (1H, d, J=8.5 Hz), 7.99 (1H, d, J=8.2 Hz), 7.89 (1H, d, J=8.2 Hz), 7.83 (1H, d, J=8.2 Hz), 7.70 (1H, d, H=8.5 Hz), 7.52-7.40 (4H, m), 7.31-7.27 (4H, m), 7.14-7.11 (2H, m), 7.07-7.03 (3H, m). $^{13}$C NMR (150 MHz; CDCl$_3$) δ 142.1, 139.7, 137.1, 135.9, 133.7, 133.5, 133.4, 132.8, 129.4 (2C), 128.6, 128.4, 128.2, 128.1, 127.9, 128.7, 127.6, 127.4, 126.8, 126.5, 126.2, 125.9, 125.8, 125.4. HRMS (ED: calcd for C$_{26}$H$_{18}$ [M]+ 330.1409, found 330.1405.

Example 18. General Procedures for the Synthesis of Compounds P3 & P5

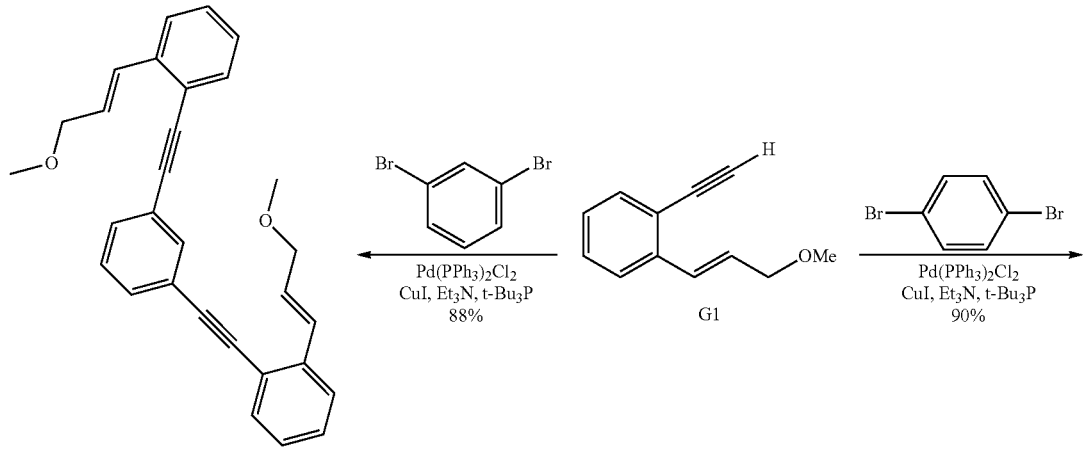

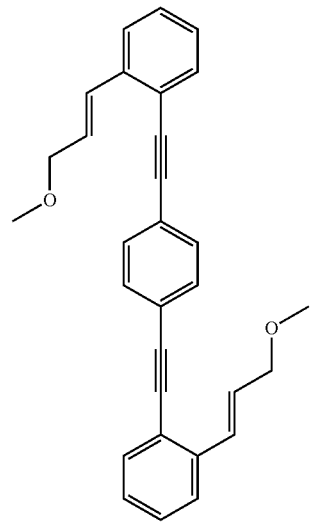

Sonogashira Cross Coupling of 1,4-Dibromobenzene and 1,3-Dibromobenzene with Acetylene G2 (P3 and P5):

A suspension of dibromobenzene (2 mmol), PdCl$_2$(PhCN)$_2$ (0.20 mmol), Cu(I) iodide (0.20 mmol) in 20 mL of triethylamine was degassed three times with freeze/pump/thaw technique in a flame dried round bottom flask. Once the reaction mixture was completely thawed and the atmosphere replaced with argon, tri-tert-butylphosphine (0.40 mmol in a 10% solution of toluene) was added, immediately followed by 2.0 equiv. of acetylene G1 (4.0 mmol) solution in dry THF using a syringe. The reaction was allowed to react for 12 hours and monitored by TLC. After total consumption of the aryl bromide, the reaction mixture was filtered through celite and extracted with methylene chloride (3×30 mL). The organic layer was washed with a saturated solution of ammonium chloride, water and dried over anhydrous Na$_2$SO$_4$. Solvent was removed under reduced pressure. The reaction mixture was purified by flash chromatography (eluent: hexane/ethyl acetate) on silica gel to afford compounds P5 (90%) and P3 (88%) as oils.

Compound P5: 1,4-bis((2-((E)-3-methoxyprop-1-en-1-yl)phenyl)ethynyl)benzene

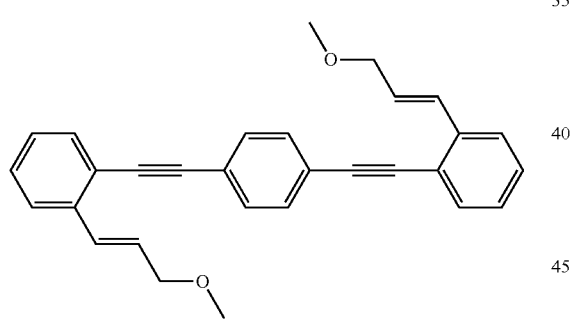

Chromatographic purification (15% ethyl acetate in hexane) afforded compound P5 (90% yield) as a dark brown oil. Rf=0.6 (20% ethyl acetate in hexane); $^1$H NMR (400 MHz; CDCl$_3$) δ 7.59-7.57 (2H, m), 7.55 (4H, s), 7.53-7.52 (2H, m), 7.31 (2H, dt, J=7.4, 1.1 Hz), 7.23 (2H, dt, J=7.6, 1.2 Hz), 7.20 (2H, d, J=16.0 Hz), 6.41 (2H, td, J=16.0, 6.0 Hz), 4.17 (4H, dd, J=6.0, 1.4 Hz), 3.43 (6H, s). $^{13}$C NMR (100 MHz; CDCl$_3$) δ 138.3 (2C), 132.6 (2C), 131.5 (4C), 130.2 (2C), 128.8 (2C), 128.2 (2C), 127.4 (2C), 125.2 (2C), 123.3 (2C), 121.7 (2C), 93.8 (2C), 89.9 (2C), 73.2 (2C), 58.1 (2C). HRMS (ED: calcd for C$_{30}$H$_{26}$O$_2$ [M]+ 418.1933, found 418.1926. IR (neat, cm$^{-1}$): 3059, 2221, 1498, 966.

Compound P3: 1,3-bis((2-((E)-3-methoxyprop-1-en-1-yl)phenyl)ethynyl)benzene

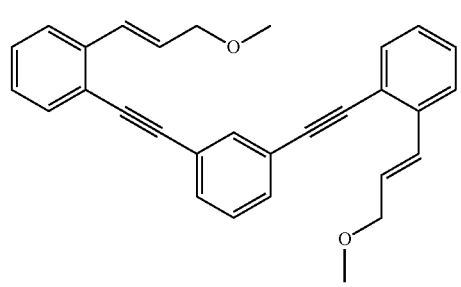

Chromatographic purification (15% ethyl acetate in hexane) afforded compound P3 (88% yield) as a light brown oil. Rf=0.6 (20% ethyl acetate in hexane); $^1$H NMR (400 MHz; CDCl$_3$) δ 7.75 (1H, t, J=1.5 Hz), 7.59 (2H, d, J=7.7 Hz), 7.55-7.52 (4H, m), 7.37 (1H, t, J 7.9 Hz), 7.32 (2H, dt, J=7.4, 1.1 Hz), 7.24 (2H, m), 7.20 (2H, d, J=16.0 Hz), 6.41 (2H, td, J=16.0, 6.0 Hz), 4.17 (4H, dd, J=6.0, 1.4 Hz), 3.43 (6H, s). $^{13}$C NMR (100 MHz; CDCl$_3$) δ (2C), 134.5, 132.8 (2C), 131.5 (2C), 130.4 (2C), 128.9 (2C), 128.7 (2C), 128.3 (2C), 127.5 (2C), 125.3 (2C), 123.9 (2C), 121.8 (2C), 93.3 (2C), 88.6 (2C), 73.4 (2C), 58.2 (2C). HRMS (EI): calcd for C$_{30}$H$_{26}$O$_2$ [M]+ 418.1933, found 418.1929. IR (neat, cm$^{-1}$): 3051, 2224, 1488, 978.

Compound P4': 1,3-di(naphthalen-2-yl)benzene

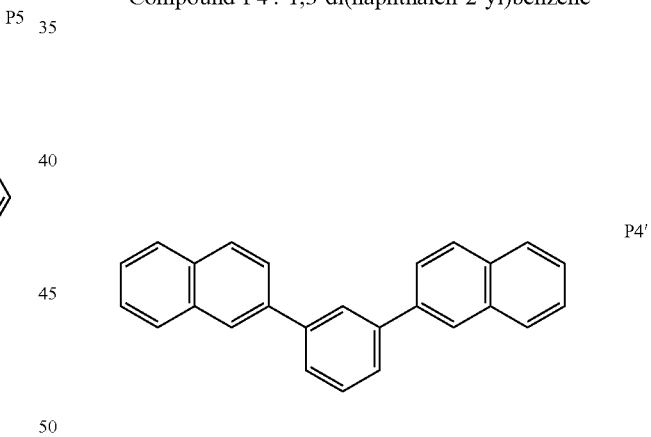

Chromatographic purification (40% DCM in hexane) afforded compound P4' (65% yield) as a white solid; m.p. 142-143° C.; Rf=0.5 (50% DCM in hexane); $^1$H NMR (600 MHz; CDCl$_3$) δ 8.15 (2H, s), 8.08 (1H, t, J=1.7 Hz), 7.97 (2H, d, J=8.6 Hz), 7.95 (2H, d, J=7.7 Hz), 7.91 (2H, d, J=7.7 Hz), 7.86 (2H, dd, J=8.5, 1.8 Hz), 7.76 (2H, dd, J=7.6, 1.8 Hz), 7.62 (1H, t, J=7.6 Hz), 7.55-7.51 (4H, m). $^{13}$C NMR (150 MHz; CDCl$_3$) δ 142.0 (2C), 138.7 (2C), 133.9 (2C), 132.9 (2C), 129.6, 128.7 (2C), 128.4 (2C), 127.9 (2C), 126.9, 126.7 (2C), 126.6 (2C), 126.2 (4C), 125.9 (2C). C$_{26}$H$_{18}$ [M]+ 330.1409, found 330.1401. IR (neat, cm$^{-1}$): 3066, 2901, 1461, 1011.

Compound P6': 1,4-di(naphthalen-2-yl)benzene

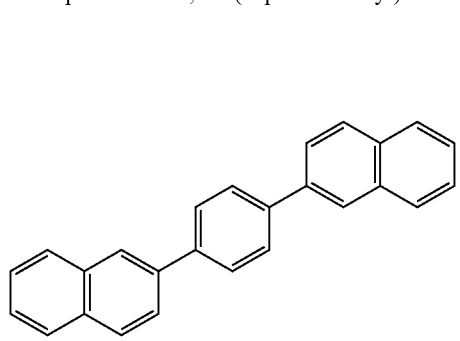

Chromatographic purification (50% DCM in hexane) afforded compound P6' (68% yield) as a white solid; m.p. 259-260° C.; Rf=0.5 (50% DCM in hexane); $^1$H NMR (600 MHz; CDCl$_3$) δ 8.12 (2H, s), 7.96 (2H, d, J=8.5 Hz), 7.94 (2H, d, J=8.5 Hz), 7.89 (2H, d, J=8.0 Hz), 7.87 (4H, s), 7.85 (2H, dd, J=8.5, 1.6 Hz), 7.54-7.49 (4H, m).). $^{13}$C NMR (150 MHz; CDCl$_3$) δ 140.3 (2C), 138.2 (2C), 134.0 (2C), 132.9 (2C), 128.7 (2C), 128.5 (2C), 128.1 (4C), 127.9 (2C), 126.6 (2C), 126.2 (2C), 125.9 (2C), 125.7 (2C). C$_{26}$H$_{18}$ [M]+ 330.1409, found 330.1402. IR (neat, cm$^{-1}$): 3063, 2905, 1456, 1014.

Example 19. General Procedures for Iodination (O3 & Q1)

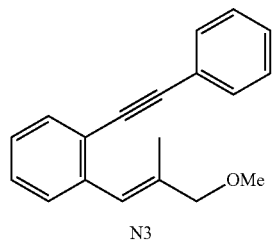 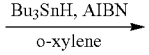

N3

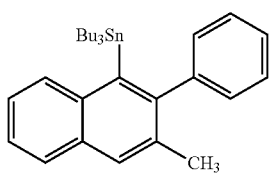 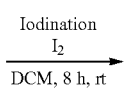

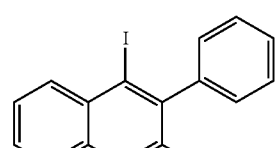

O3 - 92%

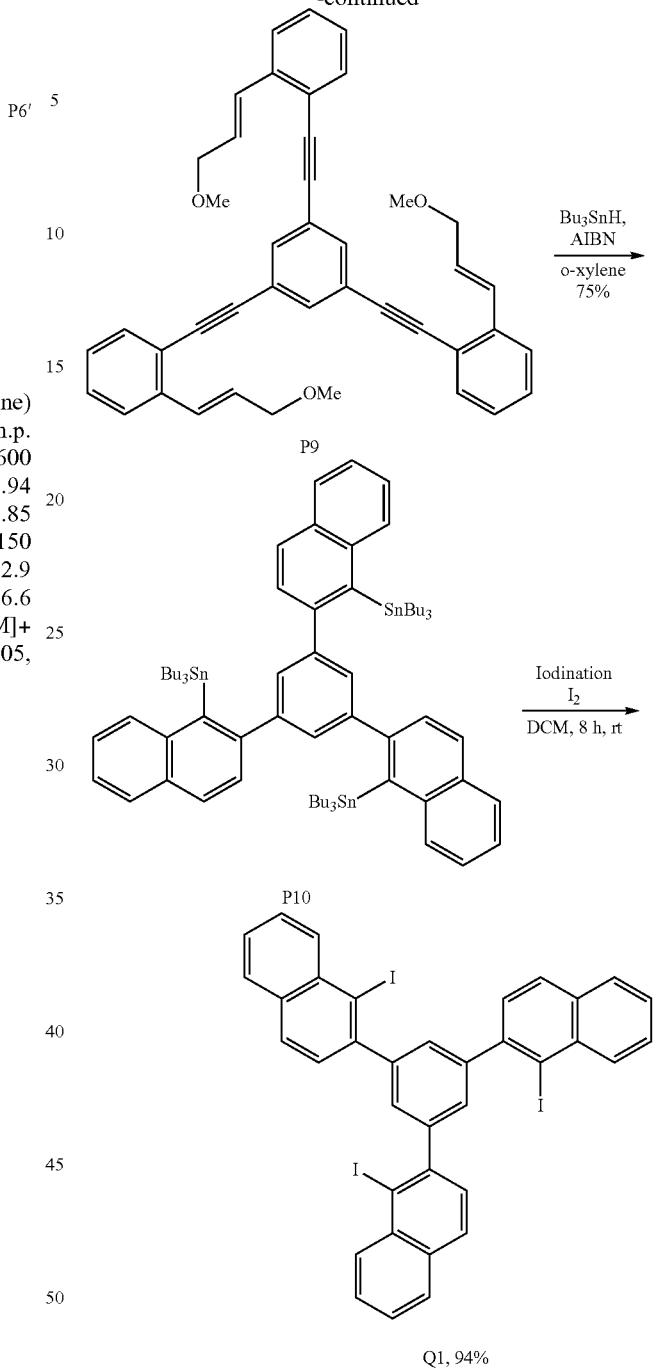

A solution of enyne (N3 and P9) (0.34 mmol) in toluene was brought to reflux. A solution of tributyltin hydride (1.2 equiv. for N3 and 3.6 equiv. for P9) and AIBN (0.5 equiv. for N3 and 1.5 equiv. for P9) in toluene was added dropwise to the refluxing solution. The reaction mixture was allowed to reflux for 12 hours. Toluene was evaporated in vacuum and the reaction mixture was dissolved in 2 mL of dichloromethane. Iodine (0.51 mmol for N3 and 1.53 mmol for P9) was added and the reaction mixture stirred at room temperature for 8 hour. The reaction was quenched with a saturated aqueous solution of sodium bisulfite. The aqueous layer was extracted with dichloromethane (4×), the combined organic layer was dried over sodium sulfate and concentrated. Chromatographic purification (hexane) afforded compound O3 (yield: 92% white solid) and Q1 (yield: 94% white solid).

Compound P9: 1,3,5-tris((2-((E)-3-methoxyprop-1-en-1-yl)phenyl)ethynyl)benzene

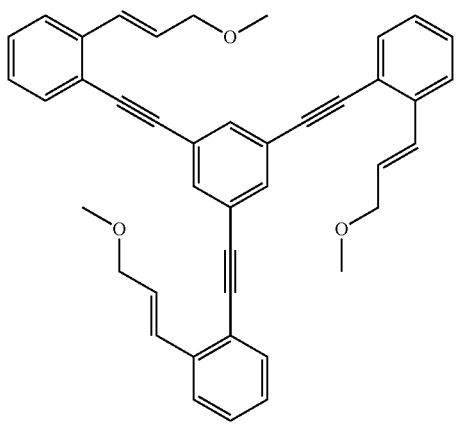

P9

Chromatographic purification (15% ethyl acetate in hexane) afforded compound P9 (90% yield) as a light brown oil. Rf=0.6 (20% ethyl acetate in hexane); $^1$H NMR (400 MHz; CDCl$_3$) δ 7.70 (3H, s), 7.61 (3H, d, J=7.7 Hz), 7.55 (3H, d, J=7.5 Hz), 7.34 (3H, t, J=7.5 Hz), 7.26 (3H, t, J=7.8 Hz), 7.21 (3H, d, J=16.0 Hz), 6.43 (3H, dt, J=16.0, 5.5 Hz), 4.20 (6H, d J=5.5 Hz), 3.45 (9H, s). $^{13}$C NMR (100 MHz; CDCl$_3$) δ 38.5 (3C), 134.1 (3C), 132.8 (3C), 130.2 (3C), 129.0 (3C), 128.5 (3C), 127.6 (3C), 125.3 (3C), 124.3 (3C), 121.5 (3C), 92.5 (3C), 89.3 (3C), 73.3 (6C), 58.3 (9C). HRMS (EI): calcd for C$_{42}$H$_{36}$O$_3$ [M]+ 588.2664, found 588.2661. IR (neat, cm$^{-1}$): 3066, 2212, 1471, 949.

Compound P10': 1,3,5-tri(naphthalen-2-yl)benzene

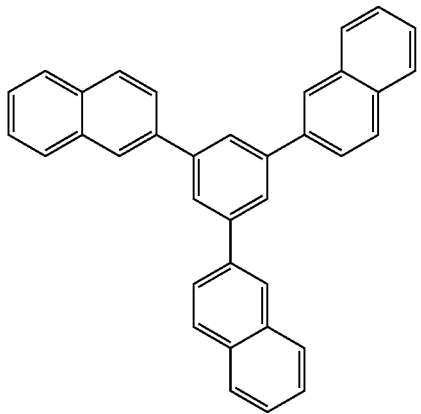

P10'

Chromatographic purification (40% DCM in hexane) afforded compound P10' (92% yield) as a white solid; m.p. 240-241° C.; Rf=0.5 (50% DCM in hexane); $^1$H NMR (400 MHz; CDCl$_3$) δ 8.22 (3H, s), 8.08 (3H, s), 8.01-7.91 (12H, m), 7.57-7.50 (6H, m). $^{13}$C NMR (100 MHz; CDCl$_3$) δ 142.5 (3C), 138.5 (3C), 133.7 (3C), 132.8 (3C), 128.6 (3C), 128.3 (3C), 127.7 (3C), 126.4 (3C), 126.1 (6C), 125.8 (3C), 125.7 (3C). HRMS (EI): calcd for C$_{36}$H$_{24}$[M]+ 456.1878, found 456.1871. IR (neat, cm$^{-1}$): 3098, 2777, 1311, 764.

Example 20. Procedure for the Synthesis of Q3

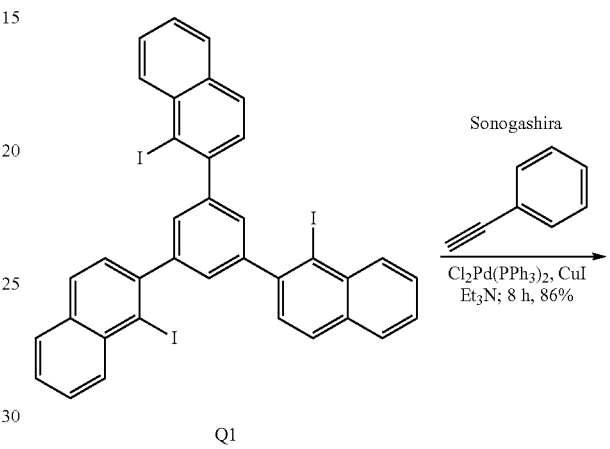

Q1

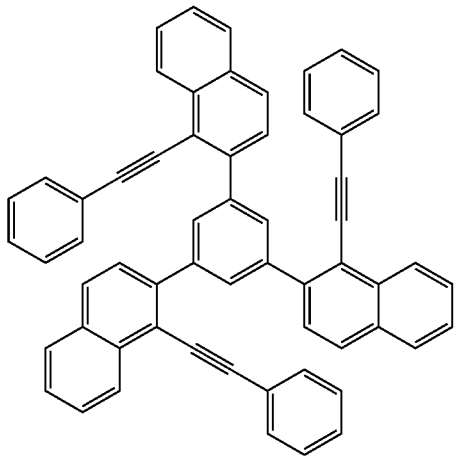

Q3

A suspension of aryl iodide (0.292 g, 0.35 mmol), PdCl$_2$(PPh$_3$)$_2$ (0.07 mmol), Cu(I) iodide (0.07 mmol) in 8 mL of triethylamine was degassed three times with freeze/pump/thaw technique in a flame-dried round bottom flask. Then 1.0 equiv. of phenyl acetylene (3.1 equiv.; 1.08 mmol) was added dropwise using a syringe. The reaction was allowed to react for 8 hours and monitored by TLC. After total consumption of the aryl iodide, the reaction mixture was filtered through celite and extracted with methylene chloride (3×30 mL). The organic layer was washed with a saturated solution of ammonium chloride (2×30 mL), water (2×30 mL) and dried over anhydrous Na$_2$SO$_4$. Solvent was removed in vacuo. The reaction mixture was purified by flash chromatography on silica gel, (eluent: hexane/EtOAc) to afford compound Q3 (86%) as yellow solid.

Compound Q1:
1,3,5-tris(1-iodonaphthalen-2-yl)benzene

Chromatographic purification (30% DCM in hexane) afforded compound Q1 (94% yield) as a white solid; m.p>280° C.; Rf=0.5 (50% DCM in hexane); $^1$H NMR (400 MHz; CDCl$_3$) δ 8.37 (3H, d, J=8.5 Hz), 7.88 (3H, d, J=8.4 Hz), 7.83 (3H, d, J=8.0 Hz), 7.64-7.61 (6H, m), 7.54 (3H, t, J=7.4 Hz), 7.49 (3H, s). $^{13}$C NMR (100 MHz; CDCl$_3$) δ 145.9 (3C), 145.5 (3C), 135.2 (3C), 133.8 (3C), 133.3 (3C), 130.1 (3C), 128.8 (3C), 128.5 (3C), 128.3 (3C), 127.9 (126.8 (3C), 104.5 (3C). HRMS (EI): calcd for C$_{36}$H$_{21}$I$_3$[M]+ 833.8777, found 833.8772.

Compound Q3: 1,3,5-tris(1-(phenylethynyl)naphthalen-2-yl)benzene

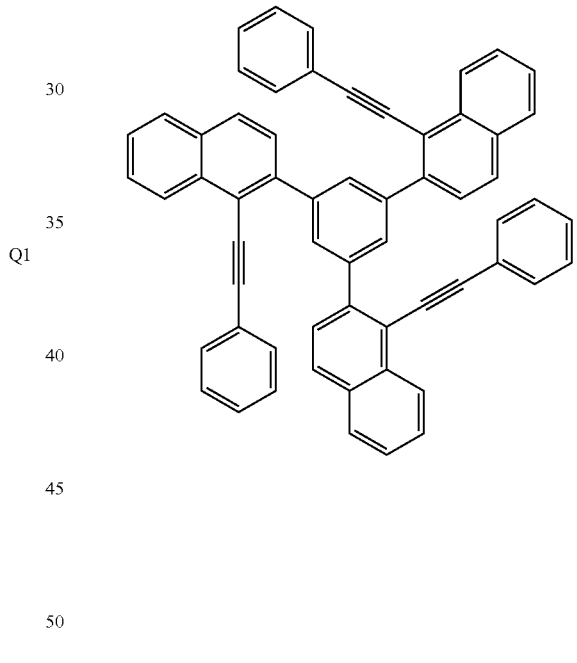

Chromatographic purification (30% DCM in hexane) afforded compound Q3 (86% yield) as a white solid; m.p. 212-213° C.; Rf=0.5 (50% DCM in hexane); $^1$H NMR (400 MHz; CDCl$_3$) δ 8.66 (3H, d, J=8.3 Hz), 8.35 (3H, s), 7.91 (3H, d, J=8.1 Hz), 7.87 (3H, d, J=8.5 Hz), 7.76 (3H, d, J=8.5 Hz), 7.68 (3H, dt, J=6.9, 1.1 Hz), 7.60-7.56 (3H, m), 7.41-7.39 96H, m), 7.21-7.16 (3H, m), 7.14-7.10 (6H, m). $^{13}$C NMR (100 MHz; CDCl$_3$) δ 142.7 (3C), 140.8 (3C), 133.8 (3C), 132.5 (3C), 131.7 (6C), 130.8 (3C), 128.8 (3C), 128.4 (6C), 128.3 (6C), 127.8 (3C), 127.4 (3C), 126.9 (3C), 126.6 (3C), 123.5 (3C), 188.9 (3C), 98.3 (3C), 87.7 (3C). HRMS (EI): calcd for C$_{60}$H$_{36}$[M]+ 756.2817, found 756.2808.

Example 21. General Procedure for the Synthesis of Compounds Q4, Q2, Q5

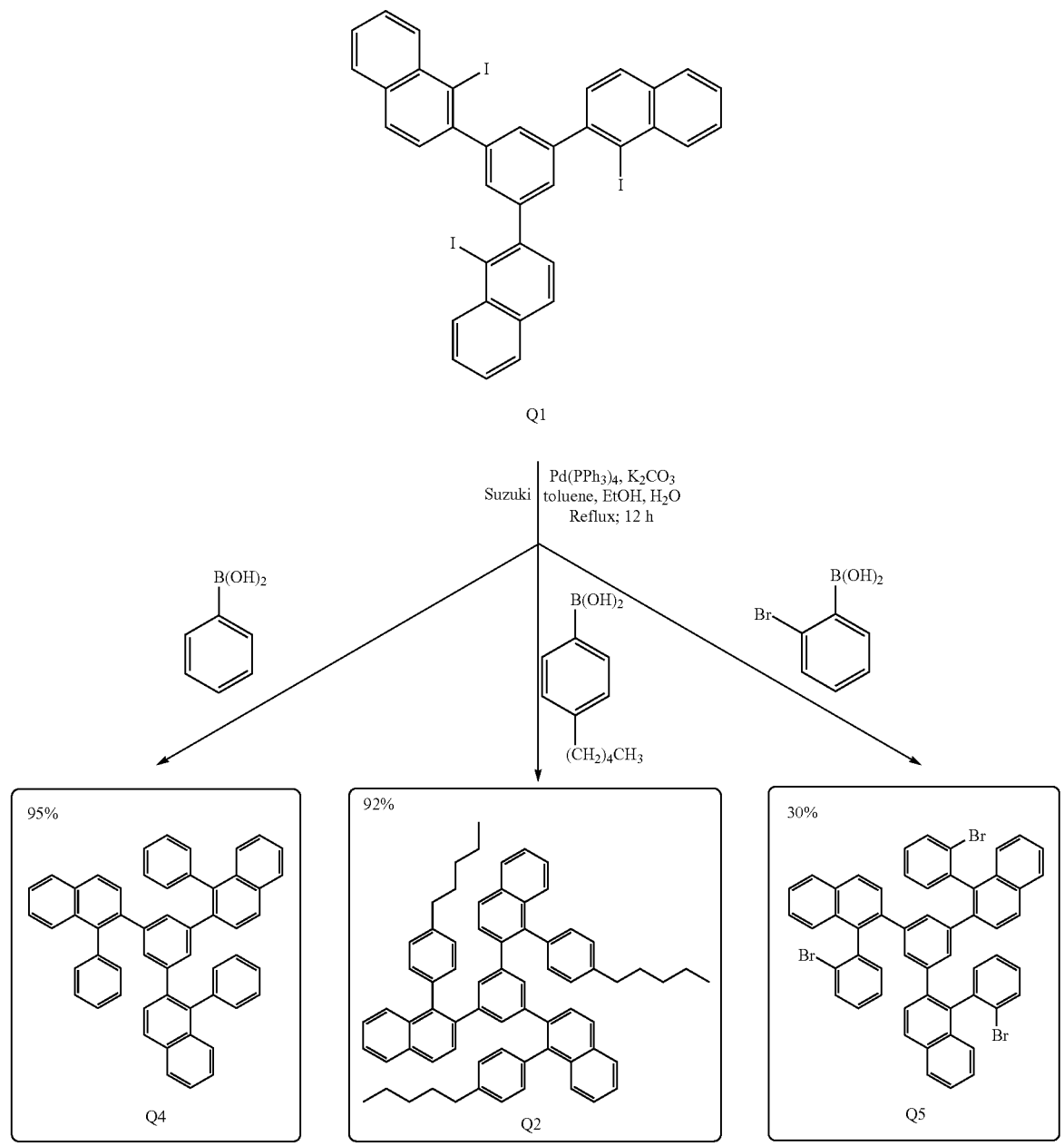

Suzuki Coupling

To a 25 ml flask, 1,3,5-tris(1-iodonaphthalen-2-yl)benzene Q1 (0.20 mmol, 167 mg), aryl boronic acid (0.72 mmol), (10 mol %) Pd(PPh$_3$)$_4$ (23 mg), K$_2$CO$_3$, (276 mg), 2 mL toluene, 0.5 mL EtOH and 0.5 mL H$_2$O were added. The mixture was degassed by two "freeze-pump-thaw" cycles and then heated to reflux overnight. Standard work-up and purification by column chromatography (Silica gel, PE/DCM) furnished compounds Q4 (95%), Q2 (92%) and Q5 (30%) as white solids.

Compound Q4: 1,3,5-tris(1-phenylnaphthalen-2-yl)benzene

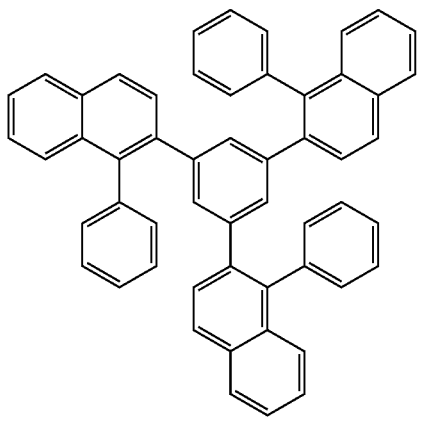

Chromatographic purification (30% DCM in hexane) afforded compound Q4 (95% yield) as a white solid; m.p. 141-142° C.; Rf=0.5 (50% DCM in hexane); $^1$H NMR (600 MHz; CDCl$_3$) δ 7.89 (3H, d, J=8.1 Hz), 7.81 (3H, d, J=8.5 Hz), 7.65 (3H, d, J=8.5 Hz), 7.47 (3H, t, J=7.3 Hz), 7.40-7.35 (12H, m), 7.05-7.00 (9H, m), 6.75 (3H, s).). $^{13}$C NMR (100 MHz; CDCl$_3$) δ 140.9 (3C), 139.3 (3C), 138.4 (3C), 137.6 (3C), 132.9 (3C), 132.7 (3C), 131.9 (6C), 130.4 (3C), 128.6 (3C), 128.1 (6C), 128.0 (3C), 127.5 (3C), 126.9 (3C), 126.8 (3C), 126.3 (3C), 125.8 (3C). HRMS (EI): calcd for C$_{36}$H$_{21}$I$_3$[M]+ 684.2817, found 684.2811.

Compound Q2: 1,3,5-tris(1-(4-pentylphenyl)naphthalen-2-yl)benzene

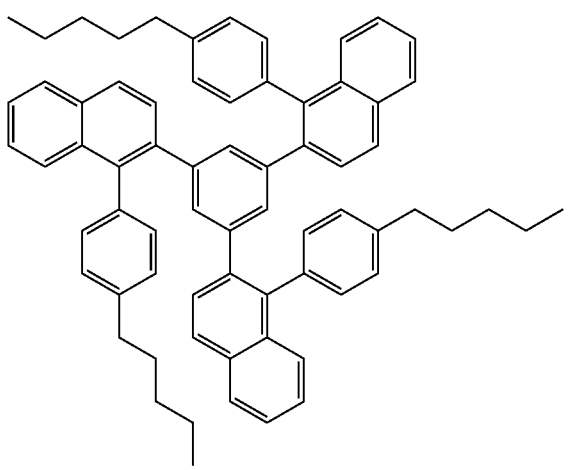

Chromatographic purification (30% DCM in hexane) afforded compound Q2 (92% yield) as a white semisolid; Rf=0.5 (50% DCM in hexane); $^1$H NMR (400 MHz; CDCl$_3$) δ 7.89 (3H, d, J=8.0 Hz), 7.79 (3H, d, J=8.5 Hz), 7.75 (3H, d, J=8.5 Hz), 7.48 (3H, t, J=7.4 Hz), 7.40 (3H, t, J=7.4 Hz), 7.21 (6H, d, J=7.7 Hz), 6.99 (9H, d, J=8.0 Hz), 6.77 (3H, d, J=1.0 Hz) 2.72 (6H, t, J=7.9 Hz), 1.75-1.71 (6H, m), 1.39-1.37 (12H, m), 0.92 (9H, t, J=6.7 Hz). $^{13}$C NMR (100 MHz; CDCl$_3$) δ 141.4 (3C), 140.8 (3C), 138.4 (3C), 137.6 (3C), 136.5 (3C), 132.9 (3C), 132.8 (3C), 131.9 (6C), 130.4 (3C), 128.7 (3C), 128.0 (6C), 127.9 (3C), 127.3 (3C), 127.1 (3C), 126.1 (3C), 125.7 (3C), 36.0 (3C), 32.0 (3C), 31.5 (3C), 22.8 (3C), 14.3 (3C). HRMS (EI): calcd for C$_{36}$H$_{21}$I$_3$ [M]+ 894.5165, found 894.5155.

Compound Q5: 1,3,5-tris(1-(2-bromophenyl)naphthalen-2-yl)benzene

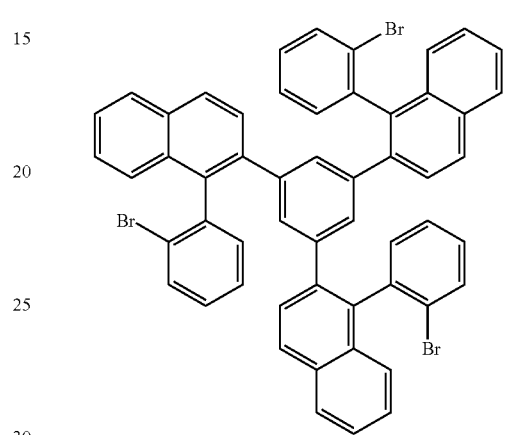

Chromatographic purification (30% DCM in hexane) afforded compound Q5 (30% yield) as a white solid; m.p. 277-278° C.; Rf=0.5 (50% DCM in hexane); $^1$H NMR (600 MHz; CDCl$_3$) δ 7.90 (3H, d, J=8.2 Hz), 7.88 (3H, d, J=8.5 Hz), 7.62-7.61 (3H, m), 7.48 (3H, t, J=7.4 Hz), 7.40 (3H, t, J=7.4 Hz), 7.34 (3H, d, J=8.4 Hz), 7.28-7.21 (6H, m), 7.15 (3H, d, J=8.5 Hz), 6.99 (3H, s), 6.68-6.66 (3H, m). $^{13}$C NMR (150 MHz; CDCl$_3$) δ 140.7 (6C), 138.3 (3C), 136.4 (3C), 133.4 (3C), 132.7 (3C), 132.6 (3C), 130.0 (3C), 129.4 (3C), 128.6 (3C), 128.4 (6C), 128.3 (3C), 127.2 (3C), 126.6 (3C), 126.5 (3C), 126.2 (3C), 125.9 (3C). HRMS (EI): calcd for C$_{54}$H$_{33}$Br$_3$[M]+ 918.0132, found 918.0122.

Example 22. Library of Enynes and Naphthalenes Synthesized

Figure 13A:
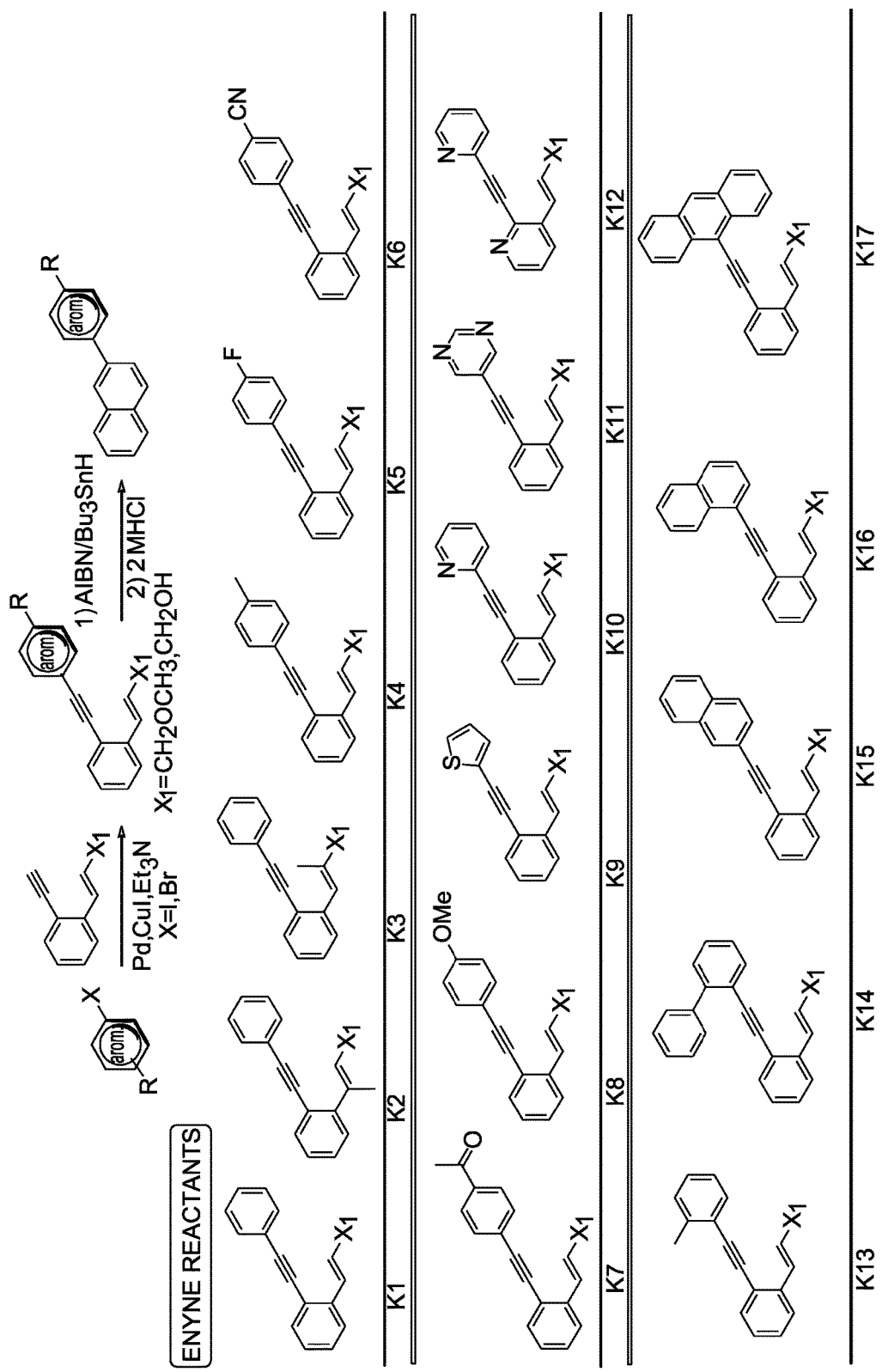
Figure 13B:
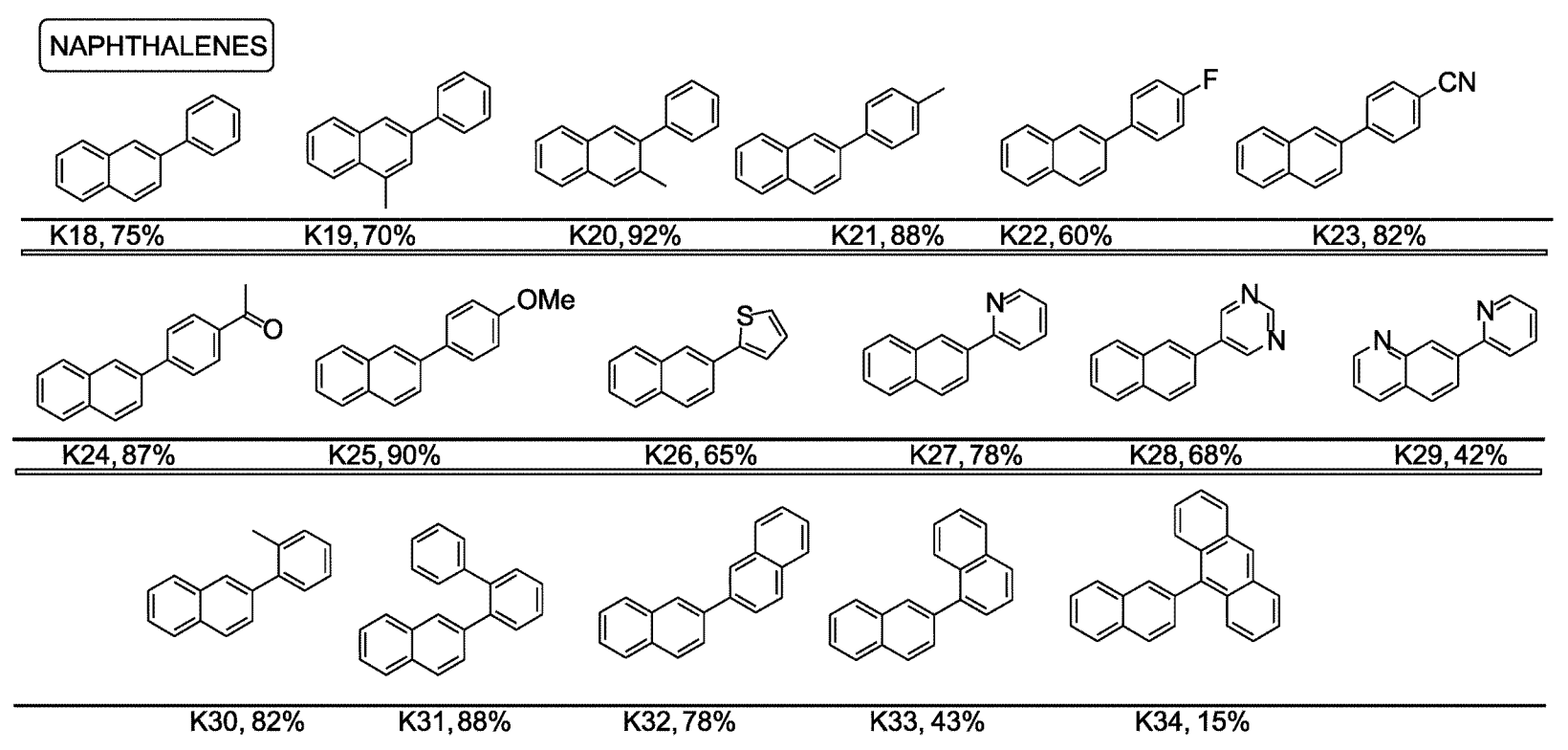

FIGS. 13A and 13B depict the wide variety of naphthalene derivatives (FIG. 13B) that may be synthesized from the enyne reactants (FIG. 13A) according to the method of the present invention.

Compound K21: 2-(p-tolyl)naphthalene

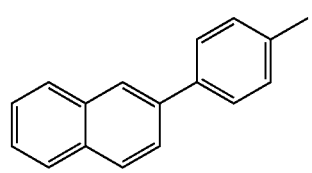

Chromatographic purification (hexane) afforded compound K21 (89% yield) as White solid, m. p. 93-95° C. (lit. 92-94° C.). Rf=0.5 (hexane); 1H NMR (400 MHz; CDCl$_3$)

δ 7.99 (1H, s) 7.79-7.86 (3H, m) 7.69 (2H, dd, J=1.7, 8.5 Hz), 7.59 (2H, d, J=8.1 Hz), 7.39-7.47 (2H, m), 7.24 (2H, d, J=8 Hz), 2.38 (3H, s), $^{13}$C NMR (100 MHz; CDCl$_3$) δ 138.6, 138.4, 137.3, 129.7, 128.5, 128.3, 127.8, 127.4, 126.4, 125.9, 125.7, 125.6, 21.27.

Compound K22: 2-(4-fluorophenyl)naphthalene

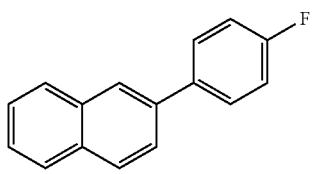

Chromatographic purification (hexane) afforded compound K22 (60% yield) as a white solid; Rf=0.5 (hexane); $^1$H NMR (600 MHz; CDCl$_3$) δ 8.00 (1H, s), 7.92 (1H, d, J=8.5 Hz), 7.90 (1H, d, J=7.9 Hz), 7.88 (1H, d, J=7.7 Hz), 7.71-7.67 (3H, m), 7.54-7.49 (2H. m), 7.18 (2H, t, J=8.6 Hz). $^{13}$C NMR (150 MHz; CDCl$_3$) δ 162.8 (d, J=245.2 Hz), 137.8, 137.5, 133.9, 132.8, 129.2 (2C, d, J=7.9 Hz), 128.7, 128.3, 127.9, 126.6, 126.2, 125.9, 125.6, 115.9 (2C, d, J=21.2 Hz), HRMS (ED: calcd for C$_{16}$H$_{11}$F [M]+ 222.0845, found 222.0841. IR (neat, cm$^{-1}$): 3059, 1602, 1512, 1500, 1221, 1157, 1094, 822, 747.

Compound K23: 4-(naphthalen-2-yl)benzonitrile

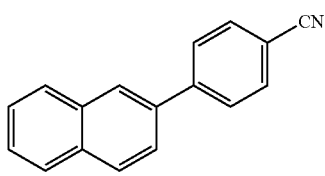

Chromatographic purification (5% DCM in hexane) afforded compound K23 (82% yield) as a white solid. Rf=0.5 (5% DCM in hexane); m.p. 127-129° C.; 1H NMR (300 MHz, CDCl$_3$) δ 8.05 (1H, s), 7.92 (3H, m), 7.81 (2H, d, J=8.4 Hz), 7.75 (2H, d, J=8.4 Hz), 7.70 (1H, dd, J=8.4, 1.5 Hz), 7.53 (2H, m); 13CNMR (75 MHz, CDCl$_3$) δ 145.5, 136.3, 133.4, 133.1, 132.6, 128.9, 128.3, 127.9, 127.6, 126.7, 126.6, 126.5, 124.8, 118.9, 110.9.

Compound K24: 1-(4-(naphthalen-2-yl)phenyl)ethan-1-one

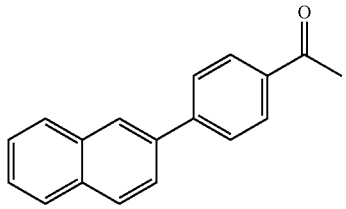

Chromatographic purification (hexane) afforded compound K24 (87% yield) as pale yellow solid: m.p.: 129-130° C.; Rf=0.5 (hexane); 1H NMR (400 MHz, CDCl$_3$): δ 8.09-8.07 (3H, m), 7.95-7.87 (3H, m), 7.83 (2H, d, J=8.8 Hz), 7.77-7.75 (1H, dd, J=8.4 Hz), 7.55-7.51 (2H, m), 2.66 (3H, s). 13C NMR (100 MHz, CDCl$_3$): δ 197.9, 145.8, 137.2, 135.9, 133.6, 133.1, 129.1, 128.8, 128.4, 127.8, 127.6, 126.7, 126.6, 126.5, 125.3, 26.8.

Compound K25: 2-(4-methoxyphenyl)naphthalene

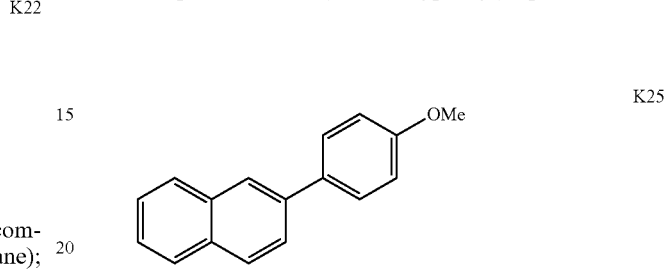

Chromatographic purification (hexane) afforded compound K25 (78% yield) as a white solid; m. p. 130-131° C.; Rf=0.5 (hexane); $^1$H NMR (400 MHz; CDCl$_3$) δ 8.04-7.97 (1H, m), 7.92-7.83 (3H, m), 7.73 (1H, dd, J=8.5, 1.9 Hz), 7.71-7.64 (2H, m), 7.54-7.42 (2H, m), 7.08-6.99 (2H, m), 3.88 (3H, s). $^{13}$C NMR (CDCl3, 100 MHz) δ 159.5, 138.4, 134.0, 133.9, 132.6, 128.7, 128.6 (2C), 128.30, 127.9, 126.5, 125.9 25.7, 125.3, 114.5 (2C), 55.6. HRMS (EI): calcd for C$_{17}$H$_{15}$O [M]+ 234.1045, found 234.1038. IR (neat, cm$^{-1}$): 2959, 2921, 2826, 1283, 1038, 822, 814, 746, 694, 689.

Compound K26: 2-(naphthalen-2-yl)thiophene

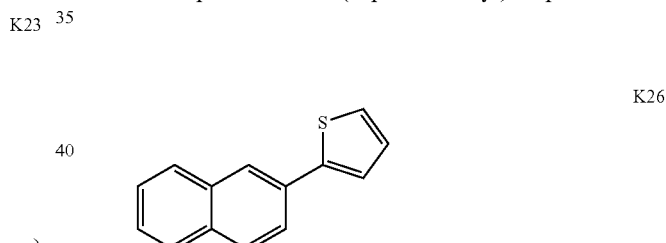

Chromatographic purification (hexane) afforded compound K26 (65% yield) as a yellow solid. $^1$H NMR (300 MHz; CDCl$_3$) δ 8.00 (1H, s), 7.67-7.79 (4H, m), 7.36-7.45 (3H, m), 7.24 (1H, dd, J=1.2, 5.1 Hz), 7.05 (1H, dd, J=3.6, 5.1 Hz)$^{13}$C NMR (75 MHz; CDCl$_3$): δ 144.5, 133.8, 132.8, 131.9, 128.6, 128.2, 128.1, 127.8, 126.6, 126.0, 125.1, 124.5, 124.3, 123.6.

Compound K27: 2-(naphthalen-2-yl)pyridine

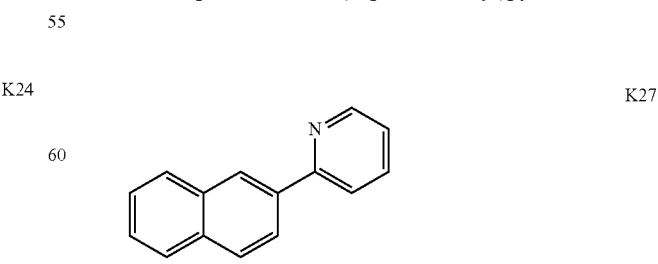

Chromatographic purification (hexane) afforded compound K27 (78% yield) as a yellow oil; Rf=0.2 (hexane); $^1$H NMR (600 MHz; CDCl₃) δ 8.76 (1H, d, J=3.4 Hz), 8.49 (1H, s), 8.15 (1H, dd, J=8.6, 1.6 Hz), 7.97-7.94 (2H, m), 7.89-7.87 (2H, m), 7.79 (2H, dt, J=7.6, 1.7 Hz), 7.53-7.50 (2H, m), 7.28-7.26 (1H, m). $^{13}$C NMR (150 MHz; CDCl₃) δ 157.6, 150.0, 137.0, 136.9, 133.9, 133.7, 128.9, 128.7, 127.9, 126.7, 126.5 (2C), 124.8, 122.4, 121.0. HRMS (ED: calcd for $C_{15}H_{11}N$ [M]+ 205.0891, found 205.0888. IR (neat, cm$^{-1}$): 3078, 2922, 1488, 877.

Compound K28: 5-(naphthalen-2-yl)pyrimidine

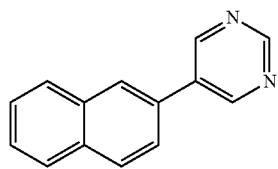

K28

Chromatographic purification (5% ethylacetate in hexane) afforded compound K28 (68% yield) as a yellow solid; m.p. 108° C. Rf=0.2 (5% ethylacetate in hexane); $^1$H NMR (400 MHz; CDCl₃) δ 9.24 (1H, s), 9.07 (2H, s), 8.04 (1H, d, J=1.4 Hz), 7.99 (1H, d, J=8.5 Hz), 7.94-7.89 (2H, m), 7.68 (1H, dd, J=8.5, 1.8 Hz), 7.58-7.53 (2H, m). $^{13}$C NMR (100 MHz; CDCl₃) δ 157.6, 155.3 (2C), 134.5, 133.7, 133.4, 131.7, 129.6, 128.5, 128.0, 127.2, 127.1, 126.6, 124.5. HRMS (ED: calcd for $C_{14}H_{10}N_2$ [M]+ 206.0844, found 206.0838. IR (neat, cm$^{-1}$): 3051, 2778, 1476, 821.

Compound K29: 7-(pyridin-2-yl)quinolone

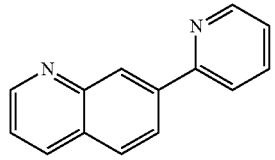

K29

Chromatographic purification (hexane) afforded compound K29 (78% yield) as a white solid; Rf=0.2 (hexane); $^1$H NMR (600 MHz; CDCl₃) δ 8.96 (1H, dd, J=4.1, 1.6 Hz), 8.77 (1H, dd, J=4.8, 0.7 Hz), 8.63 (1H, s), 8.35 (1H, dd, J=8.5, 1.6 Hz), 8.20 (1H, d, J=7.9 Hz), 7.95 (2H, t, J=8.3 Hz), 7.83 (1H, m), 7.44-7.42 (1H, m), 7.32-7.29 (1H, m). $^{13}$C NMR (150 MHz; CDCl₃) δ 156.7, 150.9, 149.9, 148.5, 140.5, 137.0, 135.8, 128.5, 128.3, 127.4, 125.6, 122.6, 121.5, 121.2. HRMS (ED: calcd for $C_{14}H_{10}N_2$ [M]+ 206.0844, found 206.0838. IR (neat, cm$^{-1}$): 3102, 2878, 1234, 798.

Compound K30: 2-(o-tolyl)naphthalene

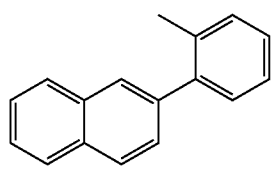

K30

Chromatographic purification (hexane) afforded compound K30 (82% yield) as colorless oil. Rf=0.5 (hexane); 1H NMR (300 MHz, CDCl₃): δ 7.79-7.83 (m, 3H), 7.74 (s, 1H), 7.42-7.46 (m, 3H), 7.24-7.31 (m, 4H), 2.28 (s, 3H). 13C NMR (75.4 MHz, CDCl₃): δ 141.9, 139.6, 135.6, 133.4, 132.3, 130.4, 130.1, 128.0, 127.83, 127.77, 127.72, 127.5, 127.4, 126.2, 125.9, 20.4.

Compound K31: 2-([1,1'-biphenyl]-2-yl)naphthalene

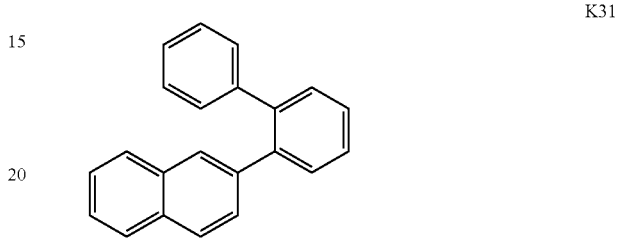

K31

Chromatographic purification (hexane) afforded compound K31 (88% yield) as a white solid. Rf=0.4 (hexane); $^1$H NMR (600 MHz; CDCl₃) δ 7.77-7.76 (3H, m), 7.60 (1H, d, J=8.5 Hz), 7.56-7.54 (1H. m), 7.49-7.43 (5H, m), 5.04 (5H, s), 7.13 (1H, dd, J=8.5, 1.7 Hz). $^{13}$C NMR (150 MHz; CDCl₃) δ 141.7, 141.0, 140.6, 139.5, 133.6, 132.3, 131.2, 130.9, 130.1 (2C), 128.6 (2C), 128.2 (3C), 127.8 (3C), 127.2, 126.7, 126.1, 126.0. $C_{22}H_{16}$[M]+ 280.1252, found 280.1250. IR (neat, cm$^{-1}$): 3087, 2189, 1495.

Compound K32: 2,2'-binaphthalene

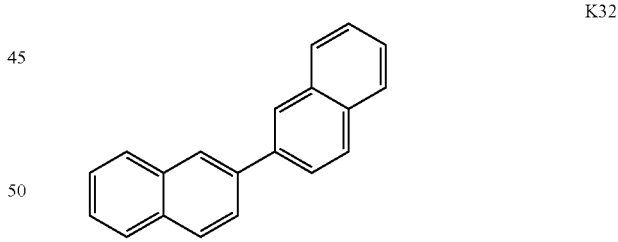

K32

Chromatographic purification (hexane) afforded compound K32 (78% yield) as a white solid; m.p. 187-188° C.; Rf=0.5 (hexane); $^1$H NMR (600 MHz; CDCl₃) δ 8.19 (2H, d, J=1.0 Hz), 7.98-7.94 (4H, m), 7.91-7.89 (4H, m), 7.55-7.50 (4H, m). $^{13}$C NMR (150 MHz; CDCl₃) δ 138.6 (2C), 133.9 (2C), 132.9 (2C), 128.7 (2C), 128.4 (2C), 127.9 (2C), 126.6 (2C), 126.3 (2C), 126.2 (2C), 125.9 (2C). HRMS (EI): calcd for $C_{20}H_{14}$ [M]+ 254.1096, found 254.1094. IR (neat, cm$^{-1}$): 3054, 2921, 1923, 1593, 1129.

Compound K33: 1,2'-binaphthalene

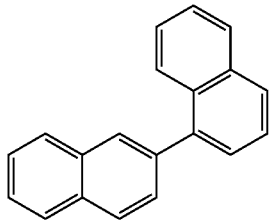

Chromatographic purification (hexane) afforded compound K33 (43% yield) as a white solid; m.p. 137-139° C.; Rf=0.5 (hexane); $^1$H NMR (600 MHz; CDCl$_3$) δ 7.97-7.90 (7H, m), 7.66-7.64 (1H, m), 7.59-7.50 (5H, m), 7.45-7.42 (1H, m). $^{13}$C NMR (150 MHz; CDCl$_3$) δ 140.4, 138.5, 134.0, 133.6, 132.8, 132.0, 128.9, 128.7, 128.5, 128.3, 128.0 (2C), 127.9, 127.4, 126.5, 126.3 (2C), 126.2, 126.0, 125.6. HRMS (EI): calcd for C$_{20}$H$_{14}$ [M]+ 254.1096, found 254.1090. IR (neat, cm$^{-1}$): 3039, 2921, 1928, 1503, 1131.

Compound K34: 9-(naphthalen-2-yl)anthracene

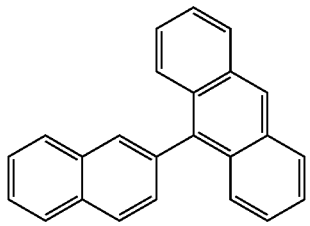

Chromatographic purification (hexane) afforded compound K34 (15% yield) as a white solid; Rf=0.5 (hexane); $^1$H NMR (600 MHz; CDCl$_3$) δ 8.54 (1H, S), 8.08-8.00 (4H, m), 7.93-7.88 (3H, m), 7.68 (2H, d, J=8.8 Hz), 7.61-7.55 (3H, m), 7.47 (2H, t, J=7.0 Hz), 7.32 (2H, t, J=7.3 Hz). $^{13}$C NMR (150 MHz; CDCl$_3$) δ 136.8, 136.3, 133.4, 132.7, 131.4, 130.4, 130.1, 129.5, 128.4, 128.2, 128.1, 127.9, 126.8, 126.7, 126.4, 126.2, 125.4, 125.1. HRMS (EI): calcd for C$_{24}$H$_{16}$ [M]+ 304.1252, found 304.1250.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method of synthesizing a Sn-functionalized aromatic compound comprising a fused aromatic ring system, the method comprising contacting a stannane compound and a reactant compound having the following structure (I)-a:

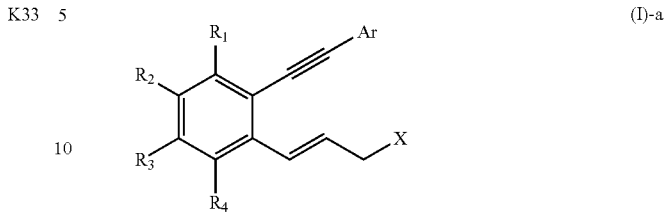

wherein:
each R$_1$ R$_2$, R$_3$, and R$_4$ independently comprises hydrogen, alkenyl, alkynyl, aryl, or any two adjacent R$_1$ R$_2$, R$_3$, and R$_4$ together form a fused aromatic ring system;
X is selected from the group consisting of hydroxyl, alkoxy, amino, and phenyl; and
Ar comprises aryl or heteroaryl, which may be unsubstituted or substituted;
and wherein the Sn-functionalized aromatic compound comprising a fused aromatic ring system has the following structure (IV)-b:

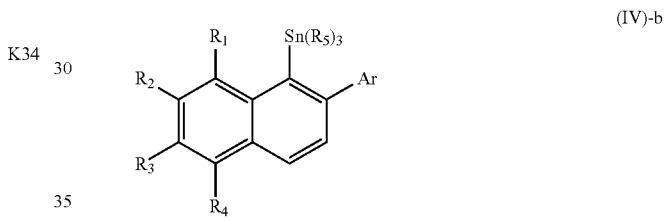

wherein:
each R$_1$ R$_2$, R$_3$, and R$_4$ independently comprises hydrogen, alkenyl, alkynyl, aryl, or any two adjacent R$_1$ R$_2$, R$_3$, and R$_4$ together form a fused aromatic ring system;
Ar comprises aryl or heteroaryl, which may be unsubstituted or substituted; and
each R$_5$ independently comprises alkyl, aryl, or heteroaryl.

2. The method of claim 1 wherein X is selected from the group consisting of hydroxyl and amine.

3. The method of claim 1 wherein Ar is substituted with an alkenyl, an alkynyl, or both an alkenyl and an alkynyl.

4. The method of claim 1 wherein the reactant compound has the following structure (I)-a:

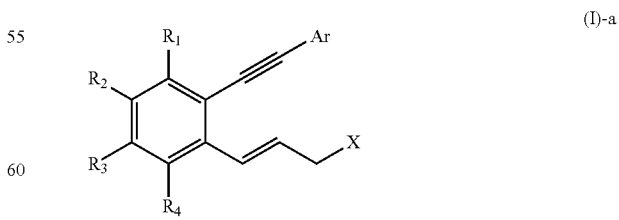

wherein:
each R$_1$ R$_2$, R$_3$, and R$_4$ independently comprises hydrogen, alkenyl, alkynyl, aryl, or any two adjacent R$_1$ R$_2$, R$_3$, and R$_4$ together form a fused aromatic ring system;

X is selected from the group consisting of hydroxyl and amine; and

Ar comprises aryl or heteroaryl, which may be unsubstituted or substituted.

5. The method of claim 1 wherein the reactant compound has any of the following structures (III)-a, (III)-b, and (III)-c:

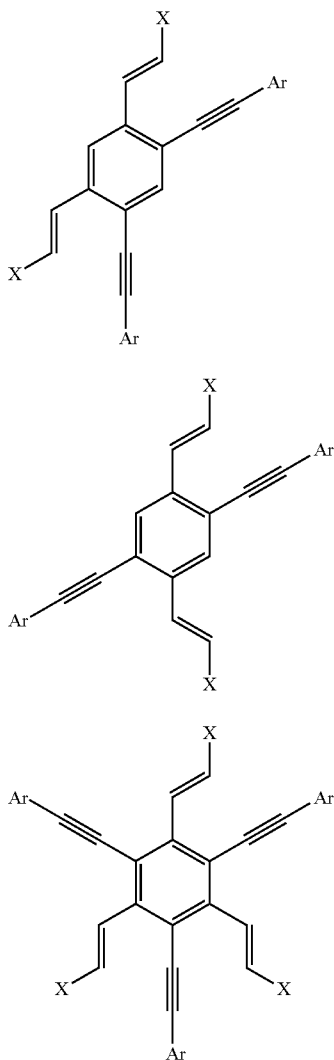

(III)-a (III)-b (III)-c wherein:
X is selected from the group consisting of hydroxyl, alkoxy, amino, and phenyl; and Ar comprises aryl or heteroaryl, which may be unsubstituted or substituted.

6. The method of claim 1 further comprising contacting the Sn-functionalized aromatic compound comprising a fused aromatic ring system with an acid to thereby prepare a substituted naphthalene having the structure (V)-b:

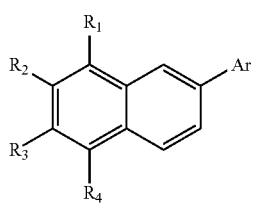

(V)-b wherein:
each $R_1$ $R_2$, $R_3$, and $R_4$ independently comprises hydrogen, alkenyl, alkynyl, aryl, or any two adjacent $R_1$ $R_2$, $R_3$, and $R_4$ together form a fused aromatic ring system; and Ar comprises aryl or heteroaryl, which may be unsubstituted or substituted.

7. The method of claim 1 further comprising contacting the Sn-functionalized aromatic compound comprising a fused aromatic ring system with an organic precursor compound to prepare a substituted naphthalene having the structure (VI)-b:

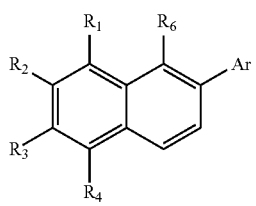

(VI)-b wherein:
each $R_1$ $R_2$, $R_3$, and $R_4$ independently comprises hydrogen, alkenyl, alkynyl, aryl, or any two adjacent $R_1$ $R_2$, $R_3$, and $R_4$ together form a fused aromatic ring system;

Ar comprises aryl or heteroaryl, which may be unsubstituted or substituted; and $R_6$ is selected from the group consisting of alkyl, aryl, heteroaryl, amino, alkoxy, and halo.

* * * * *